(12) United States Patent
Xue et al.

(10) Patent No.: US 11,130,095 B1
(45) Date of Patent: Sep. 28, 2021

(54) STERILIZATION EXHAUST GAS TREATING SYSTEM AND METHOD FOR TREATING ETHYLENE OXIDE-CONTAINING STERILIZATION EXHAUST GAS BY USING THE SAME

(71) Applicants: Chio Kang Medical, Inc., Palo Alto, CA (US); Qiaokang Biotech (Guangdong) Co., LTD., Guangzhou (CN)

(72) Inventors: Jianlong Xue, Guangzhou (CN); Dongxin Hou, Guangzhou (CN); Yecheng He, Guangzhou (CN); Weiguo Wang, Guangzhou (CN); Qinghua Xiao, Guangzhou (CN); Liqing Zhu, Guangzhou (CN); Shengwei Hu, Guangzhou (CN); Xin Yin, Guangzhou (CN); Xiuling Zhong, Guangzhou (CN); Lixiong Feng, Guangzhou (CN)

(73) Assignees: Chio Kang Medical, Inc., Palo Alto, CA (US); Qiaokang Biotech (Guangdong) Co., LTD., Guangzhou (CN)

( * ) Notice: Subject to any disclaimer, the term of this patent is extended or adjusted under 35 U.S.C. 154(b) by 0 days.

(21) Appl. No.: 17/012,857

(22) Filed: Sep. 4, 2020

Related U.S. Application Data

(63) Continuation of application No. PCT/CN2020/101140, filed on Jul. 9, 2020.

(30) Foreign Application Priority Data

Mar. 18, 2020 (CN) .......................... 202010190366.5
Mar. 18, 2020 (CN) .......................... 202010190370.1

(Continued)

(51) Int. Cl.
*B01D 53/02* (2006.01)
*B01D 53/75* (2006.01)
(Continued)

(52) U.S. Cl.
CPC .............. *B01D 53/75* (2013.01); *A61L 2/206* (2013.01); *A61L 2/26* (2013.01); *B01D 53/047* (2013.01);
(Continued)

(58) Field of Classification Search
CPC ................ B01D 53/75; B01D 53/0423; B01D 53/0438; B01D 53/0446; B01D 53/0462;
(Continued)

(56) References Cited

U.S. PATENT DOCUMENTS 2,586,670 A 2/1919 Lambersten
1,954,056 A 4/1934 Miller
(Continued)

FOREIGN PATENT DOCUMENTS

CN 1223166 A 7/1999
CN 101224381 A 7/2008
(Continued)

OTHER PUBLICATIONS

International Application No. PCT/CN2020/101140 as prepared by the Chinese International Searching Authority filed Jul. 9, 2020, 59 pages.
(Continued)

*Primary Examiner* — Christopher P Jones
(74) *Attorney, Agent, or Firm* — Adsero IP

(57) ABSTRACT

The present disclosure provides a sterilization exhaust gas treatment system, which may include a gas liquefaction recovery system, a pressure swing adsorption recovery system, a reaction system, a temperature swing adsorption recovery system, a hydration system, a recovery and storage
(Continued)

system, and a wastewater treatment system. The gas liquefaction recovery system, the pressure swing adsorption recovery system, the reaction system, the temperature swing adsorption recovery system, and the hydration system may be fluidly connected in sequence through first connecting pipes. The gas liquefaction recovery system, the pressure swing adsorption recovery system, and the temperature swing adsorption recovery system may each be fluidly connected to the recovery and storage system through second connecting pipes. The hydration system may be fluidly connected to the wastewater treatment system through wastewater pipes. The present disclosure also provides a method for treating ethylene oxide-containing sterilization exhaust gas using the sterilization exhaust gas treatment system.

30 Claims, 18 Drawing Sheets

Specification includes a Sequence Listing.

(30) Foreign Application Priority Data

| Mar. 18, 2020 | (CN) | ......................... 202010190385.8 |
| Mar. 18, 2020 | (CN) | ......................... 202010193555.7 |
| Mar. 19, 2020 | (CN) | ......................... 202010194449.1 |
| Mar. 19, 2020 | (CN) | ......................... 202010194457.6 |

(51) Int. Cl.

| *B01D 53/04* | (2006.01) |
| *B01D 53/18* | (2006.01) |
| *C02F 3/30* | (2006.01) |
| *C02F 3/00* | (2006.01) |
| *B01D 53/86* | (2006.01) |
| *B01D 53/14* | (2006.01) |
| *A61L 2/26* | (2006.01) |
| *A61L 2/20* | (2006.01) |
| *B01D 53/047* | (2006.01) |
| *C02F 103/18* | (2006.01) |
| *C02F 101/34* | (2006.01) |
| *A61L 101/44* | (2006.01) |

(52) U.S. Cl.
CPC ..... *B01D 53/0423* (2013.01); *B01D 53/0438* (2013.01); *B01D 53/0446* (2013.01); *B01D 53/0462* (2013.01); *B01D 53/1437* (2013.01); *B01D 53/1487* (2013.01); *B01D 53/18* (2013.01); *B01D 53/8668* (2013.01); *C02F 3/006* (2013.01); *C02F 3/30* (2013.01); *A61L 2101/44* (2020.08); *A61L 2202/13* (2013.01); *B01D 2252/103* (2013.01); *B01D 2253/102* (2013.01); *B01D 2255/70* (2013.01); *B01D 2257/70* (2013.01); *B01D 2259/402* (2013.01); *B01D 2259/45* (2013.01); *C02F 2101/34* (2013.01); *C02F 2103/18* (2013.01); *F25J 2205/60* (2013.01)

(58) Field of Classification Search
CPC .............. B01D 53/047; B01D 53/1437; B01D 53/1487; B01D 53/18; B01D 53/8668; B01D 2252/103; B01D 2253/102; B01D 2255/70; B01D 2257/70; B01D 2259/402; B01D 2259/45; A61L 2/206; A61L 2/26; A61L 2101/44; A61L 2202/13; C02F 3/006; C02F 3/30; C02F 2101/34; C02F 2103/18; F25J 2205/60
See application file for complete search history.

(56) References Cited

U.S. PATENT DOCUMENTS

| 2,817,689 | A | 12/1957 | White |
| 3,022,054 | A | 2/1962 | Kotzebue |
| 3,572,391 | A | 3/1971 | Hirsh et al. |
| 3,598,543 | A | 8/1971 | Crosby et al. |
| 3,844,739 | A | 10/1974 | Alfrey, Jr. |
| 3,961,920 | A | 6/1976 | Gilbert |
| 3,997,633 | A | 12/1976 | Leva et al. |
| 4,112,054 | A | 9/1978 | Feingold et al. |
| 4,119,539 | A | 10/1978 | Ettel et al. |
| 4,134,425 | A | 1/1979 | Gussefeld et al. |
| 4,243,636 | A | 1/1981 | Shiraki et al. |
| 4,301,113 | A | 11/1981 | Alguire et al. |
| 4,517,167 | A | 5/1985 | Popescu et al. |
| 4,549,363 | A | 10/1985 | Buonicore |
| 4,555,251 | A | 11/1985 | Jonsson et al. |
| 4,831,196 | A | 5/1989 | Buonicore et al. |
| 5,084,075 | A | 1/1992 | Sircar |
| 5,204,075 | A | 4/1993 | Jain et al. |
| 5,270,000 | A | 12/1993 | Goldner et al. |
| 5,283,035 | A | 2/1994 | Karthaus et al. |
| 5,290,345 | A | 3/1994 | Osendorf et al. |
| 5,511,409 | A | 4/1996 | Knaebel |
| 5,522,808 | A | 6/1996 | Skalla |
| 5,607,652 | A | 3/1997 | Hellmuth et al. |
| 5,641,455 | A | 6/1997 | Rosenlund et al. |
| 5,702,669 | A | 12/1997 | Green |
| 5,741,470 | A | 4/1998 | Wenzler |
| 5,755,857 | A | 5/1998 | Acharya et al. |
| 5,779,773 | A | 7/1998 | Cam et al. |
| 5,964,927 | A | 10/1999 | Graham et al. |
| 6,156,101 | A | 12/2000 | Naheiri |
| 6,684,648 | B2 | 2/2004 | Faqih |
| 6,743,402 | B2 | 6/2004 | Shimakawa |
| 7,316,733 | B1 | 1/2008 | Hedrick |
| 7,625,535 | B2 | 12/2009 | Yamaguchi |
| 8,110,156 | B2 | 2/2012 | Ricciardi et al. |
| 8,431,085 | B2 | 4/2013 | Froderberg et al. |
| 9,616,143 | B2 | 4/2017 | Snyder et al. |
| 10,987,443 | B1 | 4/2021 | Hu et al. |
| 2002/0046569 | A1 | 4/2002 | Faqih |
| 2002/0197194 | A1 | 12/2002 | Machado et al. |
| 2005/0145108 | A1 | 7/2005 | Rubin |
| 2006/0236860 | A1 | 10/2006 | Sumida et al. |
| 2006/0249027 | A1 | 11/2006 | Adolphsen et al. |
| 2007/0209383 | A1 | 9/2007 | Hutton |
| 2008/0078289 | A1 | 4/2008 | Sergi et al. |
| 2008/0080999 | A1 | 4/2008 | Bondar |
| 2008/0289591 | A1 | 11/2008 | Tessier et al. |
| 2010/0196194 | A1 | 8/2010 | Voeten et al. |
| 2011/0265644 | A1 | 11/2011 | Swami et al. |
| 2011/0283885 | A1 | 11/2011 | Thiele |
| 2012/0031268 | A1 | 2/2012 | Yaghi et al. |
| 2012/0298207 | A1 | 11/2012 | Woelk et al. |
| 2014/0119989 | A1 | 5/2014 | Hayashi |
| 2014/0251130 | A1 | 9/2014 | Sprinkle et al. |
| 2014/0290162 | A1 | 10/2014 | Tanimoto |
| 2016/0010883 | A1 | 1/2016 | Jomitz et al. |
| 2017/0056813 | A1* | 3/2017 | McMahon ......... B01D 53/0473 |
| 2019/0076776 | A1 | 3/2019 | Mahecha-Botero et al. |
| 2019/0151791 | A1 | 5/2019 | Awadh et al. |
| 2019/0175971 | A1 | 6/2019 | Moore et al. |
| 2020/0148655 | A1 | 5/2020 | Duff et al. |

FOREIGN PATENT DOCUMENTS

| CN | 101549241 | A | 10/2009 |
| CN | 101773762 | A | 7/2010 |
| CN | 201632182 | U | 11/2010 |
| CN | 102173384 | A | 9/2011 |
| CN | 102219642 | A | 10/2011 |
| CN | 102921570 | A | 2/2013 |
| CN | 202802975 | U | 3/2013 |
| CN | 202933710 | U | 5/2013 |
| CN | 103394278 | A | 11/2013 |
| CN | 103657383 | A | 3/2014 |

(56) References Cited

FOREIGN PATENT DOCUMENTS

| | | |
|---|---|---|
| CN | 103706233 A | 4/2014 |
| CN | 203507806 U | 4/2014 |
| CN | 203564952 U | 4/2014 |
| CN | 103800926 A | 5/2014 |
| CN | 203749877 U | 8/2014 |
| CN | 203750388 U | 8/2014 |
| CN | 203750389 U | 8/2014 |
| CN | 104014227 A | 9/2014 |
| CN | 104275085 A | 1/2015 |
| CN | 204261680 U | 4/2015 |
| CN | 204447972 U | 7/2015 |
| CN | 104815535 A | 8/2015 |
| CN | 105132060 A | 12/2015 |
| CN | 105327665 A | 2/2016 |
| CN | 105664822 A | 2/2016 |
| CN | 205300112 U | 6/2016 |
| CN | 106475021 A | 3/2017 |
| CN | 106582126 A | 4/2017 |
| CN | 206535551 U | 10/2017 |
| CN | 206853397 U | 1/2018 |
| CN | 107677016 A | 2/2018 |
| CN | 207169397 U | 4/2018 |
| CN | 207187436 U | 4/2018 |
| CN | 207745676 U | 8/2018 |
| CN | 207913454 U | 9/2018 |
| CN | 108607511 A | 10/2018 |
| CN | 208218734 U | 12/2018 |
| CN | 109382064 A | 2/2019 |
| CN | 208448985 U | 2/2019 |
| CN | 208893903 U | 5/2019 |
| CN | 110145747 A | 8/2019 |
| CN | 110302634 A | 10/2019 |
| CN | 110404485 A | 11/2019 |
| CN | 209662917 U | 11/2019 |
| CN | 110833754 A | 2/2020 |
| CN | 210021633 U | 2/2020 |
| CN | 210088451 U | 2/2020 |
| DE | 4236622 C1 | 3/1994 |
| EP | 0130319 A2 | 1/1985 |
| EP | 0350677 A1 | 1/1990 |
| EP | 1302478 A1 | 4/2003 |
| EP | 2883598 A1 | 6/2015 |
| GB | 1472091 A | 4/1977 |
| JP | 2008114210 A | 5/2008 |
| WO | WO2011002277 A1 | 1/2011 |
| WO | WO2019236249 A1 | 12/2019 |

OTHER PUBLICATIONS

International Application No. PCT/CN2020/100143 as prepared by the Chinese International Searching Authority filed Jul. 3, 2020, 25 pages.
U.S. Appl. No. 17/002,500, TrackOne Bypass CON Application filed Aug. 25, 2020, 61 pages.
International Application No. PCT/CN2020/100125 as prepared by the Chinese International Searching Authority filed Jul. 3, 2020, 27 pages.
U.S. Appl. No. 17/002,523, TrackOne Bypass CON Application filed Aug. 25, 2020, 72 pages.
U.S. Appl. No. 17/002,523 Non-Final Office Action, dated Oct. 27, 2020, 54 pages.
International Application No. PCT/CN2020/100115 as prepared by the Chinese International Searching Authority filed Jul. 3, 2020, 22 pages.
U.S. Appl. No. 17/002,529, TrackOne Bypass Con Application filed Aug. 25, 2020, 64 pages.
International Application No. PCT/CN2020/100119 as prepared by the Chinese International Searching Authority filed Jul. 3, 2020, 29 pages.
U.S. Appl. No. 17/002,540, TrackOne Bypass CON Application filed Aug. 25, 2020, 89 pages.
International Application No. PCT/CN2020/100120 as prepared by the Chinese International Searching Authority filed Jul. 3, 2020, 28 pages.
U.S. Appl. No. 17/004,730, TrackOne Bypass CON Application filed Aug. 27, 2020, 77 pages.
International Application No. PCT/CN2020/101142 as prepared by the Chinese International Searching Authority filed Jul. 9, 2020, 29 pages.
U.S. Appl. No. 17/012,864, TrackOne Bypass CON Application filed Sep. 4, 2020, 78 pages.
International Application No. PCT/CN2020/100144 as prepared by the Chinese International Searching Authority filed Jul. 3, 2020, 24 pages.
U.S. Appl. No. 17/004,903, TrackOne Bypass CON Application filed Aug. 27, 2020, 67 pages.
U.S. Appl. No. 17/004,903 Notice of Allowance, dated Nov. 6, 2020, 19 pages.
International Application No. PCT/CN2020/100122 as prepared by the Chinese International Searching Authority filed Jul. 3, 2020, 34 pages.
U.S. Appl. No. 17/004,930, TrackOne Bypass CON Application filed Aug. 27, 2020, 80 pages.
U.S. Appl. No. 17/004,930 Office Action-Restriction Requirement, dated Nov. 4, 2020, 6 pages.
International Application No. PCT/CN2020/100113 as prepared by the Chinese International Searching Authority filed Jul. 3, 2020, 35 pages.
U.S. Appl. No. 17/004,971, TrackOne Bypass Con Application filed Aug. 27, 2020, 75 pages.
U.S. Appl. No. 17/002,540, Office Action-Restriction Requirement, dated Dec. 1, 2020, 7 pages.
U.S. Appl. No. 17/002,500, Non-Final Office Action dated Dec. 8, 2020, 109 pages.
Kahm et al., 2018 "Lyapunov exponents with Model Predictive Control for exothermic batch reactors" IFAC-PapersOnline, 51, 417-422.
U.S. Appl. No. 17/004,971, Office Action-Restriction Requirement, dated Dec. 9, 2020, 6 pages.
U.S. Appl. No. 17/002,523 Notice of Allowance, dated Dec. 17, 2020, 35 pages.
U.S. Appl. No. 17/004,930 Office Action-Restriction Requirement, Dec. 18, 2020, 8 pages.
U.S. Appl. No. 17/002,540, Non-Final Office Action dated Dec. 30, 2020, 62 pages.
U.S. Appl. No. 17/004,930 Non-Final Office Action dated Jan. 26, 2021, 28 pages.
International Search Report and Written Opinion, International Application No. PCT/CN2020/101140 dated Dec. 21, 2020, 11 pages.
International Search Report and Written Opinion, International Application No. PCT/CN2020/100143 dated Dec. 21, 2020, 9 pages.
International Search Report and Written Opinion, International Application No. PCT/CN2020/100125 dated Dec. 23, 2020, 9 pages.
International Search Report and Written Opinion, International Application No. PCT/CN2020/100115 dated Dec. 16, 2020, 11 pages.
International Search Report and Written Opinion, International Application No. PCT/CN2020/100119 dated Dec. 17, 2020, 9 pages.
International Search Report and Written Opinion, International Application No. PCT/CN2020/101142 dated Dec. 16, 2020, 11 pages.
International Search Report and Written Opinion, International Application No. PCT/CN2020/100144 dated Dec. 18, 2020, 10 pages.
U.S. Appl. No. 17/002,500, Final Office Action dated Feb. 8, 2021, 57 pages.
U.S. Appl. No. 17/004,971, Notice of Allowance, dated Feb. 8, 2021, 30 pages.
U.S. Appl. No. 17/002,529, Non-Final Office Action-Restriction Requirement dated Feb. 17, 2021, 11 pages.

(56) References Cited

OTHER PUBLICATIONS

U.S. Appl. No. 17/002,540, Final Office Action, dated Mar. 26, 2021, 36 pages.
U.S. Appl. No. 17/004,730, Non-Final Office Action, dated Apr. 1, 2021, 30 pages.
U.S. Appl. No. 17/002,500, Non-Final Office Action, dated Apr. 15, 2021, 89 pages.
U.S. Appl. No. 17/002,540, Notice of Allowance, dated Apr. 26, 2021, 21 pages.
U.S. Appl. No. 17/004,930, Notice of Allowance, dated Apr. 28, 2021, 35 pages.
U.S. Appl. No. 17/004,903, Notice of Allowance, dated May 17, 2021, 20 pages.
U.S. Appl. No. 17/002,529, Notice of Allowance, dated May 3, 2021, 30 pages.
U.S. Appl. No. 17/002,523, Notice of Allowance, dated May 27, 2021, 26 pages.
U.S. Appl. No. 17/012,864, Notice of Allowance, dated Jun. 15, 2021, 56 pages.
U.S. Appl. No. 17/004,730, Notice of Allowance, dated Jun. 24, 2021, 30 pages.
U.S. Appl. No. 17/002,500, Notice of Allowance, dated Jul. 8, 2021, 27 pages.

\* cited by examiner

SEQUENCE LISTING

<160> NUMBER OF SEQ ID NOS: 10

<210> SEQ ID NO 1
<211> LENGTH: 1432
<212> TYPE: DNA
<213> ORGANISM: Alcaligenes faecalis

<400> SEQUENCE: 1

```
gctttaacac atgcaagtcg aacggcagca cgcagagagc ttgctctctt ggtggcgagt      60
ggcggacggg tgagtaatat atcggaacgt gcccagtagc gggggataac tactcgaaag     120
agtggctaat accgcatacg ccctacgggg gaaaggggggg gatcgcaaga cctctcacta    180
ttggagcggc cgatatcgga ttagctagtt ggtgggtaa aggctcacca aggcaacgat      240
ccgtagctgg tttgagagga cgaccagcca cactgggact gagacacggc ccagactcct    300
acgggaggca gcagtgggga attttggaca atgggggaaa ccctgatcca gccatcccgc    360
gtgtatgatg aaggccttcg ggttgtaaag tacttttggc agagaagaaa aggcatcccc    420
taatacggga tgctgctgac ggtatctgca gaataagcac cggctaacta cgtgccagca    480
gccgcggtaa tacgtagggt gcaagcgtta atcggaatta ctgggcgtaa agcgtgtgta    540
ggcggttcgg aaagaaagat gtgaaatccc agggctcaac cttggaactg cattttaac     600 tgccgagcta gagtatgtca gagggggggta gaattccacg tgtagcagtg aaatgcgtag    660
atatgtggag gaataccgat ggcgaaggca gccccctggg ataatactga cgctcagaca    720
cgaaagcgtg gggagcaaac aggattagat accctggtag tccacgccct aaacgatgtc    780
aactagctgt tggggccgtt aggccttagt agcgcagcta acgcgtgaag ttgaccgcct    840
ggggagtacg gtcgcaagat taaaactcaa aggaattgac ggggacccgc acaagcggtg    900
gatgatgtgg attaattcga tgcaacgcga aaaccttac ctaccttga catgtctgga     960 aagccgaaga gatttggcag tgctcgcaag agaaccggaa cacaggtgct gcatggctgt   1020
cgtcagctcg tgtcgtgaga tgttgggtta agtcccgcaa cgagcgcaac ccttgtcatt   1080
agttgctacg caagagcact ctaatgagac tgccggtgac aaaccggagg aaggtgggga   1140
tgacgtcaag tcctcatggc ccttatgggt agggcttcac acgtcataca atggtcggga   1200
cagagggtcg ccaacccgcg aggggagcc aatctcagaa acccgatcgt agtccggatc   1260
gcagtctgca actcgactgc gtgaagtcgg aatcgctagt aatcgcggat cagaatgtcg   1320
cggtgaatac gttcccgggt cttgtacaca ccgcccgtca caccatggga gtgggtttca   1380
ccagaagtag gtagcctaac cgcaaggagg gcgctaccac ggtgatgatg tc           1432
```

<210> SEQ ID NO 2
<211> LENGTH: 1412
<212> TYPE: DNA

<213> ORGANISM: Acetobacter peroxydans

<400> SEQUENCE: 2

```
agagtttgat catggctcag agcgaacgct ggcggcatgc ttaacacatg caagtcgcac      60
gaaggtttcg gccttagtgg cggacgggtg agtaacgcgt aggaatctat ccatgggtgg     120
gggataacac tgggaaactg gtgctaatac cgcatgacac ctgagggtca aggcgcaag     180
tcgcctgtgg aggagcctgc gttcgattag ctagttggtg gggtaaaggc ctaccaaggc     240
gatgatcgat agctggtttg agaggatgat cagccacact gggactgaga cacggcccag     300
actcctacgg gaggcagcag tggggaatat tggacaatgg gggcaaccct gatccagcaa     360
tgccgcgtgt gtgaagaagg tcttcggatt gtaaagcact ttcgacgggg acgatgatga     420
cggtacccgt agaagaagcc ccggctaact tcgtgccagc agccgcggta atacgaaggg     480
ggctagcgtt gctcggaatg actgggcgta aagggcgtgt aggcggtttt gacagtcaga     540
tgtgaaatcc ccgggcttaa cctgggagct gcatttgaga cgttaagact agagtgtgag     600
agagggttgt ggaattccca gtgtagaggt gaaattcgta gatattggga agaacaccgg     660
tggcgaaggc ggcaacctgg ctcattactg acgctgaggc gcgaaagcgt ggggagcaaa     720
caggattaga taccctggta gtccacgctg taaacgatgt gtgctagatg ttgggtaact     780
tagttactca gtgtcgcagt taacgcgtta agcacaccgc ctggggagta cggccgcaag     840
gttgaaactc aaaggaattg acgggggccc gcacaagcgg tggagcatgt ggtttaattc     900
gaagcaacgc gcagaacctt accagggctt gaatgtggag ctgtaggca gagatgtcta     960
tttcttcgga cctccaacac aggtgctgca tggctgtcgt cagctcgtgt cgtgagatgt    1020
tgggttaagt cccgcaacga gcgcaacccc tatctttagt tgccagcatg tttgggtggg    1080
cactctagag agactgccgg tgacaagccg gaggaaggtg gggatgacgt caagtcctca    1140
tggcccttat gtcctgggct acacacgtgc tacaatggcg gtgacagtgg gaagctatgt    1200
ggtgacacag tgctgatctc taaaagccgt ctcagttcgg attgcactct gcaactcgag    1260
tgcatgaagg tggaatcgct agtaatcgcg gatcagcatg ccgcggtgaa tacgttcccg    1320
ggccttgtac acaccgcccg tcacaccatg ggagtggttt gaccttaagc cggtgagcga    1380
accgcaagga cgcagccgac cacgtcgtcg ct                                   1412
```

<210> SEQ ID NO 3
<211> LENGTH: 1453
<212> TYPE: DNA
<213> ORGANISM: Lactobacillus fermentum

<400> SEQUENCE: 3

```
gcggctggct cctaaaaggt taccccaccg actttgggtg ttacaaactc tcatggtgtg      60
acgggcggtg tgtacaaggc ccgggaacgt attcaccgcg gcatgctgat ccgcgattac     120
tagcgattcc gacttcgtgc aggcgagttg cagcctgcag tccgaactga gaacggtttt     180
aagagatttg cttgccctcg cgagttcgcg actcgttgta ccgtccattg tagcacgtgt     240
gtagcccagg tcataagggg catgatgatc tgacgtcgtc cccaccttcc tccggtttgt     300
caccggcagt ctcactagag tgcccaactt aatgctggca actagtaaca agggttgcgc     360
tcgttgcggg acttaaccca acatctcacg acacgagctg acgacgacca tgcaccacct     420
gtcattgcgt tcccgaagga aacgccctat ctctagggtt ggcgcaagat gtcaagacct     480
ggtaaggttc ttcgcgtagc ttcgaattaa accacatgct ccaccgcttg tgcgggcccc     540
cgtcaattcc tttgagtttc aaccttgcgg tcgtactccc caggcggagt gcttaatgcg     600
```

-continued

```
ttagctccgg cactgaaggg cggaaaccct ccaacaccta gcactcatcg tttacggcat      660
ggactaccag ggtatctaat cctgttcgct acccatgctt tcgagtctca gcgtcagttg      720
cagaccaggt agccgccttc gccactggtg ttcttccata tatctacgca ttccaccgct      780
acacatggag ttccactacc ctcttctgca ctcaagttat ccagtttccg atgcacttct      840
ccggttaagc cgaaggcttt cacatcagac ttagaaaacc gcctgcactc tctttacgcc      900
caataaatcc ggataacgct tgccacctac gtattaccgc ggctgctggc acgtagttag      960
ccgtgacttt ctggttaaat accgtcaacg tatgaacagt tactctcata cgtgttcttc     1020
tttaacaaca gagctttacg agccgaaacc cttcttcact cacgcggtgt tgctccatca     1080
ggcttgcgcc cattgtggaa gattccctac tgctgcctcc cgtaggagta tgggccgtgt     1140
ctcagtccca ttgtggccga tcagtctctc aactcggcta tgcatcatcg ccttggtagg     1200
ccgttacccc accaacaagc taatgcaccg caggtccatc cagaagtgat agcgagaagc     1260
catcttttaa gcgttgttca tgcgaacaac gctgttatgc ggtattagca tctgtttcca     1320
aatgttgtcc cccgcttctg ggcaggttac ctacgtgtta ctcacccgtc cgccactcgt     1380
tggcgaccaa aatcaatcag gtgcaagcac catcaatcaa ttgggccaac gcgttcgact     1440
gcattattag gca                                                        1453
```

<210> SEQ ID NO 4
<211> LENGTH: 1439
<212> TYPE: DNA
<213> ORGANISM: Bacillus subtilis

<400> SEQUENCE: 4

```
ctatacatgc aagtcgagcg gacagatggg agcttgctcc ctgatgttag cggcggacgg       60
gtgagtaaca cgtgggtaac ctgcctgtaa gactgggata actccgggaa accggggcta      120
ataccggatg gttgtttgaa ccgcatggtt cagacataaa aggtggcttc ggctaccact      180
tacagatgga cccgcggcgc attagctagt tggtgaggta acggctcacc aaggcgacga      240
tgcgtagccg acctgagagg gtgatcggcc acactgggac tgagacacgg cccagactcc      300
tacgggaggc agcagtaggg aatcttccgc aatggacgaa agtctgacgg agcaacgccg      360
cgtgagtgat gaaggttttc ggatcgtaaa gctctgttgt tagggaagaa caagtgccgt      420
tcaaataggg cggcaccttg acggtaccta accagaaagc cacggctaac tacgtgccag      480
cagccgcggt aatacgtagg tggcaagcgt tgtccggaat tattgggcgt aaagggctcg      540
caggcggttt cttaagtctg atgtgaaagc ccccggctca accggggagg gtcattggaa      600
actggggaac ttgagtgcag aagaggagag tggaattcca cgtgtagcgg tgaaatgcgt      660
agagatgtgg aggaacacca gtggcgaagg cgactctctg gtctgtaact gacgctgagg      720
agcgaaagcg tggggagcga acaggattag ataccctggt agtccacgcc gtaaacgatg      780
agtgctaagt gttaggggg ttccgccct tagtgctgca gctaacgcat taagcactcc      840
gcctggggag tacggtcgca agactgaaac tcaaaggaat tgacggggc cgcacaagc      900
ggtggagcat gtggtttaat tcgaagcaac gcgaagaacc ttaccaggtc ttgacatcct      960
ctgacaatcc tagagatagg acgtcccctt cgggggcaga gtgacaggtg gtgcatggtt     1020
gtcgtcagct cgtgtcgtga gatgttgggt taagtcccgc aacgagcgca accccttgatc     1080
ttagttgcca gcattcagtt gggcactcta aggtgactgc cggtgacaaa ccggaggaag     1140
gtggggatga cgtcaaatca tcatgcccct tatgacctgg gctacacacg tgctacaatg     1200
```

-continued

| | |
|---|---|
| ggcagaacaa agggcagcga aaccgcgagg ttaagccaat cccacaaatc tgttctcagt | 1260 |
| tcggatcgca gtctgcaact cgactgcgtg aagctggaat cgctagtaat cgcggatcag | 1320 |
| catgccgcgg tgaatacgtt cccgggcctt gtacacaccg cccgtcacac cacgagagtt | 1380 |
| tgtaacaccc gaagtcggtg aggtaacctt ttaggagcca gccgccgaag gttggacag | 1439 |

<210> SEQ ID NO 5
<211> LENGTH: 1430
<212> TYPE: DNA
<213> ORGANISM: Kurthia gibsonii

<400> SEQUENCE: 5

| | |
|---|---|
| ctatacatgc agtcgagcga atgacgagaa gcttgcttct ctgatttagc ggcggacggg | 60 |
| tgagtaacac gtgggcaacc tgccctacag atcgggataa ctcagggaaa cctgggctaa | 120 |
| taccggataa tccttcgaat cacatgtttt gaagttgaaa ggcgcttcgg cgtcactgta | 180 |
| ggatgggccc gcggtgcatt agctagttgg tggggtaacg gcctaccaag caacgatgc | 240 |
| atagccgacc tgagagggtg atcggccaca ttggactga gacacggccc aaactcctac | 300 |
| gggaggcagc agtagggaat cttccacaat ggacgaaagt ctgatggagc aacgccgcgt | 360 |
| gagtgatgaa ggttttcgga tcgtaaaact ctgttgtaag gaagaacaa gtacgttagg | 420 |
| aaatgaacgt accttgacgg taccttatta gaaagccacg gctaactacg tgccagcagc | 480 |
| cgcggtaata cgtaggtggc aagcgttgtc cggatttatt gggcgtaaag cgcgcgcagg | 540 |
| tggtttctta gtctgatgt gaaagcccac ggctcaaccg tggagggtca ttggaaactg | 600 |
| gggaacttga gtgcagaaga ggatagtgga attccaagtg tagcggtgaa atgcgtagag | 660 |
| atttggagga acaccagtgg cgaaggcgac tgtctggtct gtaactgaca ctgaggcgcg | 720 |
| aaagcgtggg gagcaaacag gattagatac cctggtagtc cacgccgtaa cgatgagtg | 780 |
| ctaagtgtta gggggtttcc gccccttagt gctgcagcta acgcattaag cactccgcct | 840 |
| ggggagtacg accgcaaggt tgaaactcaa aggaattgac gggggcccgc acaagcggtg | 900 |
| gagcatgtgg tttaattcga agcaacgcga agaaccttac caggtcttga catcccaatg | 960 |
| accgtcctag agataggatt ttcccttcgg ggacattggt gacaggtggt gcatggttgt | 1020 |
| cgtcagctcg tgtcgtgaga tgttgggtta agtcccgcaa cgagcgcaac ccttattctt | 1080 |
| agttgccatc atttagttgg gcactctaag gagactgccg gtgacaaacc ggaggaaggt | 1140 |
| ggggatgacg tcaaatcatc atgccccctta tgacctgggc tacacacgtg ctacaatgga | 1200 |
| cgatacaaag agtcgcaaac tcgcgagggt aagctaatct cataaaatcg ttctcagttc | 1260 |
| ggattgtagg ctgcaactcg cctgcatgaa gccggaatcg ctagtaatcg cggatcagca | 1320 |
| tgccgcggtg aatacgttcc cgggccttgt acacaccgcc cgtcacacca cgagagtttg | 1380 |
| taacacccga gtcggtggg gtaaccgtaa ggagccagcc gctaagtgaa | 1430 |

<210> SEQ ID NO 6
<211> LENGTH: 1432
<212> TYPE: DNA
<213> ORGANISM: Clostridium acidisoli

<400> SEQUENCE: 6

| | |
|---|---|
| agagtttgat catggctcag gacgaacgct ggcggcgtgc ttaacacatg caagtcgagc | 60 |
| gagaaaccct cgggtttcta gcggcggacg ggtgagtaac acgtgggtaa cctgcctcaa | 120 |
| agtgggggat agccttccga aaggaagatt aataccgcat aacattgtag cttcgcatga | 180 |
| agcaacaatt aaaggagtaa tccgctttga gatggacccg cggcgcatta gctagttgga | 240 |

-continued

```
gaggtaacgg ctcaccaagg cgacgatgcg tagccgacct gagagggtga tcggccacat    300
tggaactgag acacggtcca gactcctacg ggaggcagca gtggggaata ttgcacaatg    360
ggcgaaagcc tgatgcagca acgccgcgtg agtgatgaag gtcttcggat tgtaaagctc    420
tgtcttttgg gacgataatg acggtaccaa aggaggaagc cacggctaac tacgtgccag    480
cagccgcggt aatacgtagg tggcaagcgt tgtccggaat tactgggcgt aaaggatgtg    540
taggcggata tttaagtgag atgtgaaatc cccgagctca acttggggc tgcatttcaa     600 actgggtatc tagagtgcag gagaggaaag cggaattcct agtgtagcgg tgaaatgcgt    660
agagattagg aagaacatca gtggcgaagg cggctttctg gactgtaact gacgctgagg    720
catgaaagcg tggggagcaa acaggattag ataccctggt agtccacgcc gtaaacgatg    780
agtactaggt gtaggaggta tcgactcctt ctgtgccgca gttaacacaa taagtactcc    840
gcctgggaag tacggtcgca agattaaaac tcaaaggaat tgacggggc cgcacaagc     900 agcggagcat gtggtttaat tcgaagcaac gcgaagaacc ttacctagac ttgacatccc    960
ctgaataacg tagagatacg aagcccctt cggggcaggg agacaggtgg tgcatggttg    1020
tcgtcagctc gtgtcgtgag atgttgggtt aagtcccgca acgagcgcaa cccttatcat   1080
tagttgctac catttagttg agcactctag tgagactgcc cgggttaacc gggaggaagg   1140
cggggatgac gtcaaatcat catgccccctt atgtctaggg ctacacacgt gctacaatgg   1200
tgagaacaac gagatgcaat accgcgaggt ggagcaaaac ttcaaaactc atctcagttc   1260
ggattgtagg ctgaaactcg cctacatgaa gttggagttg ctagtaatcg cgaatcagaa   1320
tgtcgcggtg aatacgttcc cgggccttgt acacaccgcc cgtcacacca tgagagctgg   1380
taacacccga agtccgtgag gtaacctta ttggggccag cggccgaagg tg            1432
```

<210> SEQ ID NO 7
<211> LENGTH: 1438
<212> TYPE: DNA
<213> ORGANISM: Enterococcus faecium

<400> SEQUENCE: 7

```
gcggctggct ccaaaaggtt acctcaccga cttcgggtgt tacaaactct cgtggtgtga     60
cgggcggtgt gtacaaggcc cgggaacgta ttcaccgcgg cgtgctgatc cgcgattact    120
agcgattccg gcttcatgca ggcgagttgc agcctgcaat ccgaactgag agaagcttta    180
agagattagc ttagcctcgc gacttcgcaa ctcgttgtac ttcccattgt agcacgtgtg    240
tagcccaggt cataaggggc atgatgattt gacgtcatcc ccaccttcct ccggtttgtc    300
accggcagtc ttgctagagt gcccaactga atgatggcaa ctaacaataa gggttgcgct    360
cgttgcggga cttaacccaa catctcacga cacgagctga cgacaaccat gcaccacctg    420
tcactttgcc cccgaagggg aagctctatc tctagagtgg tcaaaggatg tcaagacctg    480
gtaaggttct tcgcgttgct tcgaattaaa ccacatgctc caccgcttgt gcgggccccc    540
gtcaattcct ttgagtttca accttgcggt cgtactcccc aggcggagtg cttaatgcgt    600
tagctgcagc actgaagggc ggaaacccctc caacacttag cactcatcgt ttacggcgtg    660
gactaccagg gtatctaatc ctgtttgctc cccacgcttt cgagcctcag cgtcagttac    720
agaccagaga gccgccttcg ccactggtgt tcctccatat atctacgcat ttcaccgcta    780
cacatggaat tccactctcc tcttctgcac tcaagtctcc cagtttccaa tgaccctccc    840
cggttgagcc ggggggcttc acatcagact taagaaaccg cctgcgctcg ctttacgccc    900
```

```
aataaatccg acaacgcttg ccacctacg tattaccgcg gctgctggca cgtagttagc    960
cgtggctttc tggttagata ccgtcaaggg atgaacagtt actctcatcc ttgttcttct   1020
ctaacaacag agttttacga tccgaaaacc ttcttcactc acgcggcgtt gctcggtcag   1080
actttcgtcc attgccgaag attccctact gctgcctccc gtaggagttt gggccgtgtc   1140
tcagtcccaa tgtggccgat caccctctca ggtcggctat gcatcgtggc cttggtgagc   1200
cgttacctca ccaactagct aatgcaccgc gggtccatcc atcagcgaca cccgaaagcg   1260
cctttcaaat caaaaccatg cggttttgat tgttatacgg tattagcacc tgtttccaag   1320
tgttatcccc ttctgatggg caggttaccc acgtgttact cacccgttcg ccactcctct   1380 tttccggtg gagcaagctc cggtggaaaa agaagcgtgc gacttgcacg tattaggc     1438
```

```
<210> SEQ ID NO 8
<211> LENGTH: 1487
<212> TYPE: DNA
<213> ORGANISM: Enterococcus azikeevi

<400> SEQUENCE: 8
agagtttgaa tcatggctca ggacgaacgc tggcggcgtg cctaatacat gcaagtcgaa     60
cgcttctttt tccaccggag cttgctccac cggaaaaaga ggagtggcga acgggtgagt    120
aacacgtggg taacctgccc atcagaaggg ataacactt ggaaacaggt gctaataccg     180
tataacaatc gaaaccgcat ggttttgatt tgaaaggcgc tttcgggtgt cgctgatgga    240
tggacccgcg gtgcattagc tagttggtga ggtaacggct caccaaggcg acgatgcata    300
gccgacctga gagggtgatc ggccacattg gactgagac acggcccaaa ctcctacggg    360
aggcagcagt agggaatctt cggcaatgga cgaaagtctg accgagcaac gccgcgtgag    420
tgaagaaggt tttcggatcg taaaactctg ttgttagaga agaacaagga tgagagtaac    480
tgttcatccc ttgacggtat ctaaccagaa agccacggct aactacgtgc cagcagccgc    540
ggtaatacgt aggtggcaag cgttgtccgg atttattggg cgtaaagcga gcgcaggcgg    600
tttcttaagt ctgatgtgaa agccccggc tcaaccgggg agggtcattg gaaactggga    660
gacttgagtg cagaagagga gagtggaatt ccatgtgtag cggtgaaatg cgtagatata    720
tggaggaaca ccagtggcga aggcggctct ctggtctgta actgacgctg aggctcgaaa    780
gcgtggggag caaacaggat tagataccct ggtagtccac gccgtaaacg atgagtgcta    840
agtgttggag ggtttccgcc cttcagtgct gcagctaacg cattaagcac tccgcctggg    900
gagtacgacc gcaaggttga aactcaaagg aattgacggg ggcccgcaca agcggtggag    960
catgtggttt aattcgaagc aacgcgaaga accttaccag gtcttgacat cctttgacca   1020
ctctagagat agagcttccc cttcgggggc aaagtgacag gtggtgcatg gttgtcgtca   1080
gctcgtgtcg tgagatgttg ggttaagtcc cgcaacgagc gcaaccctta ttgttagttg   1140
ccatcattta gttgggcact ctagcaagac tgccggtgac aaaccggagg aaggtgggga   1200
tgacgtcaaa tcatcatgcc ccttatgacc tgggctacac acgtgctaca atggaagta    1260 caacgagtcg caaagtcgcg aggctaagct aatctcttaa agcttctctc agttcggatt   1320
gtaggctgca actcgcctac atgaagccgg aatcgctagt aatcgcggat cagcacgccg   1380
cggtgaatac gttcccgggc cttgtacaca ccgcccgtca caccacgaga gtttgtaaca   1440
cccgaagtcg gtgaggtaac cttttggagc cagccgccta aggtgat                1487
```

```
<210> SEQ ID NO 9
<211> LENGTH: 1429
```

```
<212> TYPE: DNA
<213> ORGANISM: Enterobacter roggenkampii

<400> SEQUENCE: 9
gcagctacac atgcaagtcg agcggcagcg gaagtagctt gctactttgc cggcgagcgg    60
cggacgggtg agtaatgtct gggaaactgc ctgatggagg gggataacta ctggaaacgg   120
tagctaatac cgcataacgt cgcaagacca agagggggga ccttcgggcc tcttgccatc   180
agatgtgccc agatgggatt agctagtagg tggggtaacg gctcacctag gcgacgatcc   240
ctagctggtc tgagaggatg accagccaca ctggaactga dacacggtcc agactcctac   300
gggaggcagc agtggggaat attgcacaat gggcgcaagc ctgatgcagc catgccgcgt   360
gtatgaagaa ggccttcggg ttgtaaagta ctttcagcgg ggaggaaggc gttgaggtta   420
ataacctcag cgattgacgt tacccgcaga agaagcaccg gctaactccg tgccagcagc   480
cgcggtaata cggagggtgc aagcgttaat cggaattact gggcgtaaag cgcacgcagg   540
cggtctgtca agtcgatgt gaaatccccg gctcaacct gggaactgca ttcgaaactg   600
gcaggctaga gtcttgtaga ggggggtaga attccaggtg tagcggtgaa atgcgtagag   660
atctggagga ataccggtgg cgaaggcggc cccctggaca aagactgacg ctcaggtgcg   720
aaagcgtggg gagcaaacag gattagatac cctggtagtc cacgccgtaa acgatgtcga   780
cttggaggtt gtgcccttga ggcgtggctt ccggagctaa cgcgttaagt cgaccgcctg   840
gggagtacgg ccgcaaggtt aaaactcaaa tgaattgacg ggggcccgca caagcggtgg   900
agcatgtggt ttaattcgat gcaacgcgaa gaaccttacc tactcttgac atccagagaa   960
cttagcagag atgctttggt gccttcggga actctgagac aggtgctgca tggctgtcgt  1020
cagctcgtgt tgtgaaatgt tgggttaagt cccgcaacga gcgcaaccct tatccttttgt  1080 tgccagcggt ccggccggga actcaaagga gactgccagt gataaactgg aggaaggtgg  1140
ggatgacgtc aagtcatcat ggcccttacg agtagggcta cacacgtgct acaatggcgc  1200
atacaaagag aagcgaccctc gcgagagcaa gcggacctca taagtgcgt cgtagtccgg   1260 attggagtct gcaactcgac tccatgaagt cggaatcgct agtaatcgta gatcagaatg   1320
ctacggtgaa tacgttcccg ggccttgtac acaccgcccg tcacaccatg ggagtgggtt   1380
gcaaaagaag taggtagctt aaccttcggg agggcgctac cacttgatt              1429

<210> SEQ ID NO 10
<211> LENGTH: 1401
<212> TYPE: DNA
<213> ORGANISM: Clostridium kogasensis

<400> SEQUENCE: 10
cggcagctac acatgcaagt cgagcgatga aatcccttcg gggatggatt agcggcggac    60
gggtgagtaa cacgtgggca acctgcctca aagtggggga tagcctcccg aaagggagat   120
taataccgca taatgttaga tcttcacatg aagaactaat aaaggagca atccgctttg   180 agatgggccc gcggcgcatt agctagttgg tgaggtaatg gctcaccaag gcgacgatgc   240
gtagccgacc tgagagggtg atcggccaca ttggaactga dacacggtcc agactcctac   300
gggaggcagc agtggggaat attgcacaat ggggaaacc ctgatgcagc aacgccgcgt   360
gagtgatgaa ggtcttcgga ttgtaaagct ctgtcttttg gacgataat gacggtacca   420 aaggaggaag ccacggctaa ctacgtgcca gcagccgcgg taatacgtag gtggcgagcg   480
ttgtccggat ttactgggcg taagggtgc gtaggcggat atttaagtgg gatgtgaaat   540
```

-continued

```
acccgggctc aacttgggtg ctgcattcca aactggatat ctagagtgcg ggagaggaga      600
gtggaattcc tagtgtagcg gtgaaatgcg tagagattag gaagaacacc agtggcgaag      660
gcgactctct ggaccgtaac tgacgctgag gcacgaaagc gtggggagca aacaggatta      720 gatacccctgg tagtccacgc cgtaaacgat gaatactagg tgtaggaggt atcgacccct     780
tctgtgccgc agttaacaca ataagtattc cgcctgggga gtacggtcgc aagattaaaa      840
ctcaaaggaa ttgacggggg cccgcacaag cagcggagca tgtggtttaa ttcgaagcaa      900
cgcgaagaac cttacctaga cttgacatac cctgaattac cggtaatgcg ggaagccctt      960
cggggcaggg atacaggtgg tgcatggttg tcgtcagctc gtgtcgtgag atgttaggtt     1020
aagtcctgca acgagcgcaa cccctattat tagttgctac cattaagttg agcactctag    1080
taagactgcc tgggttaacc aggaggaagg cggggatgac gtcaaatcat catgcccctt    1140
atgtctaggg ctacacacgt gctacaatgg gcggtacaaa aagatgcaaa ctcgcgagag    1200
tgagccaaac tttaaaaccg cccccagttc ggattgtagg ctgaaactcg cctacatgaa    1260
gccggagttg ctagtaatcg cgaatcagca tgtcgcggtg aatacgttcc cgggccttgt    1320
acacaccgcc cgtcacacca tgagagctgg caacacccga agtccgtgag gtaaccgtaa    1380
ggagccagcg gccgaagtgg g                                               1401
```

STERILIZATION EXHAUST GAS TREATING SYSTEM AND METHOD FOR TREATING ETHYLENE OXIDE-CONTAINING STERILIZATION EXHAUST GAS BY USING THE SAME

CROSS-REFERENCE TO RELATED PATENT APPLICATIONS

This application is a Bypass Continuation of PCT/CN2020/101140, filed Jul. 9, 2020, which application claims the benefit of Chinese Patent Application No. 202010194457.6 filed on 19 Mar. 2020, Chinese Patent Application No. 202010190366.5 filed on 18 Mar. 2020, Chinese Patent Application No. 202010194449.1 filed on 19 Mar. 2020, Chinese Patent Application No. 202010190385.8 filed on 18 Mar. 2020, Chinese Patent Application No. 202010190355.7 filed on 18 Mar. 2020, and Chinese Patent Application No. 202010190370.1 filed on 18 Mar. 2020, the entire contents of which are incorporated herein by reference in their entirety for all purposes.

TECHNICAL FIELD

The present disclosure relates to the technical field of sterilization technology, in particular, to a sterilization exhaust gas treatment system and a method for treating ethylene oxide-containing sterilization exhaust gas by using the sterilization exhaust gas treatment system.

SEQUENCE STATEMENT

Incorporated by reference herein in its entirety is the Sequence Listing entitled "1211_CK06_ST25_WO" created Jul. 6, 2020, size of 19.8 kilobytes.

BACKGROUND

Ethylene oxide ("EO") is a broad-spectrum, high-efficiency sterilizing agent with excellent sterilization performance. EO has strong penetrating power, can kill various microorganisms at normal temperature, and does not damage the sterilized items during sterilization. Currently, the ethylene oxide gas sterilization method is one of the most important low-temperature sterilization methods, and is especially most commonly used in hospitals.

However, the ethylene oxide itself is toxic, flammable, and explosive. After sterilization with the ethylene oxide gas, the sterilization exhaust gas that is generated in the sterilizer needs to receive a harmless gas treatment before being discharged. At present, the methods of treating the ethylene oxide-containing sterilization exhaust gas include: (1) the Catalytic combustion method; (2) the Absorption method; and (3) the Low temperature recovery method. For (1) the Catalytic combustion method, the sterilization exhaust gas is converted to a non-toxic substance by catalytic combustion. However, since ethylene oxide is flammable and explosive, this method poses potential safety hazards during the treatment of the sterilization exhaust gas. For (2) the Absorption method, the sterilization exhaust gas generates ethylene glycol by acid catalysis, and this method is suitable for the treatment of the high-concentration ethylene oxide exhaust gas. However, if the treatment operation is improperly performed, it may result in secondary pollution or contamination. For (3) the Low temperature recovery method, the sterilization exhaust gas is condensed at $-29°$ C. to recover the ethylene oxide. However, this method requires high energy consumption and is very high in terms of equipment requirements.

Hence, there may be a need for more robust and scalable solutions for implementing sterilization technologies, and, more particularly, for implementing a sterilization exhaust gas treatment system and a method for treating ethylene oxide-containing sterilization exhaust gas by using the sterilization exhaust gas treatment system.

SUMMARY

In one aspect, a sterilization exhaust gas treatment system is provided. The system may include a gas liquefaction recovery system, a pressure swing adsorption recovery system, a reaction system, a temperature swing adsorption recovery system, a hydration system, a recovery and storage system, and a wastewater treatment system. According to some embodiments, the gas liquefaction recovery system, the pressure swing adsorption recovery system, the reaction system, the temperature swing adsorption recovery system, and the hydration system may be fluidly connected in sequence through one or more first connecting pipes. The gas liquefaction recovery system, the pressure swing adsorption recovery system, and the temperature swing adsorption recovery system may each be fluidly connected to the recovery and storage system through one or more second connecting pipes. The hydration system may be fluidly connected to the wastewater treatment system through one or more wastewater pipes.

In another aspect, a method for treating ethylene oxide-containing sterilization exhaust gas using the sterilization exhaust gas treatment system as described above is provided. The method may include: S1, passing the ethylene oxide-containing sterilization exhaust gas into the gas liquefaction recovery system, pressurizing the gas liquefaction recovery system, so that ethylene oxide in the ethylene oxide-containing sterilization exhaust gas may be compressed and liquefied to obtain ethylene oxide liquid and treated exhaust gas, and then recovering the ethylene oxide liquid and directing the received ethylene oxide liquid to the recovery and storage system; S2, passing the exhaust gas treated by the gas liquefaction recovery system into the pressure swing adsorption recovery system to perform pressurized adsorption and depressurized desorption, and recovering ethylene oxide gas that may be obtained by the depressurized desorption and directing the recovered ethylene oxide gas to the recovery and storage system; S3, passing the exhaust gas treated by the pressure swing adsorption recovery system into the reaction system to acidize the ethylene oxide in the exhaust gas; S4, passing the exhaust gas treated by the reaction system into the temperature swing adsorption recovery system for low-temperature adsorption and high-temperature desorption, and recovering the desorbed ethylene oxide gas and directing the recovered desorbed ethylene oxide gas to the recovery and storage system; S5, passing the exhaust gas treated by the temperature swing adsorption recovery system into the hydration system, so that the ethylene oxide in the exhaust gas may be treated by water absorption to obtain wastewater containing ethylene oxide; and S6, inputting the wastewater containing the ethylene oxide that may be obtained by the hydration system into the wastewater treatment system.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF THE EMBODIMENTS

Exemplary embodiments will be described hereafter with reference to the drawings to clearly and fully illustrate the technical solutions of the present disclosure. All other embodiments obtained by a person of ordinary skill in the art based on the embodiments in the present disclosure without creative efforts are within the scope of the present disclosure.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Figure 1:
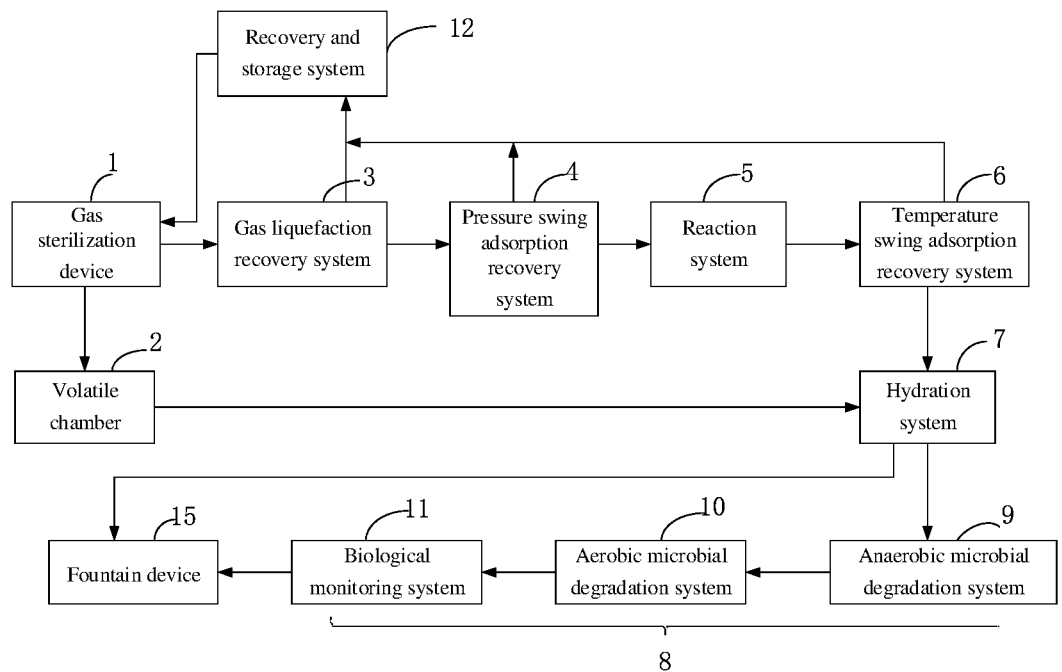
FIG. 1 is a schematic system block diagram illustrating a sterilization exhaust gas treatment system according to an embodiment of the present disclosure.
Figure 2:
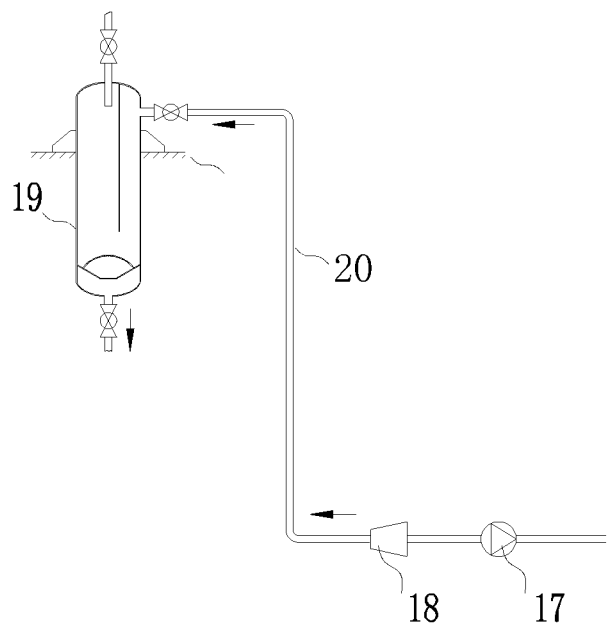
FIG. 2 is a schematic diagram illustrating a gas liquefaction recovery system according to an embodiment of the present disclosure.
Figure 3A:
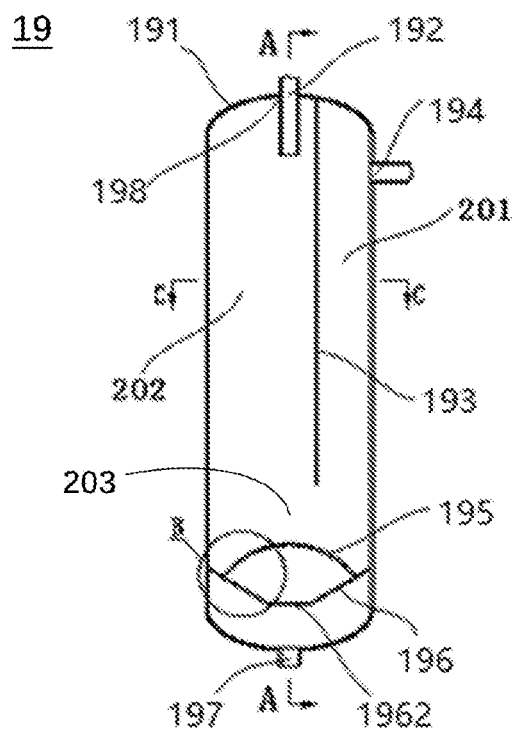
FIG. 3A is a schematic diagram illustrating a gas liquefaction separator according to an embodiment of the present disclosure.
Figure 3B:
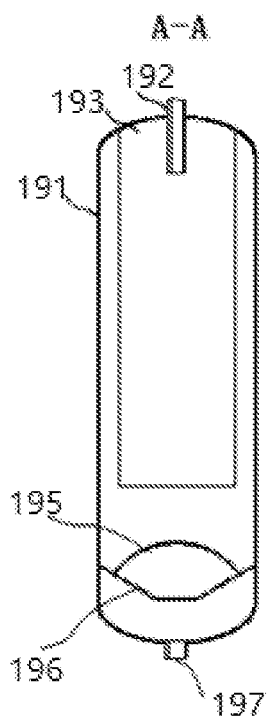
FIG. 3B is a schematic diagram illustrating a cross-sectional view of the gas liquefaction separator of FIG. 3A taken along line A-A of FIG. 3A.
Figure 3C:
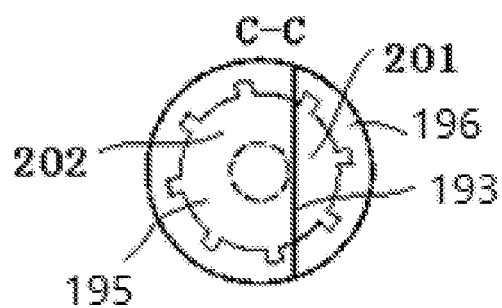
FIG. 3C is a schematic diagram illustrating a cross-sectional view of the gas liquefaction separator of FIG. 3A taken along line C-C of FIG. 3A.

As shown in FIG. 1, an embodiment of the present disclosure discloses a sterilization exhaust gas treatment system, which may include, but is not limited to, a gas liquefaction recovery system 3, a pressure swing adsorption ("PSA") recovery system 4, a reaction system 5, a temperature swing adsorption ("TSA") recovery system 6, a hydration system 7, a recovery and storage system 12, and a wastewater treatment system 8. The gas liquefaction recovery system 3, the PSA recovery system 4, the reaction system 5, the TSA recovery system 6, and the hydration system 7 may be fluidly connected in sequence through one or more first connecting pipes. The gas liquefaction recovery system 3, the PSA recovery system 4, and the TSA recovery system 6 may each be fluidly connected to the recovery and storage system 12 through one or more second connecting pipes. The hydration system 7 may be fluidly connected to the wastewater treatment system 8 through one or more wastewater pipes.

According to some embodiments, the wastewater treatment system 8 may include an anaerobic microbial degradation system 9, an aerobic microbial degradation system 10, and a biological monitoring system 11. The hydration system 7 may be fluidly connected to the anaerobic microbial degradation system 9, the aerobic microbial degradation system 10, and the biological monitoring system 11 in sequence through the one or more wastewater pipes.

In some embodiments, the sterilization exhaust gas treatment system may further include a gas sterilization device 1, and the gas liquefaction recovery system 3 may be fluidly connected to the gas sterilization device 1 through a gas sterilization pipe.

According to some embodiments, the recovery and storage system 12 may be also fluidly connected to the gas sterilization device 1 through one or more pipes.

In some embodiments, the wastewater treatment system 8 may further include a volatile chamber 2. The gas sterilization device 1 may be fluidly connected to the hydration system 7 through the volatile chamber 2.

According to some embodiments, the sterilization exhaust gas treatment system may further include a fountain device 15. The hydration system 7 and the wastewater treatment system 8 may each also be fluidly connected to the fountain device 15 through one or more fountain connection pipes.

In an embodiment, the gas sterilization device 1 may be an ethylene oxide gas sterilization device.

When the sterilization exhaust gas treatment system of the embodiment of the present disclosure is used to treat ethylene oxide-containing sterilization exhaust gas, the ethylene oxide may be compressed by the gas liquefaction recovery system 3 and may be liquefied and then recovered, so that the recovered ethylene oxide has high purity, with high recovery rate. Depending on the principle of pressure swing adsorption of the PSA recovery system 4, the difference in the adsorption performance of the adsorbing materials for different gases, and the different characteristics of the adsorbing amount of the adsorbed gas under different pressures, an adsorbing operation cycle may be formed by the combination of pressurized adsorption and depressurized desorption, so that the ethylene oxide in the ethylene oxide-containing sterilization exhaust gas may be separated to further improve the recovery rate. The ethylene oxide contained in the sterilization exhaust gas may be further adsorbed by the TSA recovery system 6, and the desorbed ethylene oxide may be recovered, so as to improve the recovery rate of ethylene oxide as much as possible. Then, in conjunction with the reaction system 5, the hydration system 7, and the wastewater treatment system 8, the residual ethylene oxide may be harmlessly treated, so that the resultant or treated sterilization exhaust gas achieves or satisfies the applicable emission standards, resulting in no secondary pollution or contamination being generated due to discharge of the resultant or treated sterilization exhaust gas into the outside environment.

As shown in FIGS. 2 to 6, in an embodiment, the gas liquefaction recovery system 3 may include a gas liquefaction separator 19, a gas extraction device 17, a pressurizing device 18, and a gas intake pipe 20. The gas liquefaction separator 19 may include a housing 191, a blocking plate 193, a gas baffle 195, and a liquid collector 196.

The housing 191 may include a gas outlet 198, a gas inlet 194, and a liquid outlet 197. The gas inlet 194 may be fluidly connected to the gas intake pipe 20. The gas intake pipe 20 may be configured to introduce the sterilization exhaust gas into the gas liquefaction separator 19. In an embodiment, the gas intake pipe 20 may be fluidly connected to the gas sterilization device 1. The gas outlet 198 may be fluidly connected to the PSA recovery system 4 through one of the one or more first connecting pipes. The remaining exhaust gas of the sterilization exhaust gas that may be separated by the gas liquefaction separator 19 may enter the PSA recovery system 4 through the gas outlet 198 for further treatment. The liquid outlet 197 may be fluidly connected to the recovery and storage system 12 through one of the one or more second connecting pipes. The liquid generated by compressing and liquefying the sterilization exhaust gas in the gas liquefaction separator 19 may enter the recovery and storage system 12. The pressurizing device 18 and the gas extraction device 17 may be provided on the gas intake pipe 20. The gas extraction device 17 may be configured to drive the sterilization exhaust gas into the gas liquefaction separator 19 through the gas intake pipe 20. The gas extraction device 17 may be a vacuum pump, or the like. The pressurizing device 18 may be configured to increase the gas pressure in the gas liquefaction separator 19. The pressurizing device 18 may be provided downstream of the gas extraction device 17. The pressurizing device 18 may include, for example, a booster pump, or the like.

The housing 191 may include, for example, a vertical cylindrical tank, or the like. The gas outlet 198 may be disposed on or at a top portion of the housing 191. The gas inlet 194 may be disposed at an inner side wall of the housing 191, and, in some cases, may be located on an upper portion of a side wall of the housing 191 and may be disposed adjacent to the top portion of the housing 191. The liquid outlet 197 may be disposed on a bottom portion of the housing 191. The gas inlet 194 may be configured to input gas to be separated, for example, ethylene oxide-containing sterilization exhaust gas, or the like. The gas liquefaction separator 19 can be used to separate a liquid ethylene oxide from the sterilization exhaust gas, and the separated liquid ethylene oxide may be discharged from the liquid outlet 197, and then input into the recovery and storage system 12. It can be understood that the gas to be separated is not limited to ethylene oxide gas sterilization exhaust gas, and the gas liquefaction separator 19 can also be used for separation and recover of other gases containing ethylene oxide or used for the separation and recovery of other gases with properties similar to those of the ethylene oxide.

The blocking plate 193, the gas baffle 195, and the liquid collector 196 may be disposed inside the housing 191. The gas baffle 195 may be located below the blocking plate 193, and the liquid collector 196 may be located below the gas baffle 195. The blocking plate 193 may extend downward from a top wall of an inner cavity of the housing 191 and may divide the inner cavity of the housing 191 into an upstream chamber 201, a downstream chamber 202, and a lower chamber 203. The upstream chamber 201 and the downstream chamber 202 may be separated by the blocking plate 193, and the lower chamber 203 may be located below the blocking plate 193. A bottom portion of the upstream chamber 201 and a bottom portion of the downstream chamber 202 may be in fluid communication with each other through the lower chamber 203. The gas outlet 198 may correspond to the downstream chamber 202, while the gas inlet 194 may correspond to the upstream chamber 201 and may be opposed to the blocking plate 193. The liquid outlet 197 may correspond to the lower chamber 203. The blocking plate 193 may be configured to block the gas to be separated that enters through the gas inlet 194 to prevent the gas to be separated from being directly discharged from the housing 191 through the gas outlet 198.

A liquid substance that may be formed from the gas to be separated in the gas liquefaction separator 19, such as liquid ethylene oxide, tends to adhere to the blocking plate 193, and then may condense together and may flow downward along the blocking plate 193, so as to fall from a lower edge of the blocking plate 193, which is beneficial to the recovery of liquid substances, such as the liquid ethylene oxide. In addition, providing the blocking plate 193 can increase the time period that the gas to be separated stays in the gas liquefaction separator 19, which is beneficial to the further liquefaction of the gas to be separated and the improvement of the compressing and recovery rate. Moreover, the blocking plate 193 can also prevent the liquefied ethylene oxide from being re-vaporized due to excessive gas flow. Meanwhile, liquid drops on the blocking plate 193 may condense and flow downward, which is beneficial to the liquefaction of ethylene oxide. In an embodiment, the blocking plate 193 may be deviated, or displaced, laterally from the longitudinal axis of the housing 191. As a result, the size of the downstream chamber 202 may be larger than the size of the upstream chamber 201. The gas inlet 194 is disposed on the inner side wall of the housing 191 that is adjacent to the blocking plate 193.

Furthermore, the gas inlet 194 may be located on a side wall of the housing 191, and an axis of the gas inlet 194 may be perpendicular to a longitudinal axis of the housing 191. In an embodiment, the blocking plate 193 may be a flat plate and may be parallel to the longitudinal axis of the housing 191. An upper edge of the blocking plate 193 may be connected to the top wall of the housing 191. The two side edges of the blocking plate 193 may each be connected to the inner side wall of the housing 191, and the lower edge of the blocking plate 193 may be located above the gas baffle 195. The gas outlet 198 and the gas inlet 194 may be located on opposite sides of the blocking plate 193. The gas to be separated that enters the upstream chamber 201 from the gas inlet 194 can enter the downstream chamber 202 only through the lower chamber 203. In other embodiments, the blocking plate 193 can be disposed obliquely with respect to the longitudinal axis of the housing 191. In an embodiment, a surface of the blocking plate 193 facing the gas inlet 194 may be an uneven surface, not a smooth surface, which may be beneficial to the condensation of liquid drops.

Figure 4:
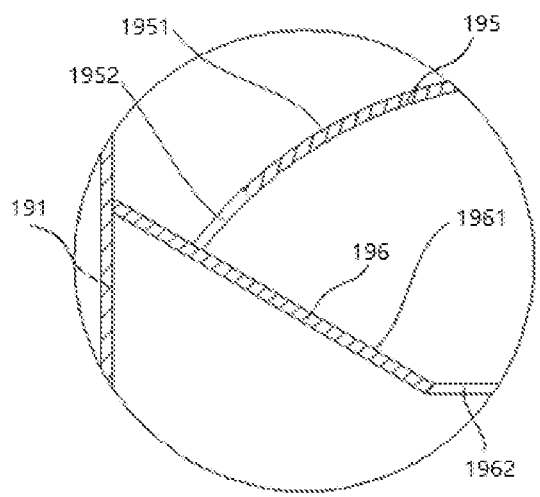
FIG. 4 is a schematic diagram illustrating an enlarged view of area B in FIG. 3A.
Figure 6A:
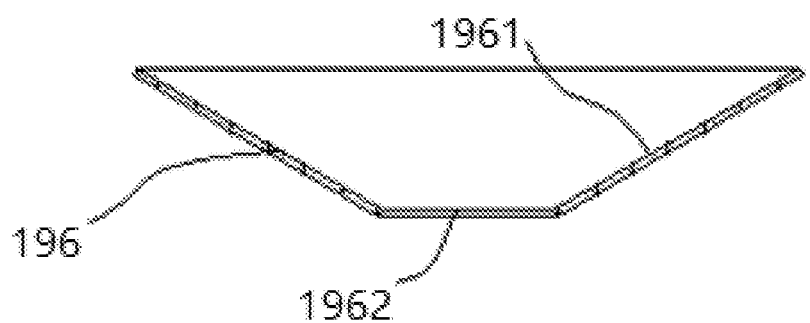
FIG. 6A is a schematic diagram illustrating a cross-sectional view of a liquid collector in FIG. 3A.
Figure 6B:
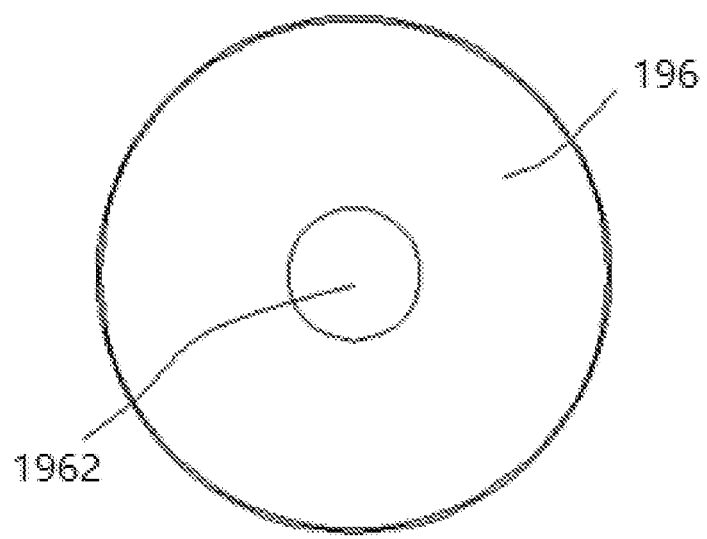
FIG. 6B is a schematic diagram illustrating a top view of the liquid collector in FIG. 3A.

Referring to FIGS. 4, 6A, and 6B, an outer edge of the liquid collector 196 may be connected to the inner side wall of the housing 191 by welding, for example. The liquid collector 196 may be configured to collect the condensed liquid. The liquid collector 196 may include, without limitation, a first flow guide surface 1961 that is configured to collect the liquid and to cause the liquid to flow downward. The first flow guide surface 1961 can have a truncated cone shape or a concave arc shape that protrudes downward. A bottom portion of the first flow guide surface 1961 may be provided with a first hole 1962, which is opposite to the liquid outlet 197. The liquid outlet 197 may be disposed below the first hole 1962. The liquid can enter the liquid outlet 197 from the first hole 1962. The diameter of the first hole 1962 can be larger than the diameter of the liquid outlet 197. In this embodiment, the liquid collector 196 has a funnel shape, and an outer edge of a top portion of the liquid collector 196 may be connected to the inner side wall of the housing 191.

Figure 5A:
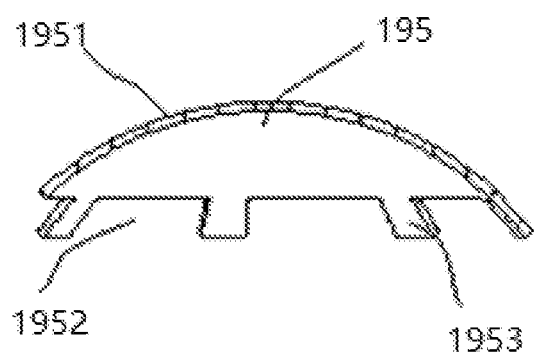
FIG. 5A is a schematic diagram illustrating a cross-sectional view of a gas baffle in FIG. 3A.
Figure 5B:
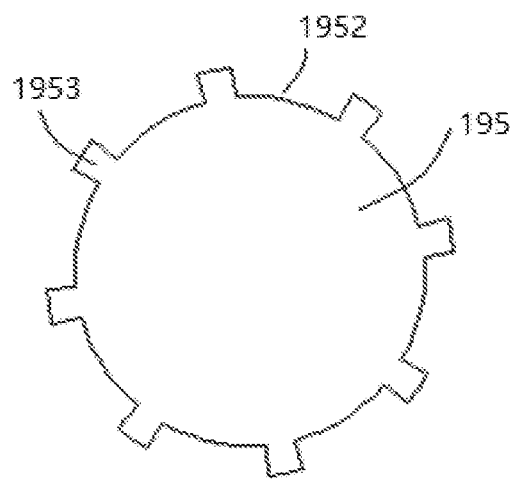
FIG. 5B is a schematic diagram illustrating a top view of the gas baffle in FIG. 3A.

Referring to FIGS. 5A and 5B, an upper surface of the gas baffle 195 may form a second flow guide surface 1951. An outer edge of the gas baffle 195 may be connected to the first flow guide surface 1961 of the liquid collector 196 through at least one protrusion 1953 by welding, for example, thereby forming a second hole(s) 1952 between the outer edge of the gas baffle 195 and the first flow guide surface 1961. The second flow guide surface 1951 can block the downward flow of the gas above it, thereby avoiding that the liquefied ethylene oxide liquid being flushed or even re-gasified due to a disturbance of liquid by the gas flow. The liquid that is condensed on the gas baffle 195 and the liquid that falls on the gas baffle 195 can flow to the second hole(s) 1952 along the second flow guide surface 1951, can be discharged through the first hole 1962 along the first flow guide surface 1961, and can be discharged from the gas liquefaction separator 19 through the liquid outlet 197. The number of the at least one protrusion 1953 can be two or more, and a plurality of protrusions 1953 may be arranged uniformly and spaced apart from each other in the circumferential direction or along a circumference of the gas baffle 195, thereby forming a plurality of second holes 1952 that are evenly distributed around the edge of the gas baffle 195. A middle portion of the second flow guide surface 1951 may be upwardly arched, and may have a shape with a higher middle portion and a lower edge, which is beneficial to guide the condensed liquid into the second hole(s) 1952. The gas baffle 195 may have, for example, a convex arc-shaped plate, and a convex arc-shaped upper surface of the convex arc-shaped plate may form the second flow guide surface 1951. In an embodiment, the gas baffle 195 may have a curved pot lid shape, which can block the gas above it and can avoid the liquefied ethylene oxide liquid from being flushed due to the disturbance of liquid by the gas flow.

An exhaust pipe 192 may be further disposed in the gas outlet 198 and may extend inside the housing 191 through the top wall of the housing 191. Specifically, the exhaust pipe 192 may extend into the downstream chamber 202. In this way, the liquid ethylene oxide is prevented from being flushed out of the gas liquefaction separator 19 by the flow of the gas to be discharged.

Figure 7:
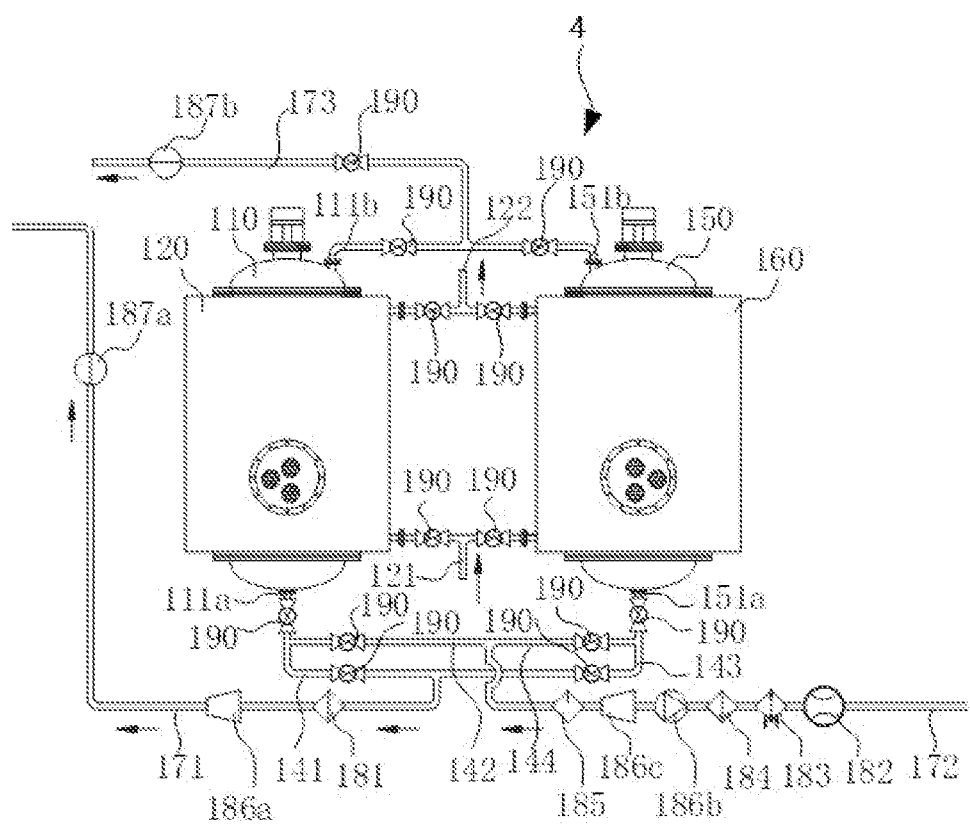
FIG. 7 is a schematic diagram illustrating a pressure swing adsorption recovery system according to an embodiment of the present disclosure.
Figure 8:
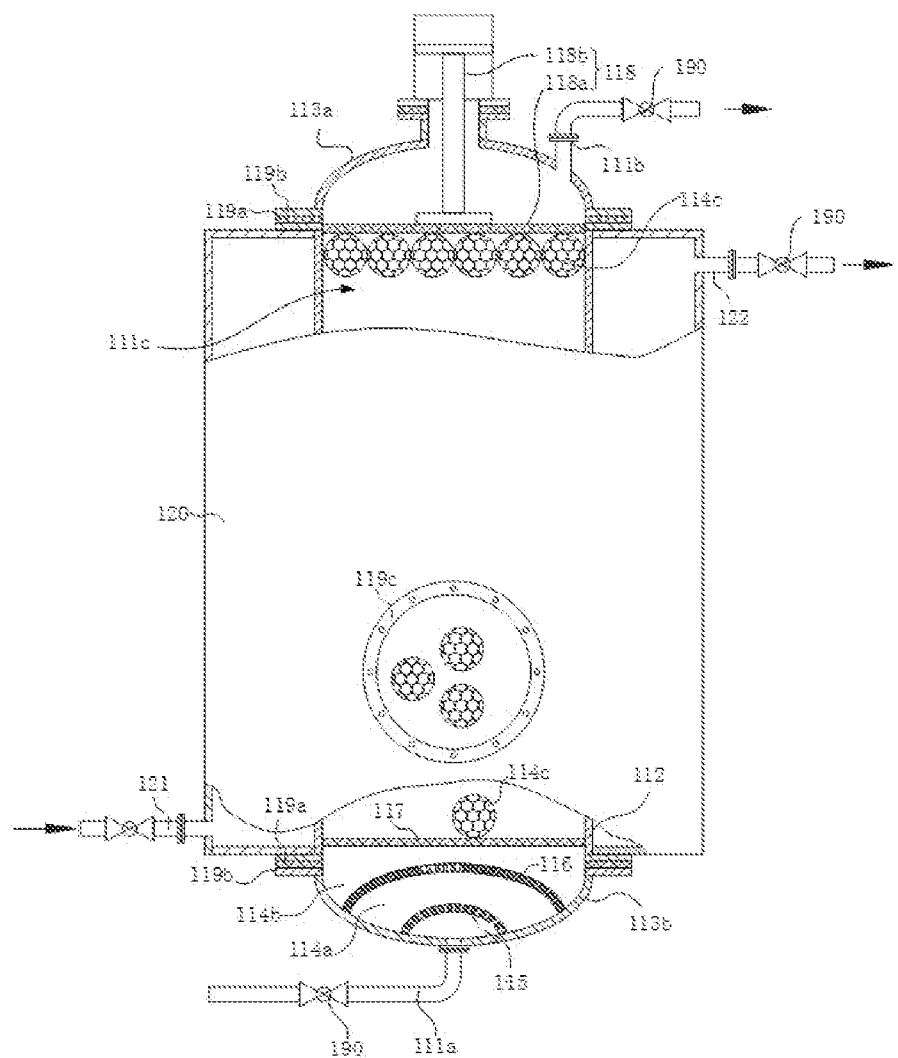
FIG. 8 is a schematic diagram illustrating a pressure swing adsorption column in the pressure swing adsorption recovery system according to an embodiment of the present disclosure.

As shown in FIGS. 7 to 8, in an embodiment, the PSA recovery system 4 may include a first pressure swing adsorption column 110, a first thermostatic assembly 120, a first branch pipe 141, and a second branch pipe 142. In a further embodiment, the PSA recovery system 4 may further include a second pressure swing adsorption column 150, a second thermostatic assembly 160, a third branch pipe 143, and a fourth branch pipe 144. The pressure swing adsorption column 110 or 150 may each also be referred to as a "PSA column."

Specifically, in some embodiments, the first PSA column 110 may be provided with a first accommodating chamber 111c, a first gas vent 111a, and a first gas outlet 111b, the first gas vent 111a and the first gas outlet 111b being in fluid communication with the first accommodating chamber 111c. The first accommodating chamber 111c may be configured to accommodate an adsorbing material 114c. The first PSA column 110 may be at least partially provided near the first thermostatic assembly 120. The first branch pipe 141 may be configured to provide fluid communication between the first gas vent 111a and the recovery and storage system 12. The second branch pipe 142 may be configured to pass the sterilization exhaust gas to be treated from the gas liquefaction recovery system 3 to the first PSA column 110 through the first gas vent 111a. In an embodiment, the second branch pipe 142 might fluidly communicate with the exhaust pipe 192 (which may be disposed in the gas outlet 198) of the gas liquefaction separator 19 of the gas liquefaction recovery system 3. In this embodiment, the first gas vent 111a may be located at a bottom portion of the first PSA column 110, while the first gas outlet 111b may be located at a top portion of the first PSA column 110.

According to some embodiments, the second PSA column 150 may be provided with a second accommodating chamber, a second gas vent 151a, and a second gas outlet 151b, the second gas vent 151a and the second gas outlet 151b being in fluid communication with the second accommodating chamber. The second accommodating chamber may be configured to accommodate the adsorbing material 114c. The second PSA column 150 may be at least partially provided near the second thermostatic assembly 160. The third branch pipe 143 may be configured to provide fluid communication between the second gas vent 151a and the recovery and storage system 12. The fourth branch pipe 144 may be configured to pass the sterilization exhaust gas to be treated from the gas liquefaction recovery system 3 to the second PSA column 150 through the second gas vent 151a. In an embodiment, the fourth branch pipe 144 might fluidly communicate with the exhaust pipe 192 of the gas liquefaction separator 19 (which may be disposed in the gas outlet 198) of the gas liquefaction recovery system 3. In this embodiment, the second gas vent 151a may be located at a bottom portion of the second PSA column 150, while the second gas outlet 151b may be located at a top portion of the second PSA column 150.

In an embodiment, the first PSA column 110 may be at least partially disposed in the first thermostatic assembly 120, and the second PSA column 150 may be at least partially disposed in the second thermostatic assembly 160. The first thermostatic assembly 120 and the second thermostatic assembly 160 can provide the first PSA column 110 and the second PSA column 150 with lower temperatures required in the adsorption process, thereby improving the efficiency of the adsorption treatment. At the same time, the gas vents and the gas outlets of the first PSA column 110 and the second PSA column 150 may be respectively fluidly connected in parallel through two or more of the first connecting pipes, so that when the entire treatment device is in operation, the first PSA column 110 and the second PSA column 150 can alternately perform the processes of adsorption and desorption, so that the exhaust gas can be continuously treated, and the treatment efficiency can be improved.

In some embodiments, the PSA recovery system 4 may further include a first main pipe 171 and a second main pipe 172. The first branch pipe 141 and the third branch pipe 143 may commonly fluidly communicate with one end of the first main pipe 171. The other end of the first main pipe 171 may be configured to fluidly communicate with the recovery and storage system 12. The second branch pipe 142 and the fourth branch pipe 144 may commonly fluidly communicate with one end of the second main pipe 172, and the other end of the second main pipe 172 may be configured to fluidly communicate with the exhaust pipe 192 (which may be disposed in the gas outlet 198) of the gas liquefaction separator 19 of the gas liquefaction recovery system 3. The first branch pipe 141 and the third branch pipe 143 may meet at the first main pipe 171, which may facilitate the ethylene oxide being desorbed and depressurized from the first PSA column 110 and the second PSA column 150 to be discharged into the recovery and storage system 12 through the first main pipe 171. The second branch pipe 142 and the fourth branch pipe 144 may meet at the second main pipe 172, which may facilitate the exhaust gas to be treated entering into the first PSA column 110 and the second PSA column 150.

According to some embodiments, the PSA recovery system 4 may further include a gas filter 181. The gas filter 181 may be disposed on the first main pipe 171. The gas filter 181 may provide fluid communication with the first branch pipe 141 and the third branch pipe 143 through the first main pipe 171. The gas filter 181 can filter the recovered gas that is desorbed from the first PSA column 110 and the second PSA column 150, such as ethylene oxide, and can filter out the particulate matter carried out from fillers, thereby improving the cleanliness of the recovered gas that is recovered from the PSA recovery system 4 and directed into the recovery and storage system 12.

In some embodiments, the PSA recovery system 4 may further include a flow meter 182, a heat exchanger 183, a gas-liquid separator 184, and a gas dryer 185. The flow meter 182, the heat exchanger 183, the gas-liquid separator 184, and the gas dryer 185 may be provided on the second main pipe 172, may fluidly communicate through the second main pipe 172, and may be sequentially provided in a direction away from the gas liquefaction recovery system 3.

The flow meter 182 may be used to detect the gas flow in the second main pipe 172, so as to facilitate real-time tracking and monitoring of the gas flow in the second main pipe 172. The heat exchanger 183 can reduce the higher temperature of sterilized ethylene oxide exhaust gas to improve the adsorption rate. The gas-liquid separator 184 and the gas dryer 185 can remove moisture in the exhaust gas, thus improving the dryness of the gas, and improving the adsorption rate.

According to some embodiments, the PSA recovery system 4 may further include a first booster pump 186a, a first vacuum pump 186b, and a second booster pump 186c. The first booster pump 186a may be provided on the first main pipe 171, for example, between the gas filter 181 and the recovery and storage system 12. The first booster pump 186a can increase the gas pressure in the recovery and storage system 12, so as to increase the amount of stored gas. The first vacuum pump 186b and the second booster pump 186c may be provided on the second main pipe 172, in some cases, with both between the gas-liquid separator 184 and the gas dryer 185. The first vacuum pump 186b may be configured to extract the exhaust gas treated by the gas liquefaction recovery system 3. The second booster pump 186c may be configured to boost the exhaust gas in the second main pipe 172, thereby controlling the gas pressure in the first PSA column 110 or the second PSA column 150, and further increasing the adsorption rate of the gas to be recovered in the exhaust gas, such as ethylene oxide, in the first PSA column 110 or the second PSA column 150. In some embodiments, both the first booster pump 186a and the second booster pump 186c may include pneumatic booster pumps, and the power gas may be nitrogen, or the like.

In some embodiments, the PSA recovery system 4 may further include at least one of a first ethylene oxide concentration detector 187a, a second ethylene oxide concentration detector 187b, or a third ethylene oxide concentration detector 187c, and/or the like. The first ethylene oxide concentration detector 187a may be provided on the first main pipe 171, for example, between the gas filter 181 and the recovery and storage system 12. In some cases, the PSA recovery system 4 may further include a discharge pipe 173. The first gas outlet 111b and the second gas outlet 151b may both be in fluid communication with the discharge pipe 173 through a channel. In an embodiment, the discharge pipe 173 may fluidly communicate with the reaction system 5. The second ethylene oxide concentration detector 187b may be provided on the discharge pipe 173. The first ethylene oxide concentration detector 187a may be configured to monitor the concentration of the desorbed and recovered ethylene oxide, so as to monitor the desorption effect and to control the process flow. The second ethylene oxide concentration detector 187b may be configured to detect the concentration of the ethylene oxide in the first PSA column 110 and in the second PSA column 150 after the adsorption process, to detect the adsorption effect and to control the process flow.

According to some embodiments, the first thermostatic component 120 may include a first thermostatic water tank. The first thermostatic water tank may be sleeved on the outer wall of the first PSA column 110. The second thermostatic component 160 may include a second thermostatic water tank. The second thermostatic water tank may be sleeved on the outer wall of the second PSA column 150. In some embodiments, the thermostatic water tank may be used as the thermostatic assembly, and the characteristic of large specific heat capacity of water may be used to facilitate the rapid cooling of the first PSA column 110 and the second PSA column 150, and thus to facilitate the control of the temperature level. Further, the first thermostatic water tank may be provided with a water inlet 121 and a water outlet 122. The water inlet 121 and the water outlet 122 may provide fluid communication with a rainwater collector. This setting allows the thermostatic water tank to use rainwater for cooling, and the heat-exchanged water can also enter the rainwater collector to be mixed with other unheated rainwater to cool down, thereby reducing treatment costs. In some embodiments, the water inlet 121 can alternatively or additionally be fluidly connected to a tap water source.

In some embodiments, the PSA recovery system 4 may further include a plurality of valves 190. The first branch pipe 141, the second branch pipe 142, the third branch pipe 143, the fourth branch pipe 144, the first gas vent 111a, the second gas vent 151a, the first gas outlet 111b, the second gas outlet 151b, the discharge pipe 173, the water inlet 121, and the water outlet 122 may all be provided with a valve 190. The arrangement of these valves 190 facilitates automatic control and inspection for maintenance or replacement of parts. At the same time, it may also be beneficial to the realization of a variety of operating processes, such as alternately pressurized adsorption and depressurized desorption of the first PSA column 110 and the second PSA column 150, and a cooling cycle during the corresponding pressurized adsorption process accompanied with the first thermostatic component 120 or the second thermostatic component 160, so as to achieve continuous treatment of ethylene oxide exhaust gas.

As shown in FIG. 8, in an embodiment, the first PSA column 110 may include a first column body 112, a first upper sealing cover 113a, a first lower sealing cover 113b, a water-absorbing material 114a, an oil-absorbing material 114b, and the adsorbing material 114c, a first-stage gas distributor 115, a second-stage gas distributor 116, a lower mesh plate 117, and the first filler compressing assembly 118.

Specifically, according to some embodiments, the first upper sealing cover 113a and the first lower sealing cover 113b may be connected to the top and bottom ends of the first column body 112, respectively. The first accommodating chamber 111c may be enclosed by the first column body 112, the first upper sealing cover 113a, and the first lower sealing cover 113b. The first accommodating chamber 111c may be configured to accommodate the adsorbing material 114c. The upper and lower sealing covers 113a and 113b may be provided for easy opening to repair and replace the filling material in the first column body 112. According to some embodiments, the adsorbing material 114c may include, but is not limited to, a 13× molecular sieve and/or a 4 A molecular sieve, or the like. These two molecular sieve materials can each achieve efficient separation of ethylene oxide and nitrogen under high pressure, and may be beneficial to the desorption of ethylene oxide under low pressure, so as to realize the recovery and reuse of ethylene oxide.

Further, gaskets 119a may be respectively provided between the first upper sealing cover 113a and the first column body 112, and between the first lower sealing cover 113b and the first column body 112, so as to enhance gas tightness inside the first PSA column 110. The first upper sealing cover 113a and the first column body 112, and the first lower sealing cover 113b and the first column body 112, may also be locked and connected by a flange 119b. In some embodiments, the first column body 112 may also be provided with an observation hole 119c, and the observation hole 119c may be covered using a transparent sealing plate. The first thermostatic assembly 120 can be provided in an area that avoids blocking the observation hole 119c, or can be provided with an observation portion corresponding to the observation hole 119c. The provision of the observation hole 119c may be convenient for observing the internal condition of the first PSA column 110, and may be convenient for accessing the first accommodating chamber 111c for cleaning and replacement of the adsorbing material 114c.

Further, the first-stage gas distributor 115, the water-absorbing material 114a, the second-stage gas distributor 116, the oil-absorbing material 114b, and the lower mesh plate 117 may be sequentially provided between the first lower sealing cover 113b and the adsorbing material 114c along the direction toward an interior of the first accommodating chamber 111c. Filling a space between the first lower sealing cover 113b and the adsorbing material 114c with a water-absorbing material 114a may contribute to absorption of the moisture in the mixed ethylene oxide exhaust gas and may prevent the moisture from affecting the adsorption of ethylene oxide. Filling the space with an oil-absorbing material may contribute to absorption of the oil component(s) that may be mixed in the mixed ethylene oxide exhaust gas, thereby avoiding pollution of the adsorbing material 114c with the oil component(s), so as to extend the service life of the adsorbing material 114c. In some embodiments, the first filler compressing assembly 118 may be connected to the first upper sealing cover 113a and may be used to press on the top end of the adsorbing material 114c. The first filler compressing assembly 118 may compress the fillers, thereby increasing the filling amount and improving the adsorption capacity for ethylene oxide, while also compressing the adsorbing material 114c, and preventing the adsorbing material 114c from being blown up or worn out. According to some embodiments, the first filler compressing assembly 118 may include a filler compressing grid tray 118a and a first filler compressing pillar 118b. The filler compressing grid tray 118a may be located in the first accommodating chamber 111c and may be used to press on the top end of the adsorbing material 114c. One end of the filler compressing pillar 118b may be connected to the filler compressing grid tray 118a, while passing through the first upper sealing cover 113a. The filler compressing pillar 118b can press the filler compressing grid tray 118a against the adsorbing material 114c.

Similarly, the second PSA column 150 may include a second column body, a second upper sealing cover, a second lower sealing cover, and the second filler compressing assembly. The second PSA column 150 may also be filled with the water-absorbing material 114a, the oil-absorbing material 114b, the first-stage gas distributor 115, the second-stage gas distributor 116 and the lower mesh plate 117. The connection structure and interrelationship of these components may be the same as that of the first PSA column 110, and the description of the connection structure and interrelationship of the components of the first PSA column 110 are applicable to the corresponding connection structure and interrelationship of components of the second PSA column 150.

When the PSA recovery system 4 of the embodiment of the present disclosure is used to treat ethylene oxide-containing sterilization exhaust gas, the thermostatic water tank may be continuously fed with cooling water to circulate, so that the PSA column 110 or 150 can maintain a low constant temperature (20° C.-30° C.). After it enters the PSA column 110 or 150, the ethylene oxide-containing sterilization exhaust gas may be evenly dispersed into the water-absorbing material 114a through the first-stage gas distributor 115 to remove residual moisture, and after being dried, the ethylene oxide-containing sterilization exhaust gas may be evenly dispersed into the oil-absorbing material 114b through the second-stage gas distributor 116 to remove any oil component(s), and then, the ethylene oxide-containing sterilization exhaust gas may be evenly dispersed into the adsorbing material 114c through the lower mesh plate 117 for adsorption. After ethylene oxide-containing sterilization exhaust gas has passed through the adsorbing material 114c and has been pressurized and adsorbed, the residual exhaust gas may pass through a filler compressing grid tray 118a and may be discharged through the first gas outlet 111b to the reaction system 5. Then, the recovered ethylene oxide that is depressurized and desorbed may be discharged and directed into the recovery and storage system 12 from the branch pipe (i.e., first or third branch pipe 141 or 143) that is provided at the bottom portion of the PSA column 110 or 150.

Figure 9:
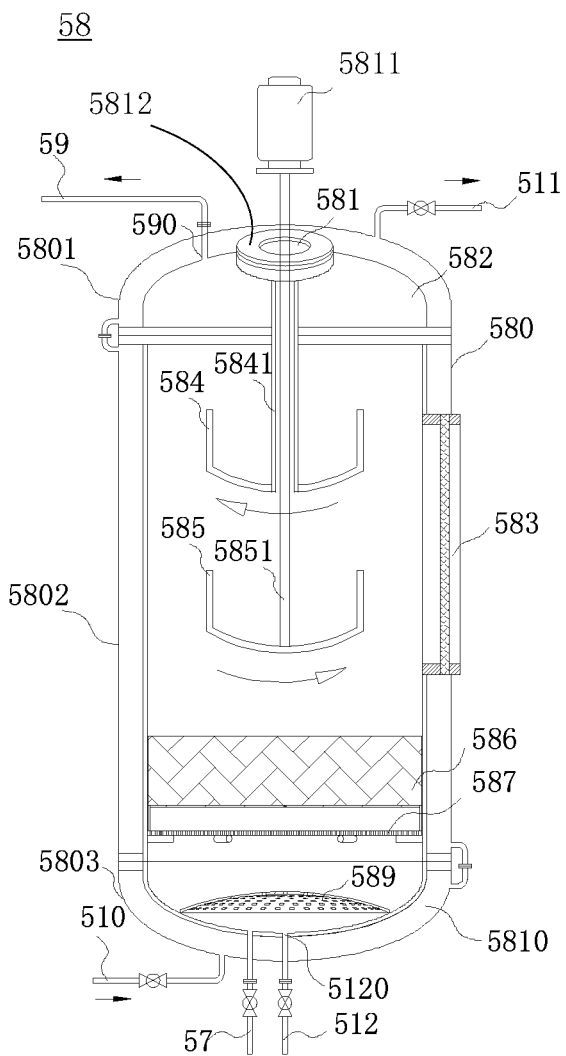
FIG. 9 is a schematic diagram illustrating a cross-sectional view of a reaction system according to an embodiment of the present disclosure.

FIG. 9 shows a cross-sectional view of a reaction system 5 according to an example embodiment of the present disclosure. The reaction system 5 comprises a reaction column 58.

The reaction column 58 may include a column body 580 with an inner cavity 582 that contains a liquid substrate for catalyzing sterilization gas (such as ethylene oxide) in sterilization exhaust gas (such as ethylene oxide containing sterilization exhaust gas) to react with water. The bottom of the column body 580 (also referred to as a "bottom portion" or "lower portion") might include a gas inlet pipe 512 and a liquid outlet pipe 57. EO-containing sterilization exhaust gas may be injected via the gas inlet pipe 512 into the bottom portion of the inner cavity 582 where the liquid substrate can catalyze EO in the EO-containing sterilization exhaust gas to react with water to generate ethylene glycol. The liquid outlet pipe 57 may be used to discharge the liquid substrate out of the inner cavity 582 for replacement of the liquid substrate. The top of the column body 580 (also referred to as "top portion" or "upper portion") may be provided with a gas outlet pipe 59 with a gas inlet 590 that may be disposed above a liquid level of the liquid substrate. Residual gas, after passing through the liquid substrate, may be discharged through the gas outlet pipe 59. At least one gas distributor, such as a first gas distributor 589, may be provided in the inner cavity 582 above a gas outlet 5120 of the gas inlet pipe 512 for dispersing the EO-containing sterilization exhaust gas injected into the inner cavity 582 via the gas inlet pipe 512. The at least one gas distributor 589 may be configured to disperse the EO-containing sterilization exhaust gas, from the gas inlet pipe 512, evenly within the inner cavity 582, and thereby increasing contact between the EO-containing sterilization exhaust gas and the liquid substrate, diffusing the EO-containing sterilization exhaust gas in the liquid substrate, and improving efficiency in ethylene oxide treatment.

The column body 580 in this example may include, without limitation, an upper sealing cover 5801, a cylindrical body 5802, and a lower sealing cover 5803 assembled together. The upper sealing cover 5801 and the lower sealing cover 5803 may be coupled to an upper portion (e.g., top) and a lower portion (e.g., bottom) of the cylindrical body 5802, respectively. In some embodiments, a seal may be formed between the cylindrical body 5802 and each of the upper sealing cover 5801 and lower sealing cover 5803. Accordingly, each of the upper sealing cover 5801 and lower sealing cover 5803 may be configured to form a respective seal circumferentially around the respective upper and lower portions of the cylindrical body 5802 that may be in contact with the upper sealing cover 5801 and lower sealing cover 5803 when in a closed position. The seal may be configured to prevent liquid, gas, or both liquid and gas from passing through the seal.

The liquid substrate contained in the inner cavity 582 may, for example, be a liquid acid substrate configured to physically adsorb ethylene oxide and to chemically react with ethylene oxide to produce alcohol, thereby decontaminating ethylene oxide in the sterilization exhaust gas efficiently to reduce environmental pollution or contamination.

In some embodiments, the liquid acid substrate may include, but is not limited to, ethylene oxide catalytic concentrate, or the like. According to some embodiments, the ethylene oxide catalytic concentrate may be mainly composed of a combination of inorganic acids, sulfonic acids, and unsaturated fatty acids. In some cases, the molar ratio of inorganic acids to sulfonic acids to oleic acids may range from 1:1:1 to 1:1000:100, or the like. Alternatively, the ethylene oxide catalytic concentrate may include one or two of inorganic acids, sulfonic acids, or unsaturated fatty acids. In some embodiments, the inorganic acids may include, without limitation, at least one of sulfuric acid or phosphoric acid, and/or the like. According to some embodiments, the sulfonic acids may have a general formula of R—$SO_3H$, where R is a hydrocarbyl, and may include, but are not limited to, at least one of methylsulphonic acid, ethylsulfonic acid, propylsulfonic acid, butylsulfonic acid, pentylsulfonic acid, hexylsulfonic acid, heptylsulfonic acid, octylsulfonic acid, nonylsulfonic acid, decylsulfonic acid, undecylsulfonic acid, dodecylsulfonic acid, tridecylsulfonic acid, tetradecylsulfonic acid, pentadecylsulfonic acid, hexadecylsulfonic acid, heptadecylsulfonic acid, octadecylsulfonic acid, methylsulfonic acid, ethylbenzenesulfonic acid, propylbenzenesulfonic acid, butylbenzenesulfonic acid, pentylbenzenesulfonic acid, hexylbenzenesulfonic acid, heptybenzenesulfonic acid, octylbenzenesulfonic acid, nonylbenzenesulfonic acid, decylbenzenesulfonic acid, undecylbenzenesulfonic acid, dodecylbenzenesulfonic acid, tridecylbenzenesulfonic acid, tetradecylbenzenesulfonic acid, pentadecylbenzenesulfonic acid, hexadecylbenzenesulfonic acid, heptadecylbenzenesulfonic acid, octadecylbenzenesulfonic acid, nonadecylbenzenesulfonic acid, or eicosylbenzenesulfonic acid, and/or the like. Merely by way of example, in some cases, the unsaturated fatty acids might include, without limitation, at least one of oleic acid, linoleic acid, or linolenic acid, and/or the like. In the above example, the ethylene oxide catalytic concentrate with its strong acidic properties and surfactant properties may be selected as a catalyst to treat the EO-containing sterilization exhaust gas. Advantageously, the strong acidic properties of ethylene oxide catalytic concentrate allow it to catalyze the reaction of the EO-containing sterilization exhaust gas, while the surfactant property of ethylene oxide catalytic concentrate increases efficiency of adsorption of the EO-containing sterilization exhaust gas by the ethylene oxide catalytic concentrate, thereby improving treatment efficiency of the EO-containing sterilization exhaust gas, thus ensuring safety and reliability of the treatment process of the EO-containing sterilization exhaust gas, and yielding high treatment performance and low environmental pollution or contamination.

Figure 10A:
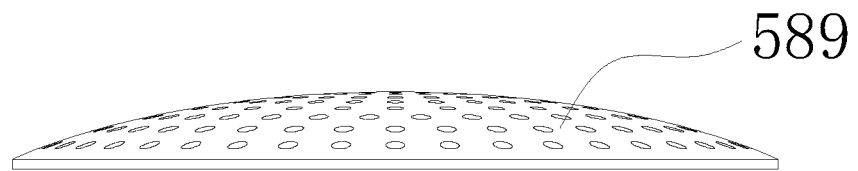
FIG. 10A is a schematic diagram illustrating a front view of a first gas distributor that may be used in the reaction system of FIG. 9.
Figure 10B:
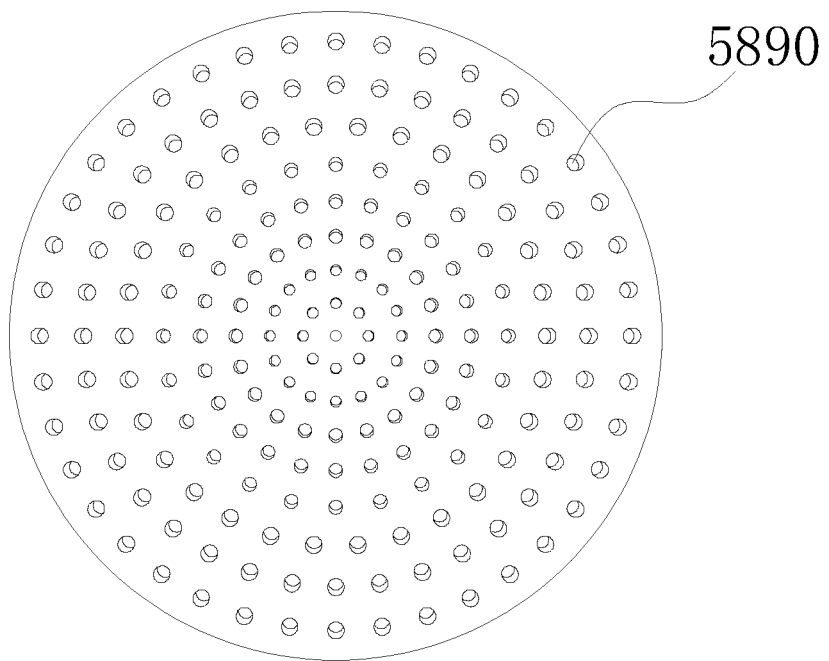
FIG. 10B is a schematic diagram illustrating a top view of the first gas distributor of FIG. 10A.

In some embodiments, referring to FIGS. 10A and 10B, the at least one gas distributor may include a first gas distributor 589. The first gas distributor 589 may comprise a curved plate with a high center, pointing inward towards the cylindrical body 5802, and curving lower moving from the center to the edge of the curved plate. That is, the center may be high and the edge may be low relative to each other. In some embodiments, the edge may be coupled to a bottom wall of the inner cavity 582. The curved plate may further be coupled to an inner wall of the lower sealing cover 5803. The curved plate may comprise a plurality of first air holes 5890, each of the plurality of first air holes 5890 being circular in shape and being distributed in an annular arrangement. For example, in some embodiments, the plurality of first air holes 5890 may include one or more concentric rings of air holes, radiating from the center outward towards the edge. Thus, the gas inlet pipe 512 may be in fluid communication with the gas outlet pipe 59 via the plurality of first air holes 5890. From the center to the edge of the curved plate, the hole size of the plurality of first air holes 5890 may gradually increase. In alternative embodiments, the hole size of the plurality of first air holes 5890 may gradually decrease, moving from the center to the edge of the curved plate, or may be the same in terms of hole size throughout the curved plate. In some of the examples, moving from the center to the edge of the curved plate, the plurality of first air holes 5890 may gradually increase in hole pitch. The plurality of first air holes 5890 may be configured to evenly distribute, in the inner cavity 582, the EO-containing sterilization exhaust gas that is being injected into the inner cavity 582 through the first gas distributor 589.

Figure 11:
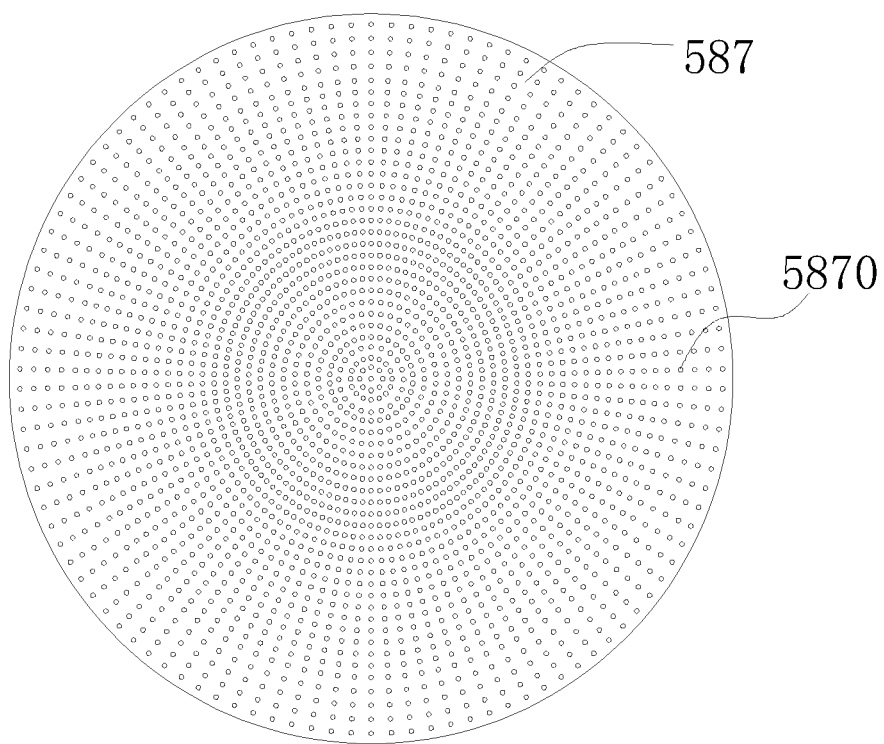
FIG. 11 is a schematic diagram illustrating a top view of a second gas distributor that may be used in the reaction system of FIG. 9.

In some of the examples, referring to FIG. 11, the at least one gas distributor may further include a second gas distributor 587, which may be a flat plate with a center and an edge, the edge being connected to a side wall of the inner cavity 582. The flat plate may be located above the curved plate or the first gas distributor 589 (and may be closer to the center of the inner cavity 582), and may be further coupled to an inner wall of the cylindrical body 5802. The flat plate may include a plurality of second air holes 5870, each of the plurality of second air holes 5870 being circular in shape and being in an annular arrangement. For example, in some embodiments, the plurality of second air holes 5870 may include one or more concentric rings of air holes, radiating from the center outward towards the edge. Moving from the center to the edge of the flat plate, the plurality of second air holes 5870 may be configured to gradually increase in hole pitch. In some examples, each of the plurality of second air holes 5870 may be the same in terms of hole size. In alternative embodiments, the hole size of the plurality of second air holes 5870 may gradually increase or gradually decrease, moving from the center to the edge of the flat plate. The plurality of second air holes 5870 may be specifically designed to further evenly disperse the EO-containing sterilization exhaust gas by diffusing the release of the EO-containing sterilization exhaust gas into the liquid substrate, thereby further increasing the contact area between the EO-containing sterilization exhaust gas and the liquid substrate.

Figure 12:
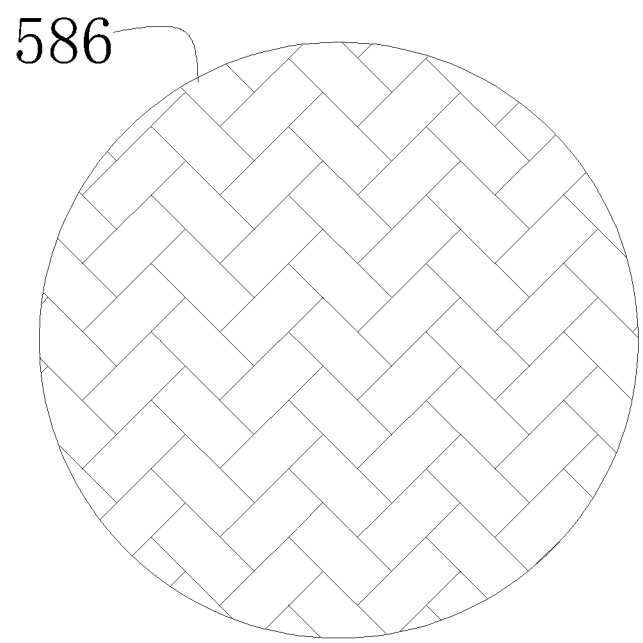
FIG. 12 is a schematic diagram illustrating a partially enlarged view of a filter screen that may be used in the reaction system of FIG. 9.

With reference to FIGS. 9 and 12, the reaction column 58 may further include a filter screen 586 located in the inner cavity 582. The filter screen 586 may be removably coupled to the side wall of the inner cavity 582 and may be located above the at least one gas distributor (e.g., the first gas distributor 589 and/or the second gas distributor 587). The filter screen 586 may further be coupled to the inner wall of the cylindrical body 5802. In some embodiments, the filter screen 586 may include, but is not limited to, a multi-layer mesh structure, or the like. The filter screen 586 may be configured to filter and evenly disperse EO-containing sterilization exhaust gas, thereby uniformly mixing the EO-containing sterilization exhaust gas with the liquid acid substrate. The filter screen 586 may, in some embodiments, be configured to be periodically replaced or maintained (e.g., removed and cleaned). It is to be understood that the above-described gas distributors 587, 589 and filter screen 586 may all be disposed below the working liquid level of the liquid substrate (e.g., below a threshold effective amount of liquid substrate) and may be submerged in the liquid substrate.

Referring again to FIG. 9, the reaction column 58 may further include two stirrers 584, 585 that may be disposed in the inner cavity 582, each stirrer being located above the filter screen 586 and being configured to stir the liquid substrate. A primary stirrer 585 may be connected to a first rotating shaft 5851. An upper end of the first rotating shaft 5851 may extend out of the column body 580 and may be coupled to a first driver 5811. The first driver 5811 may, for example, include, without limitation, a motor, an actuator, or other suitable device for driving the primary stirrer 585. A secondary stirrer 584 may be positioned above the primary stirrer 585 and may be coupled to a second rotating shaft 5841. An upper end of the second rotating shaft 5841 may extend out of the upper sealing cover 5801 of the column body 580 and may be coupled to a second driver 5812. The second driver 5812, like the first driver 5811, may similarly include, without limitation, a motor, an actuator, or other suitable device for driving the secondary stirrer 584. The second rotating shaft 5841 may be disposed coaxially with the first rotating shaft 5851.

In some examples, the primary stirrer 585 may be configured to rotate in a first rotational direction, while the secondary stirrer 584 may be configured to rotate in a second rotational direction that is opposite to the first rotational direction of the primary stirrer 585. In some examples, the first driver 5811 and the second driver 5812 may be the same driver. For example, the first driver 5811 may be configured to be selectively connected to the first rotating shaft 5851 and the second rotating shaft 5841. Alternatively, a mechanical coupling may be provided between the first rotating shaft 5851 and the second rotating shaft 5841, such that, when the first driver 5811 is activated, the mechanical coupling may be configured to cause the first rotating shaft 5851 and the second rotating shaft 5841 to contra-rotate (i.e., to rotate in opposite directions) synchronously, thereby causing the primary stirrer 585 and the secondary stirrer 584 to contra-rotate synchronously to agitate the liquid substrate. Accordingly, the mechanical coupling may include, without limitation, one or more gears, a transmission, or other mechanical coupling as known to those skilled in the art. In some embodiments, the mechanical coupling may be coupled directly to the first driver 5811, with each of the first rotating shaft 5851 and the second rotating shaft 5841 being coupled to the first driver 5811 via the mechanical coupling. Alternatively, the first driver 5811 may be coupled to one of the first rotating shaft 5851 or the second rotating shaft 5841. The mechanical coupling may, in turn, couple the shaft that is coupled directly to the first driver 5811 to the other shaft that is not coupled directly to the first driver 5811.

It is to be understood that, in some further embodiments, the reaction column 58 may comprise an alternative arrangement utilizing a single primary stirrer, or alternatively using three or more stirrers that may be provided in the inner cavity 582.

In some embodiments, the column body 580 may further include a sandwich chamber 5810, a coolant inlet pipe 510, and a coolant outlet pipe 511, the sandwich chamber 5810 surrounding the inner cavity 582 with the coolant inlet pipe 510 and the coolant outlet pipe 511 being in fluid communication with the sandwich chamber 5810. Thus, in some embodiments, coolant may be allowed to enter the sandwich chamber 5810 from the coolant inlet pipe 510, to exit from the coolant outlet pipe 511, and to be recycled so as to cool the reaction column 58. The coolant may include, without limitation, water (including tap water, distilled water, deionized water, ultrapure water, and the like), antifreeze, oils, liquefied gas, or other fluid coolant as known to those skilled in the art. In some examples, water may be utilized as a coolant, with the water temperature being controlled to be between, for example, 20° C. and 30° C. In some embodiments, the reaction column 58 may further include a cooling device for cooling the column body 580 of the reaction column 58, the cooling device being coupled to the coolant inlet pipe 510 and/or to the coolant outlet pipe 511. In some examples, the cooling device may include, but is not limited to, a water storage tank, a pump, and a circulating water pipe, or the like. In some cases, the circulating water pipe may fluidly couple each of the coolant inlet pipe 510 and the coolant outlet pipe 511 with the water storage tank, while the pump may be mounted on the circulating water pipe and may be configured to circulate the water. In yet further embodiments, the cooling device may further include a cooler coupled to one or more of the water storage tank or the circulating water pipe. The cooler may include, without limitation, a heat pump, a thermoelectric cooler, a vapor compression cooler, or other cooling device as known to those skilled in the art.

In some of the examples, the column body 580 is provided with a top viewer 581 and/or a side-wall viewer 583. The top viewer 581 may be fixed, for example, to the top portion of the upper sealing cover 5801 around the first rotating shaft 5851 and the second rotating shaft 5841. The side wall viewer 583 may, for example, be fixed to the cylindrical body 5802. The top viewer 581 and the side-wall viewer 583 may be, for example, made of a transparent material. For example, the top viewer 581 and side-wall viewer 583 may be made from glass or a polymeric material, such as polycarbonate, acrylonitrile butadiene styrene, polyurethane, acrylic, or other suitable materials.

In the reaction system 5 provided in the above-described embodiments, EO in the sterilization exhaust gas may be removed by using an acid to adsorb ethylene oxide and to chemically react with EO to produce alcohol. The reaction column 58 may include two gas distributors, a filter screen, and two stirrers, so that the liquid acid substrate and the sterilization exhaust gas can be dispersed and mixed evenly and can make sufficient contact with each other to improve the treatment performance. The interior of the reaction column 58 can be observed in real time through the top viewer and/or through the side-wall viewer. Circulating water may be passed through a sandwich chamber to circularly cool the reaction column 58. The EO concentration detector may be capable of detecting EO concentration in the gas before and after treatment.

Figure 13:
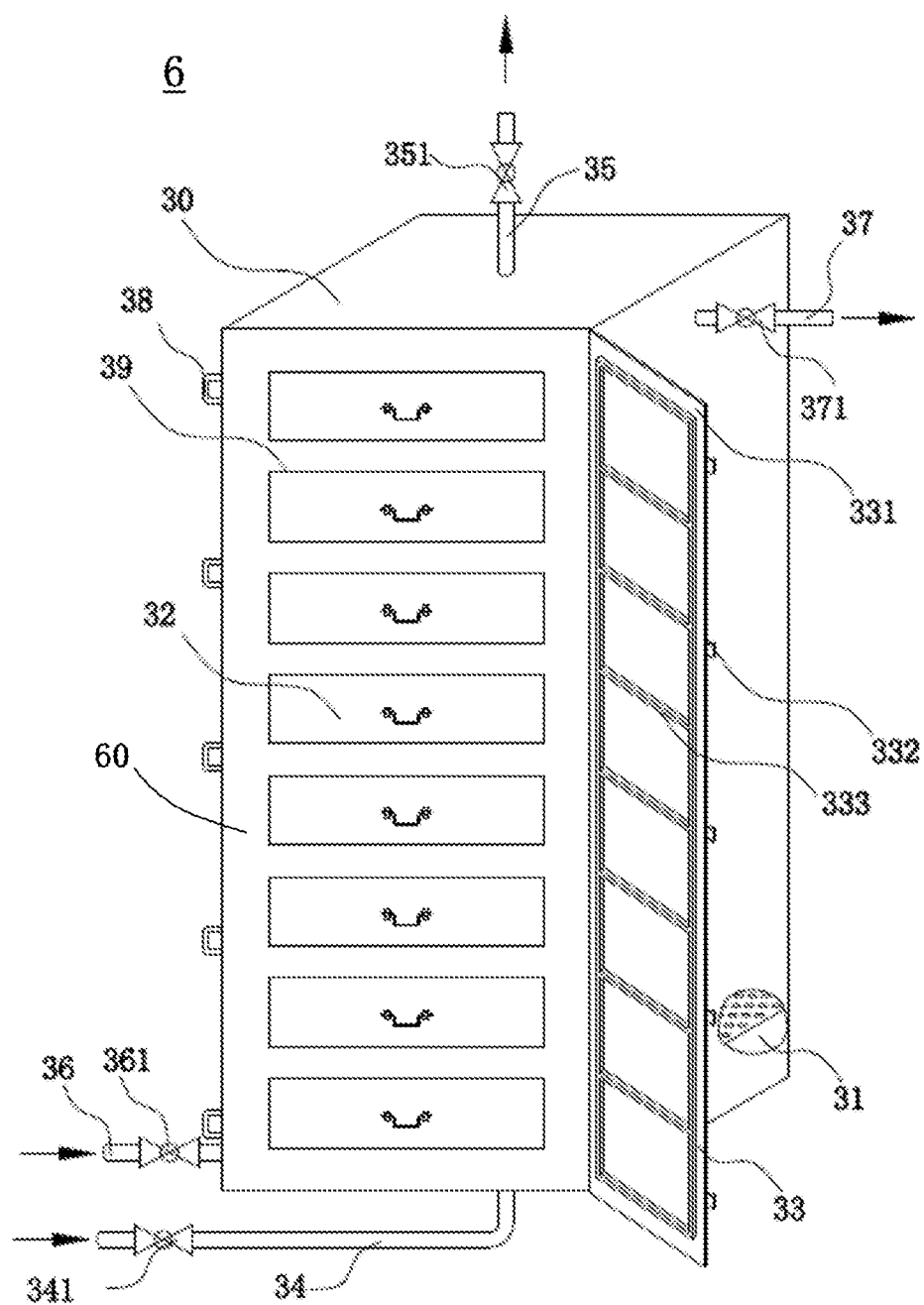
FIG. 13 is a schematic diagram illustrating a temperature swing adsorption recovery system according to an embodiment of the present disclosure.

As shown in FIGS. 13 to 16, in an embodiment, the TSA recovery system 6 may include a temperature swing adsorption column 60. The temperature swing adsorption column 60 may include a column body 30, a sealing door 33, and a plurality of adsorbing structures 32. A gas channel may be formed in the column body 30 extending longitudinally along the height of the column body 30, and the gas channel may have a rectangular cross section, for example. The TSA recovery system 6 may further include a first pipe 34. One end of the first pipe 34 may be provided at a bottom portion of the column body 30 and may fluidly communicate with a bottom portion of the gas channel. The other end of the first pipe 34 may be configured to fluidly communicate with each of the reaction system 5 and the recovery and storage system 12 through corresponding valves. The first pipe 34 is provided with a valve 341, for example. The TSA recovery system 6 may further include a second pipe 35. One end of the second pipe 35 may be provided at a top portion of the column body 30 and may fluidly communicate with the top portion of the gas channel. The second pipe 35 may be provided with a valve 351, for example. The other end of the second pipe 35 may be configured to fluidly communicate with the hydration system 7 through a valve (e.g., fluidly communicate with gas inlet 71 of the hydration system 7 through valve 72). A plurality of adsorbing structures 32 may be provided in the gas channel and may be provided in layers in the longitudinal direction, so that the sterilization exhaust gas to be treated that is input from the first pipe 34 may sequentially pass through the plurality of adsorbing structures 32 and may then be discharged through the second pipe 35. As shown in FIG. 13, a plurality of adsorbing structures 32 may be sequentially provided stacked from the bottom portion to the top portion of the column body 30.

According to some embodiments, the cross section of the gas channel may be substantially rectangular. The side walls of the column body 30 may be provided with mounting holes 39 corresponding to the positions of the respective adsorbing structures 32. The mounting holes 39 may be sequentially provided in the longitudinal direction and may fluidly communicate with the gas channel. Each adsorbing structure 32, in some embodiments, may be similar to a drawer-type structure, may be slidably mounted in the column body 30 through respective mounting holes 39, and may extend into the gas channel. In this way, each adsorbing structure 32 may be slidably extracted from the column body 30, which is convenient for replacement and maintenance.

The side wall of the temperature swing adsorption column 60 that is provided with the mounting holes 39 may be provided with the sealing door 33, which can be opened and closed. When the sealing door 33 is closed, the plurality of mounting holes 39 and the plurality of adsorbing structures 32 may be housed or contained in a sealed environment. When the sealing door 33 is opened, one or more first adsorbing structures 32 of the plurality of adsorbing structures 32 may be taken out from corresponding one or more mounting holes 39 in the column body 30 and/or one or more second adsorbing structures 32 of the plurality of adsorbing structures 32 may be mounted in corresponding one or more mounting holes 39 in the column body 30. Each adsorbing structure 32 may also be provided with a handle for easy withdrawal out of or insertion into its corresponding mounting hole 39 in the column body 30.

The longitudinal edge of one side portion of the sealing door 33 may be mounted on an outer side wall of the column body 30, while the longitudinal edge of the other side portion of the sealing door 33 may be provided with at least one sealing block 332. Further, the sealing door 33 may include a door panel 331 and at least one sealing strip 333. At least one sealing ring 38 may be provided on the other outer side wall of the column body 30. Each of the at least one sealing block 332 may be adapted to interconnect or interlock with a corresponding one of the at least one sealing ring 38 to ensure the tight closure of the sealing door 33. The at least one sealing strip 333 may adhere to an inner side surface of the door panel 331 facing the column body 30 and may be offset from the corresponding position of the drawer-type adsorbing structures 32 or the corresponding position of the mounting holes. When the sealing door 33 is closed, the sealing strip 333 may be pressed against the outer side wall of the column body 30 to enclose the entire area in which the mounting holes 39, and/or any adsorbing structures 32 placed in the mounting holes 39, may be located. Further, the at least one sealing strip 333 may be provided in such a manner that the at least one sealing strip 333 is arranged or distributed in a plurality of sealing loops. When the sealing door 33 is closed, the periphery of each mounting hole 39 (and/or any adsorbing structure 32 places in the mounting hole) is surrounded by a corresponding sealing loop among the plurality of sealing loops.

Figure 14:
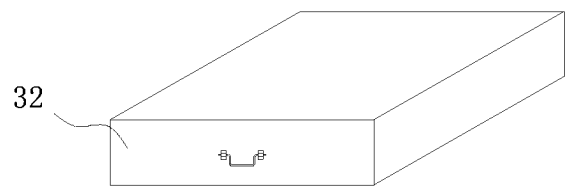
FIG. 14 is a schematic diagram illustrating a drawer-type adsorbing structure that may be used in an adsorption column of the temperature swing adsorption recovery system of FIG. 13.
Figure 15:
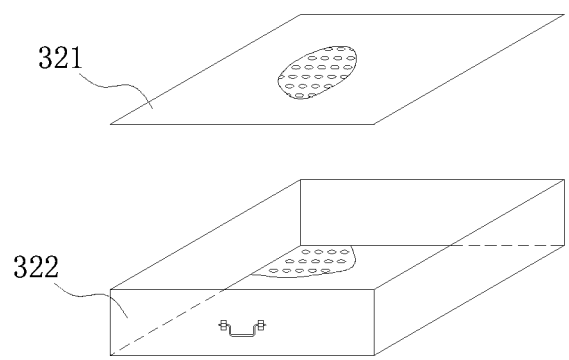
FIG. 15 is a schematic diagram illustrating an exploded view of the drawer-type adsorbing structure of FIG. 14.

With reference to FIGS. 14 and 15, each drawer-type adsorbing structure 32 may include a supporting frame 322, a holder 321, and an adsorbing material for adsorbing ethylene oxide (or other suitable sterilization gas, or the like). According to some embodiments, the supporting frame 322 may have a drawer-type structure, may be slidably connected to the side wall of the gas channel, and may be configured to support the adsorbing material. The holder 321 may be connected to the supporting frame 322 for holding the adsorbing material in the supporting frame 322, to prevent the adsorbing material from being flushed out by the gas flow. The adsorbing material may include, but is not limited to, any one or more of coconut shell activated carbon, columnar activated carbon, activated carbon fiber, silica gel, activated alumina, or molecular sieve, and/or the like, and may be mainly used for adsorbing and desorbing the ethylene oxide in the sterilization exhaust gas. Further, the ratio of the mass of the adsorbing material to the mass of the ethylene oxide may be 0.1-0.15:1.

In some embodiments, the holder 321 may be detachably connected to the supporting frame 322. It can be understood that both the supporting frame 322 and the holder 321 may be made of a ventilating structure. Preferably, the supporting frame 322 may, for example, include, but is not limited to, a box-type supporting frame having an opening at the top, and the adsorbing material may be accommodated in the box body of the box-type supporting frame. The holder 321 may be fixed in the supporting frame 322 for encapsulating the adsorbing material in the box body of the supporting frame 322. The box-type supporting frame 322, especially the bottom plate thereof, may be provided with a plurality of first ventilating holes. The holder 321 may be provided with a plurality of second ventilating holes. The diameters of the first ventilating holes and the second ventilating holes may be smaller than the size of the adsorbing material, thus preventing the adsorbing material from diffusing outward through either or both of the first and/or second ventilating holes (e.g., under impact of gravity and/or under the impact of the gas flow, or the like).

Figure 16:
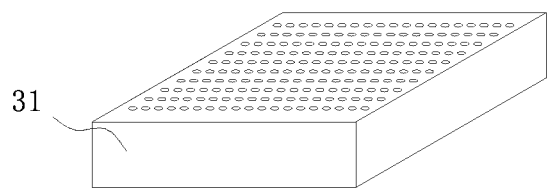
FIG. 16 is a schematic diagram illustrating a gas distributor that may be used in the adsorption column of the temperature swing adsorption recovery system of FIG. 13.
Figure 17:
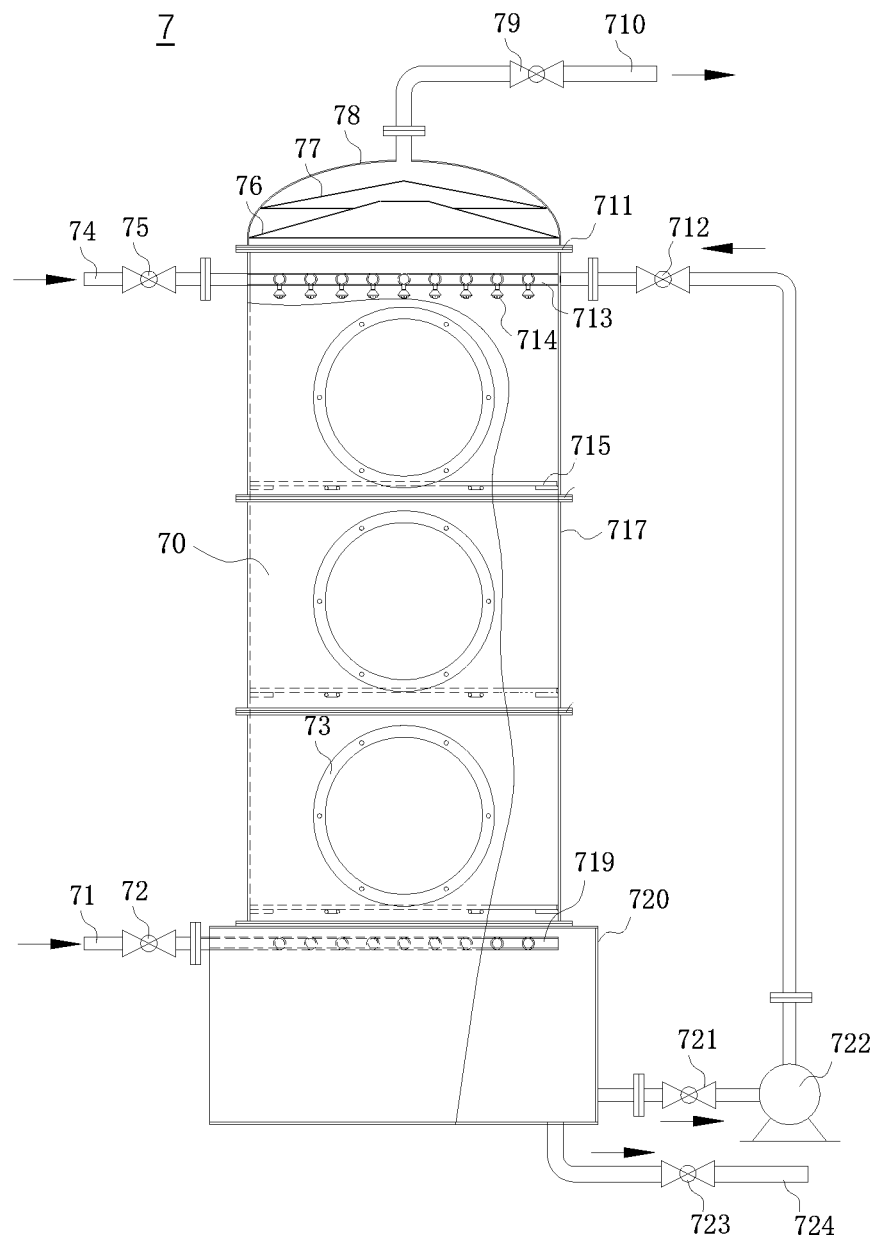
FIG. 17 is a schematic diagram illustrating a hydration system according to an embodiment of the present disclosure.
Figure 18:
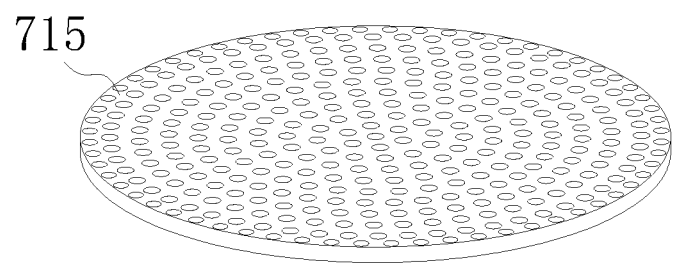
FIG. 18 is a schematic diagram illustrating a gas distributor that may be used in the hydration system of FIG. 17.

Further, referring to FIG. 16, the temperature swing adsorption column 60 may further include a gas distributor 31. The gas distributor 31 may be provided at the bottom portion of the gas channel and may be located below the plurality of adsorbing structures 32. The first pipe 34 may be in fluid communication with the gas distributor 31. The top plate of the gas distributor 31 may be provided with a plurality of small third ventilating holes. The third ventilating holes may be fluidly connected to each of the first pipe 34 and the gas channel. The diameter of the third ventilating hole may be smaller than the size of the adsorbing material. The gas distributor 31 may include, but is not limited to, a box-type structure, and may be used to fill in the bottom space of the gas channel.

The assembly process of the temperature swing adsorption column 60 may be as follows, for example:

The column body 30 may be assembled, and the sealing door 33 may be mounted on the column body 30.

A plurality of adsorbing structures 32 may each be assembled. Specifically, the adsorbing material may be loaded into the box-type supporting frame 322 of each of one or more adsorbing structures 32, and then the corresponding holder 321 may be mounted to press and fix the adsorbing material inside the box-type supporting frame 322 of each of the one or more adsorbing structures 32, so as to prevent the adsorbing material from being flushed out of the adsorbing structure 32, while ensuring the normal flow of the sterilization exhaust gas through the gas channel. The supporting frame 322 and the holder 321 may have arranged or distributed thereon the plurality of first ventilating holes and the plurality of second ventilating holes, respectively. The diameter of each ventilating hole among the first and second ventilating holes may be smaller than the size of the adsorbing material to avoid leakage of the adsorbing material through the first and/or second ventilating holes. The plurality of adsorbing structures 32 may subsequently be slidably mounted into the respective mounting holes 39 of the column body 30.

The gas distributor 31 may be mounted at the bottom portion of the gas channel, below the plurality of adsorbing structures 32. In some alternative embodiments, the gas distributor 31 may be mounted at the bottom portion of the gas channel before at least the mounting of the lowest adsorbing structure 32 in the lowest mounting hole 39 of the column body 30. In some cases, mounting of the gas distributor 31 at the bottom portion of the gas channel may be performed as part of the construction of the column body 30 of the TSA column 60. The top plate of the gas distributor 31 may include a plurality of third ventilating holes. Each third ventilating hole may be a small hole, and the diameter thereof may be smaller than the size of the adsorbing material, thus preventing the adsorbing material from leaking through the third ventilating holes. The gas distributor 31 can disperse the gas evenly, so that the sterilization exhaust gas can be dispersed into the adsorbing material.

The sealing door 33 may be closed and may be locked through interconnection or interlocking of each of the at least one sealing ring 38 and the corresponding one of the at least one sealing block 332, so that the gas channel may be housed or contained in a sealed environment.

According to some embodiments, the TSA recovery system 6 may further include a heat exchanging system for cooling or heating the adsorption column (i.e., the temperature swing adsorption column 60). The heat exchanging system may include, without limitation, a water inlet pipe 36 that may be disposed at the bottom portion of the column body 30, a water outlet pipe 37 that may be disposed at the top portion of the column body 30, and a water circulating interlayer that may be disposed in the column body 30. The water circulating interlayer may be fluidly connected to each of the water inlet pipe 36 and the water outlet pipe 37. In some embodiments, a valve 361 may be provided on the water inlet pipe 36, while a valve 371 may be provided on the water outlet pipe 37, so that cold water or hot water may be directed to enter the water circulating interlayer 36 through the water inlet pipe 36, and to be discharged through the water outlet pipe 37.

In some embodiments, the TSA recovery system 6 may further include a cooling and heating system, which may be fluidly connected to the water inlet pipe 36 and the water outlet pipe 37 to provide cold water circulation or hot water circulation for the heat exchanging system in the column body 30. The cooling and heating system may include a water storage tank located outside the column body 30. The water storage tank may include, but is not limited to, an electric heating tank. The water storage tank may be fluidly connected to the water inlet pipe 36 and the water outlet pipe 37 through a water circulating pipe, so as to continuously circulate cooling or heating water through the column body 30. The reaction system 5, the hydration system 7, and the recovery and storage system 12 may each be connected to the column body 30.

As shown in FIGS. 17 to 22, in an embodiment, the hydration system 7 might include a liquid reservoir 720, a hydration column 70 provided on a top portion of the liquid reservoir 720, and a pump 722. The hydration column 70 may include a column body 717, which may be provided with a gas outlet 710 on top portion thereof for discharging residual gas treated by the hydration column 70 into the fountain device 15.

The column body 717 may be detachably connected or fixedly connected to the liquid reservoir 720, and the column body 717 may be fluidly connected to the pump 722 through a pipe. One side portion of the liquid reservoir 720 may be detachably fluidly connected to the pump 722 through another pipe. A gas inlet 71 may be provided in another side portion of the liquid reservoir 720. A liquid outlet 724 may be provided at a bottom portion of the liquid reservoir 720, and may be fluidly connected to the anaerobic microbial degradation system 9 of the wastewater treatment system 8.

A gas diffuser 719 may be provided inside the liquid reservoir 720, may be fluidly connected to the gas inlet 71, and may further be fluidly connected to the temperature swing adsorption recovery system 6 via the gas inlet 71.

Figure 22A:
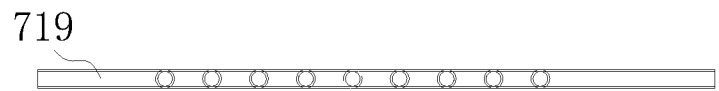
FIG. 22A is a schematic diagram illustrating a front view of a gas diffuser that may be used in the hydration system of FIG. 17.
Figure 22B:
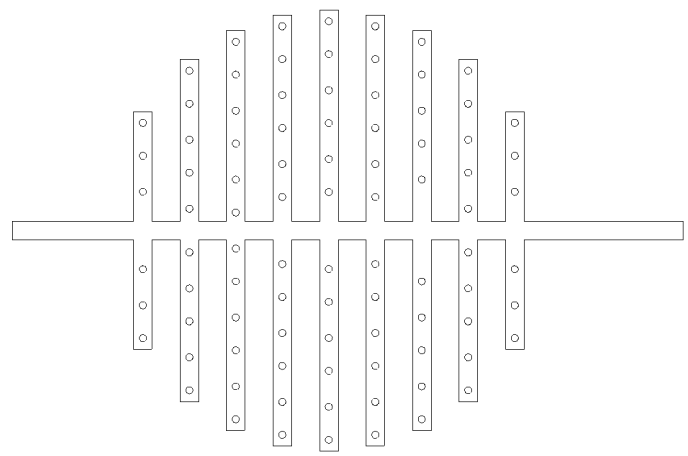
FIG. 22B is a schematic diagram illustrating a top view of the gas diffuser of FIG. 22A.
Figure 22C:
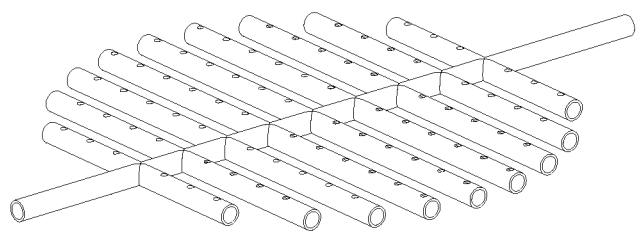
FIG. 22C is a schematic diagram illustrating a top perspective view of the gas diffuser of FIG. 22A.

As shown in FIGS. 22A to 22C, the gas diffuser 719 may include, without limitation, a main pipe and a plurality of auxiliary pipes that fluidly communicate with each other via the main pipe. The plurality of auxiliary pipes may be arranged parallel to each other in a plane and may perpendicularly intersect with the main pipe, and each auxiliary pipe may be symmetrically arranged with respect to the intersection with the main pipe. The auxiliary pipe may be provided with a number of small holes that are evenly arranged or distributed on the upward side facing the hydration column 70. The gas diffuser 719 may facilitate uniformly dispersing the sterilized exhaust gas, such as the sterilized exhaust gas containing ethylene oxide, so that the sterilized exhaust gas containing ethylene oxide may uniformly enter the interior of the hydration column 70 from the bottom portion of the hydration column 70.

Figure 19A:
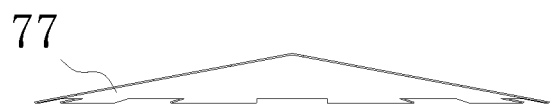
FIG. 19A is a schematic diagram illustrating a front view of a gas guide plate that may be used in the hydration system of FIG. 17.
Figure 19B:
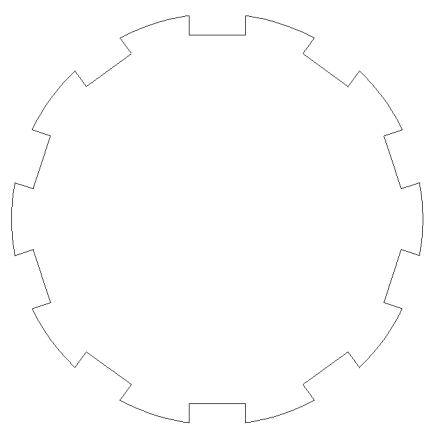
FIG. 19B is a schematic diagram illustrating a top view of the gas guide plate of FIG. 19A.
Figure 20A:
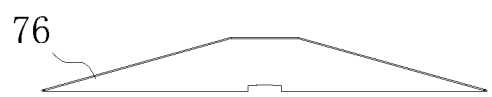
FIG. 20A is a schematic diagram illustrating a front view of a water barrier that may be used in the hydration system of FIG. 17.
Figure 20B:
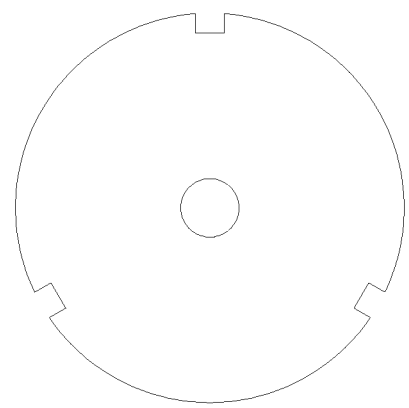
FIG. 20B is a schematic diagram illustrating a top view of the water barrier of FIG. 20A.

Further, in the above-described non-limiting technical solution, the column body 717 may include an upper cover 78 and at least one viewing hole 73. A gas guide plate 77, a water baffle 76, a sealing pad 711, and a sprayer device 713 may be provided in the upper cover 78 (and/or the upper portion of the hydration column 70 or column body 717) in this order from top to bottom. Moreover, the upper cover 78, the gas guide plate 77, the water baffle 76, the sealing pad 711, and the spray device 713 may all be detachably connected to the column body 717. One side portion of the spray device 713 may be fluidly connected to the liquid inlet 74, while the other side portion may be fluidly connected to the liquid reservoir 720 via the pump 722. As shown in FIGS. 19A and 19B, the gas guide plate 77 may include a circular cone surface with a high center and a low circumference, and a plurality of notches may be provided around the circumference of the circular cone surface. As shown in FIGS. 20A and 20B, the water baffle 76 may include a circular cone surface with a middle height and a low circumference. The circular cone surface may be provided with a circular hole in the center thereof, and three notches may be provided around the periphery. In other examples, other numbers of notches may alternatively be provided. The gas guide plate 77 may be convenient for guiding the gas to be discharged from the gas outlet 710. The water baffle 76 may prevent excessive air flow from bringing water out.

Figure 21A:
FIG. 21A is a schematic diagram illustrating a front view of a spray device that may be used in the hydration system of FIG. 17.
Figure 21B:
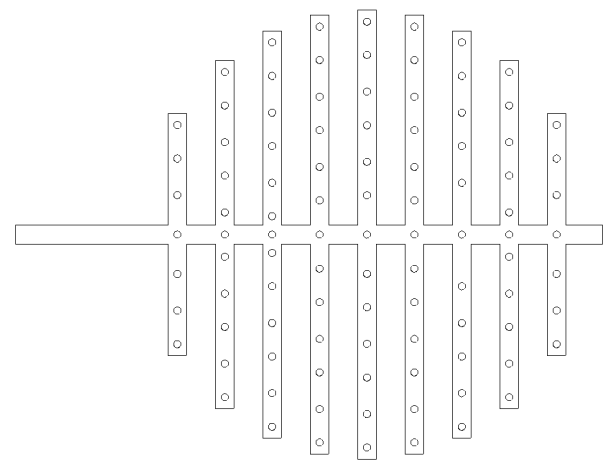
FIG. 21B is a schematic diagram illustrating a top view of the spray device of FIG. 21A.
Figure 21C:
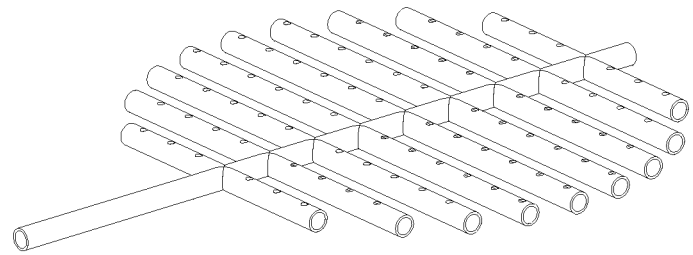
FIG. 21C is a schematic diagram illustrating a top perspective view of the spray device of FIG. 21A.

In some embodiments, the spray device 713 may be provided with a liquid sprayer 714. As shown in FIGS. 21A to 21C, the spray device 713 may include, without limitation, a main pipe and a plurality of auxiliary pipes that fluidly communicate with each other via the main pipe. The plurality of auxiliary pipes may be arranged parallel to each other in a plane and may perpendicularly intersect the main pipe, and each auxiliary pipe may be arranged symmetrically with respect to the intersection with the main pipe. The auxiliary pipe may be provided with a number of small holes that are evenly arranged or distributed on the side facing downward toward the hydration column 70. The spray device 713 and the liquid sprayer 714 might spray liquid (e.g., water or other suitable aqueous solution or liquid, etc.) from the top portion of the hydration column 70 to cover the entire hydration column 70. The sterilization exhaust gas entering the hydration column 70 via the gas inlet 71 and via the gas diffuser 719 can fully make contact with the sprayed liquid, thereby effectively removing the sterilization gas (e.g., such as EO) in the sterilization exhaust gas. In particular, as descending liquid mists and/or droplets meet the ascending sterilization exhaust gas, the ethylene oxide in the sterilization exhaust gas may be absorbed by the liquid (e.g., water, or the like), thereby forming an ethylene oxide exhaust liquor. The ethylene oxide exhaust liquor may fall into a bottom portion of the hydration column 70 to be collected in the liquid reservoir 720, and eventually to be discharged through the liquid outlet 724 to the wastewater treatment system 8.

Further, in the above-described non-limiting technical solution, the at least one viewing hole 73 may include a first viewing hole and a second viewing hole, the first viewing hole being located below the liquid sprayer 714, and the second viewing hole being located at or near the bottom portion of the column body 717 (i.e., located above the gas diffuser 719). In some embodiments, the at least one viewing hole 73 may further include a third viewing hole that may be located between the first viewing hole and the second viewing hole. At least one gas distributor 715 (also referred to as "a gas disperser" or the like) may be provided, including a first gas distributor that may be located below the first viewing hole, a second gas distributor that may be located below the second viewing hole (and above the gas diffuser 719), and a third gas distributor that may be located below the third viewing hole (if present). Both the gas distributor 715 and the at least one viewing hole 73 may be detachably connected to the column body 717.

Further, in the above-described non-limiting technical solution, valves 75, 79, 721, 712, 72, and 723 may respectively be provided on a pipe that is fluidly connected with the liquid inlet 74, a pipe that is fluidly connected with the gas outlet 710, a pipe that is fluidly connected between the liquid reservoir 720 and the pump 722, a pipe that is fluidly connected between the pipe that is fluidly connected with the liquid inlet 74 that is disposed in the hydration column 70 and the pump 722, a pipe that is fluidly connected with the gas inlet 71, and a pipe that is fluidly connected with the liquid outlet 724. These valves can all be automatically controlled, and each step of the operation may be controlled by the automatic control system. As a result, the operation can be made simple, convenient, and fast.

Further, the height and number of hydration columns 70 can be adjusted according to the actual situation.

In an embodiment, the hydration system 7 may include the liquid reservoir 720 (in some cases, embodied as a water pool, or the like). The exhaust gas discharged from the TSA recovery system 6 might enter the liquid reservoir 720 through the second pipe 35 and through gas inlet 71, so that the residual compounds in the exhaust gas, such as ethylene oxide, may be dissolved in the liquid (e.g., water or the like) contained in the liquid reservoir 720.

An embodiment of the present disclosure might provide a method for treating sterilization exhaust gas using the sterilization exhaust gas treatment system of the embodiment of the present disclosure, which may include steps of:

S1, passing the ethylene oxide-containing sterilization exhaust gas into the gas liquefaction recovery system 3; pressurizing the gas liquefaction recovery system 3, so that the ethylene oxide in the ethylene oxide-containing sterilization exhaust gas may be compressed and liquefied to obtain ethylene oxide liquid and treated exhaust gas; and then recovering the ethylene oxide liquid and directing the recovered ethylene oxide liquid to the recovery and storage system 12;

S2, passing the exhaust gas treated by the gas liquefaction recovery system 3 into the PSA recovery system 4 to perform pressurized adsorption and depressurized desorption; and recovering the ethylene oxide gas that may be obtained by the depressurized desorption and directing the recovered ethylene oxide gas to the recovery and storage system 12;

S3, passing the exhaust gas treated by the PSA recovery system 4 into the reaction system 5 to acidize the ethylene oxide in the exhaust gas;

S4, passing the exhaust gas treated by the reaction system 5 into the TSA recovery system 6 for low-temperature adsorption and high-temperature desorption, and recovering the desorbed ethylene oxide gas and directing the recovered desorbed ethylene oxide gas to the recovery and storage system 12;

S5, passing the exhaust gas treated by the TSA recovery system 6 into the hydration system 7, so that the ethylene oxide in the exhaust gas that may be treated by water absorption to obtain wastewater containing ethylene oxide; and S6, inputting the wastewater containing ethylene oxide that may be obtained by the hydration system 7 into the wastewater treatment system 8.

According to some embodiments, in Step S1, the pressure of the exhaust gas after being pressurized in the gas liquefaction recovery system 3 may be between 0.7 MPa and 0.9 MPa, the temperature in the system may be between 20° C. and 30° C., and the concentration of the ethylene oxide-containing sterilization exhaust gas entering the gas liquefaction recovery system 3 may be between 1% Vol and 50% Vol.

In some embodiments, the Step S1 may include steps of:

S11, passing the ethylene oxide-containing sterilization exhaust gas into the gas liquefied separator 19 through the gas inlet 194 through the gas extraction device 17;

S12, pressurizing the interior of the gas liquefaction separator 19 by using the pressurizing device 18, so that the ethylene oxide in the exhaust gas in the gas liquefaction separator 19 may be compressed and liquefied to obtain the ethylene oxide liquid and the treated exhaust gas;

S13, outputting the treated exhaust gas from the gas outlet 198 of the gas liquefaction separator 19 to the PSA recovery system 4; and S14, outputting the ethylene oxide liquid collected by the liquid outlet 197 of the gas liquefaction separator 19 to the recovery and storage system 12.

According to some embodiments, the Step S2 may include steps of:

S21, injecting the exhaust gas treated by the gas liquefaction recovery system 3 into the first PSA column 110 through the first gas vent 111*a*;

S22, pressurizing the gas pressure in the first PSA column 110 to a first preset pressure, so that the ethylene oxide in the exhaust gas may be adsorbed by the adsorbing material 114*c* in the first PSA column 110;

S23, providing fluid communication between the first PSA column 110 and the reaction system 5 through the first gas outlet 111*b*, so that the exhaust gas in the first PSA column 110 may be output to the reaction system 5 through the first gas outlet 111*b*, and depressurizing the gas pressure in the first PSA column 110 to a second preset pressure;

S24, isolating the first gas outlet 111*b* of the first PSA column 110 from the outside portion of the first PSA column 110, and providing fluid communication between the first PSA column 110 and the recovery and storage system 12 through the first gas vent 111*a*, so that the ethylene oxide adsorbed by the adsorbing material in the first PSA column 110 may be desorbed and may enter the recovery and storage system 12 through the first gas vent 111a, and the gas pressure in the first PSA column 110 may be depressurized to a third preset pressure.

In an embodiment, a first preset temperature may be between 20° C. and 30° C. The first preset pressure may be between 0.4 MPa and 0.6 MPa. The second preset pressure may be between 30% and 60% of the first preset pressure. The third preset pressure may be between 0 MPa and 0.2 MPa.

In an embodiment, the Step S2 may further include steps of:

S21', injecting the exhaust gas treated by the gas liquefaction recovery system 3 into the second PSA column 150 through the second gas vent 151a;

S22', pressurizing the gas pressure in the second PSA column 150 to the first preset pressure, so that the ethylene oxide in the exhaust gas may be adsorbed by the adsorbing material 114c in the second PSA column 150;

S23', providing fluid communication between the second PSA column 150 and the reaction system 5 through the second gas outlet 151b, so that the exhaust gas in the second PSA column 150 may be output to the reaction system 5 through the second gas outlet 151b, and depressurizing the gas pressure in the second PSA column 150 to the second preset pressure;

S24', isolating the second gas outlet 151b of the second PSA column 150 from the outside portion of the second PSA column 150, and providing fluid communication between the second PSA column 150 and the recovery and storage system 12 through the second gas vent 151a, so that the ethylene oxide adsorbed by the adsorbing material in the second PSA column 150 may be desorbed and may enter the recovery and storage system 12 through the second gas vent 151a, and the gas pressure in the second PSA column 150 may be depressurized to the third preset pressure.

The Step 'S22' may be performed after the Step S22. The Step 'S23' may be performed after the Step S23. The Step 'S24' may be performed after the Step S24.

In some embodiments, the Step S3 may include treating ethylene oxide that is contained in the exhaust gas with ethylene oxide catalytic concentrate. The amount of the ethylene oxide catalytic concentrate may be calculated based on 0.1 g-0.2 g of ethylene oxide per 1 g of ethylene oxide catalytic concentrate.

According to some embodiments, the adsorbent in the Step S4 may include, but is not limited to, any one or more of coconut shell activated carbon, columnar activated carbon, activated carbon fiber, silica gel, activated alumina, or molecular sieve, and/or the like. In an embodiment, the adsorbent may be activated carbon. The amount of the activated carbon may be calculated based on 0.1 g-0.15 g of ethylene oxide per 1 g of activated carbon. In some embodiments, in the Step S4, the temperature of the low-temperature adsorption may be between 20° C. and 30° C., and the temperature of the high-temperature desorption may be between 70° C. and 90° C.

In some embodiments, the Step S4 may include steps of:

S41, passing the exhaust gas treated by the reaction system 5 into the gas channel of the column body 30 of the adsorption column 60 through the first pipe 34, and cooling the temperature of the adsorption column 60 to a predetermined temperature (such as 20° C.-30° C.) through a heat exchanging system, so that the ethylene oxide in the exhaust gas may be adsorbed by the adsorbing material in the drawer-type adsorbing structure 32;

S42, outputting the exhaust gas passing through the gas channel from the adsorption column to the hydration system 7 through the second pipe 35;

S43, detecting the concentration of ethylene oxide in the exhaust gas of the second pipe 35, and closing the valve of the first pipe 34 when the concentration of ethylene oxide increases to a predetermined concentration (such as 100 ppm or 6% Vol-21% Vol), so that the introduction of exhaust gas into the gas channel may be stopped, and heating the adsorption column to a predetermined temperature (such as 70° C.-90° C.) through the heat exchanging system to desorb the ethylene oxide that has been adsorbed on the adsorbing material;

S44, providing fluid communication between the first pipe 34 and the recovery and storage system 12, and outputting the desorbed ethylene oxide gas to the recovery and storage system 12 through the first pipe 34.

According to some embodiments, the exhaust gas treated by the hydrating treatment in the Step S5 can be used as a nitrogen source. The amount of water used in the hydrating treatment in the Step S5 may be calculated based on 100 g-300 g of ethylene oxide per 1 $m^3$ of water.

In some embodiments, the Step S6 may include steps of:

S61, inputting the wastewater containing ethylene oxide into the anaerobic microbial degradation system 9, so that primary degradation of the ethylene oxide in the wastewater may be performed by the anaerobic microbial ethylene oxide degrading bacteria in the anaerobic microbial degradation system 9;

S62, inputting the wastewater degraded by anaerobic microorganisms of the anaerobic microbial degradation system 9 into the aerobic microbial degradation system 10, so that secondary degradation of the ethylene oxide in the wastewater is performed by the aerobic microbial ethylene oxide degrading bacteria in the aerobic microbial degradation system 10;

S63, inputting the waste water degraded by aerobic microorganisms of the aerobic microbial degradation system 10 into the biological monitoring system 11, so that trace amounts of ethylene oxide remaining in the wastewater may be further purified by the biological monitoring system 11, which monitors the state of microorganisms in the wastewater, thereby monitoring the effect of wastewater treatment.

According to some embodiments, the anaerobic microbial ethylene oxide degrading bacteria might include, without limitation, one or more of *Klebsiella pneumoniae, Clostridium, Clostridium faecalis, Enterococcus, Enterococcus faecalis, Enterobacteriaceae*, or photosynthetic bacteria, and/or the like.

In some embodiments, the *Enterococcus* bacteria might comprise *Enterococcus faecium* strain EO-04 with the Deposit Number of CGMCC No. 18434 or an *Enterococcus faecium* strain comprising the 16S rDNA sequence of SEQ ID NO: 7.

In some embodiments, the *Enterococcus* bacteria might comprise *Enterococcus azikeevi* strain EO-07 with the Deposit Number of CGMCC No. 18437 or an *Enterococcus azikeevi* strain comprising the 16S rDNA sequence of SEQ ID NO: 8.

In some embodiments, the *Clostridium* bacteria might comprise *Clostridium kogasensis* strain EO-08 with the Deposit Number of CGMCC No. 18438 or a *Clostridium kogasensis* strain comprising the 16S rDNA sequence of SEQ ID NO: 10.

In some embodiments, the *Clostridium* bacteria might comprise *Clostridium acidisoli* strain EO-09 with the Deposit Number of CGMCC No. 18439 or a *Clostridium acidisoli* strain comprising the 16S rDNA sequence of SEQ ID NO: 6.

In some embodiments, the *Enterobacteriaceae* bacteria might comprise *Enterobacter roggenkampii* strain EO-10 with the Deposit Number of CGMCC No. 18440 or an *Enterobacter roggenkampii* strain comprising the 16S rDNA sequence of SEQ ID NO: 9.

The foregoing strains and other strains mentioned below were deposited at China General Microbiological Culture Collection Center, with the deposit address being Institute of Microbiology of Chinese Academy of Sciences, NO. 1 West Beichen Road, Beijing 100101, China.

According to some embodiments, the aerobic microbial ethylene oxide degrading bacteria might include, without limitation, one or more of *Acetobacter peroxydans, Escherichia coli, Cycloclasticus, Bacillus,* or *Pseudomonas aeruginosa*, and/or the like.

In some embodiments, the *Acetobacter peroxydans* bacteria might comprise *Acetobacter peroxydans* strain EO-01 with the Deposit Number of CGMCC No. 18431 or an *Acetobacter peroxydans* strain comprising the 16S rDNA sequence of SEQ ID NO: 2.

In some embodiments, the *Bacillus* bacteria might comprise *Bacillus subtilis* strain EO-03 with the Deposit Number of CGMCC No. 18433 or a *Bacillus subtilis* strain comprising the 16S rDNA sequence of SEQ ID NO: 4.

According to some embodiments, the microbial ethylene oxide degrading bacteria might also include, without limitation, one or more of *Lactobacillus, Alcaligenes,* and *Kurthia* strains, and/or the like.

In some embodiments, the *Lactobacillus* bacteria might comprise *Lactobacillus fermentum* strain EO-02 with the Deposit Number of CGMCC No. 18432 or a *Lactobacillus fermentum* strain comprising the 16S rDNA sequence of SEQ ID NO: 3.

In some embodiments, the *Alcaligenes* bacteria might comprise *Alcaligenes faecalis* strain EO-05 with the Deposit Number of CGMCC No. 18435 or an *Alcaligenes faecalis* strain comprising the 16S rDNA sequence of SEQ ID NO: 1.

In some embodiments, the *Kurthia gibsonii* bacteria might comprise *Kurthia gibsonii* strain EO-06 with the Deposit Number of CGMCC No. 18436 or a *Kurthia gibsonii* strain comprising the 16S rDNA sequence of SEQ ID NO: 5.

In some embodiments, the biological monitoring system may be a small ecosystem randomly composed of plankton, aquatic plants, leeches, loach, snails, shrimps, fish, ducks, geese, and/or other visible organisms.

It may be apparent from the above-described technical solutions that the beneficial effects of the technical solutions of the present disclosure may be as follows, although not limited to these beneficial effects: a combined system including multiple treatment processes of physics, chemistry, and biology, so that the ethylene oxide-containing sterilization exhaust gas of different concentrations may be treated in multiple stages, so as to achieve a very low concentration of ethylene oxide in the exhaust gas and wastewater, and to achieve the recycling and harmless gas treatment of ethylene oxide-containing sterilization exhaust gas.

The adsorbing material selected in the present disclosure can be reused, which has the characteristics of: saving resources; reducing costs; providing economic and environmental protection; providing reasonable structure; providing safe, reliable, and simple operation; achieving good treatment effect; having great significance for the development and application of ethylene oxide sterilization; improving the level of medical sterilization as a whole; achieving realization of the harmless gas treatment of ethylene oxide-containing sterilization exhaust gas; and enabling protection of the environment.

According to the disclosure, the ethylene oxide-containing sterilization exhaust gas with a concentration of 1% Vol-50% Vol in the ethylene oxide gas sterilization device and a concentration of 0-200 ppm in the volatile chamber 2 may be treated by the sterilization exhaust gas treatment system, and the highest recovery concentration can reach 99.99% Vol and the recovery rate can reach 70%. The concentration of ethylene oxide in the exhaust gas may be less than 10 ppm.

EXAMPLES 1-5

A treatment method of ethylene oxide-containing sterilization exhaust gas, specifically, may include steps of:

(a) passing the ethylene oxide-containing sterilization exhaust gas in the gas sterilization device 1 into the gas liquefaction recovery system 3, and compressing the ethylene oxide-containing sterilization exhaust gas at 20° C.-30° C. to 0.8 MPa, and recovering the resultant pure ethylene oxide liquid and directing the ethylene oxide liquid to the recovery and storage system 12 through an ethylene oxide recovery pipeline 13 for later use;

(b) passing the ethylene oxide-containing sterilization exhaust gas that may be remaining after the compression and recovery treatments into the PSA recovery system 4. According to some embodiments, the adsorbing material may be 13× molecular sieve, which is beige and has a pore size of 10 A, a spherical shape, a particle size of 1.7 mm-2.5 mm, and a bulk density of 0.7 g/mL. The amount of the molecular sieve may be calculated based on treatment capacity of 0.1 g of ethylene oxide per 1 g of molecular sieve. The sterilization exhaust gas may be pressurized to 0.5 MPa for adsorption, and depressurized to 0 MPa for desorption and recovery. The high-concentration ethylene oxide gas may be recovered and may be directed to the recovery and storage system 12 through the ethylene oxide recovery pipeline 13 for later use;

(c) passing the ethylene oxide-containing sterilization exhaust gas that may be remaining after the pressure swing adsorption recovery treatment into the reaction system 5, and using ethylene oxide catalytic concentrate to subject the ethylene oxide in the sterilization exhaust gas to physical adsorption and chemical reaction, wherein the amount of ethylene oxide catalytic concentrate may be calculated based on the treatment capacity of 0.1 g of ethylene oxide per 1 g of ethylene oxide catalytic concentrate.

(d) passing the remaining low-concentration ethylene oxide sterilization gas treated by the acidization into the TSA recovery system 6. According to some embodiments, the amount of activated carbon may be calculated based on 0.1 g of ethylene oxide per 1 g of activated carbon treatment capacity. The sterilization exhaust gas may be subjected to low-temperature (20° C.-30° C.) adsorption and high-temperature (70° C.-90° C.) desorption recovery treatment by the activated carbon. When the exhaust gas concentration rises to 100 ppm, the input of mixed gas may be stopped, the cooling water may be stopped, and desorption may begin. The desorbed high-concentration ethylene oxide gas may be recovered and directed through ethylene oxide recovery pipeline 13 to recovery and storage system 12 for later use;

(e) passing the remaining low-concentration ethylene oxide sterilization gas that has been subjected to the adsorption and recovery treatment and the ethylene oxide exhaust gas in the volatile chamber 2 (ethylene oxide having a concentration of 0 ppm-200 ppm) into the hydration system 7, and subjecting the ethylene oxide gas to a water adsorption treatment. According to some embodiments, the amount of the water may be calculated based on 200 g of ethylene oxide per 1 $m^3$ of water treatment capacity;

(f) passing the wastewater containing ethylene oxide that has been subjected to the hydrating treatment into the anaerobic microbial degradation system 9 through an ethylene oxide wastewater pipeline, so that the anaerobic microbial ethylene oxide degrading bacteria may perform a primary degradation treatment on the ethylene oxide in the wastewater. The exhaust gas that has been subjected to the hydrating treatment may then enter the fountain device 15 through an exhaust pipeline 16;

According to some embodiments, the wastewater containing ethylene oxide that may be degraded by anaerobic microorganisms may enter into the aerobic microbial degradation system 10. The aerobic microorganism ethylene oxide degrading bacteria may perform a secondary degradation treatment on the ethylene oxide in the wastewater;

The wastewater containing ethylene oxide that has been treated by microbial degradation systems may then enter the biological monitoring system 11. As a small ecosystem, the biological monitoring system 11 may further purify the trace amount of ethylene oxide remaining in the water, and may monitor the effect of the wastewater treatment through monitoring of the biological living state;

The non-polluted water that has been treated by the biological monitoring system may then enter the fountain device 15; and (g) passing the ethylene oxide from the recovery and storage system 12 into the gas sterilization device 1 through an ethylene oxide inlet pipeline to be sterilized and recovered again.

According to some embodiments, the concentrations of ethylene oxide in the ethylene oxide-containing sterilization exhaust gas in Step (a) of Examples 1 to 5 correspond to 50.78 Vol %, 27.77 Vol %, 15.66 Vol %, 5.12 Vol %, and 1.22 Vol %, respectively. The concentration of ethylene oxide in each residual gas may be detected, respectively. The concentration of the ethylene oxide in the recovered ethylene oxide gas may be detected, and the results are shown in Table 1-5;

Method for detecting the content of ethylene oxide in ethylene oxide-containing sterilization exhaust gas may be as follows:

(1) Gas Chromatography Detection: Sampling Detection
Instrument: Gas chromatograph Agilent 7890B;
Chromatography column: FFAP quartz capillary column (25 m×0.25 mm×0.25 μm);
Temperature: column temperature may be maintained at 45° C. for 7 minutes, then may be increased to 120° C. at 15° C./min, and then maintained for 7 minutes; the temperature at the sample inlet may be 130° C.; the temperature at the detector may be 150° C.;
Carrier gas: nitrogen 2 mL/min, hydrogen 35 mL/min, air 400 mL/min;
Sample introduction: automatic, gas sample 1 mL;
Detector: hydrogen flame ionization detector (FID).

(2) Ethylene oxide concentration detector: online real-time detection of the concentration of the ethylene oxide gas in pipelines.

Instrument: online ethylene oxide concentration detector thermal conductivity MIC-500s-ETO (0-99% Vol, resolution 0.01% Vol);

Fixed-type ethylene oxide alarm detector electrochemistry JSA5-ETO-AX (0-100 ppm, resolution 0.01 ppm);

online ethylene oxide concentration detector (PID) (0-2000 ppm, resolution 0.1 ppm).

TABLE 1

Results of 50.78 Vol % of ethylene oxide treated by each treatment system

| Treatment system | Concentration of the ethylene oxide | |
|---|---|---|
| | Before treatment | After treatment |
| Gas liquefaction recovery system | 50.78 Vol % | 27.12 Vol % |
| PSA recovery system | 27.12 Vol % | 5.44 Vol % |
| Reaction system | 5.44 Vol % | 1.24 Vol % |
| TSA recovery system | 1.24 Vol % | 100 ppm |
| Hydration system (volatile chamber 200 ppm) | 300 ppm | <10 ppm |
| Anaerobic microbial degradation system | <160 mg/L | <50 mg/L |
| Aerobic microbial degradation system | <50 mg/L | <21 mg/L |
| Biological monitoring system | <21 mg/L | <10 mg/L |

As shown in Table 1, after the ethylene oxide-containing sterilization exhaust gas has been treated by the sterilization exhaust gas treatment system, the concentration of ethylene oxide in the exhaust gas gradually decreases. Finally, the concentration of ethylene oxide in the exhaust gas may be less than 10 ppm, and the concentration of ethylene oxide in the wastewater may be less than 10 mg/L. More than 99.99% of ethylene oxide in the sterilization exhaust gas may be treated and removed. According to some embodiments, the gas liquefaction recovery system 3 may compress and liquefy the ethylene oxide in the sterilization exhaust gas at 0.8 MPa. The purity of the ethylene oxide can reach 99.99 Vol %, and the ethylene oxide may be recovered. During the recovery, part of the mixed gas may also be recovered, and the gas liquefaction recovery system 3 can recover 46.48% of the ethylene oxide in the sterilization exhaust gas, and the average recovery concentration can reach 85.56 Vol %. The PSA recovery system 4 can recover 48.81% of the ethylene oxide in the sterilization exhaust gas remaining after the compression and recovery treatments, and the concentration of the recovered ethylene oxide gas can reach 45.25 Vol %. In total, about 70.34% of the ethylene oxide in the sterilization exhaust gas can be recovered and reused.

TABLE 2

Results of 27.77 Vol % of ethylene oxide treated by each treatment system

| Treatment system | Concentration of the ethylene oxide | |
|---|---|---|
| | Before treatment | After treatment |
| Gas liquefaction recovery system | 27.77 Vol % | 26.68 Vol % |
| PSA recovery system | 26.68 Vol % | 4.85 Vol % |
| Reaction system | 4.85 Vol % | 1.11 Vol % |
| TSA recovery system | 1.11 Vol % | 100 ppm |
| Hydration system (volatile chamber 200 ppm) | 300 ppm | <10 ppm |
| Anaerobic microbial degradation system | <160 mg/L | <50 mg/L |

TABLE 2-continued

Results of 27.77 Vol % of ethylene oxide treated by each treatment system

| Treatment system | Concentration of the ethylene oxide | |
|---|---|---|
| | Before treatment | After treatment |
| Aerobic microbial degradation system | <50 mg/L | <21 mg/L |
| Biological monitoring system | <21 mg/L | <10 mg/L |

As shown in Table 2, after the sterilization exhaust gas has been treated by the sterilization exhaust gas treatment system, the concentration of ethylene oxide in the exhaust gas gradually decreases. Finally, the concentration of ethylene oxide in the exhaust gas may be less than 10 ppm, and the concentration of ethylene oxide in the wastewater may be less than 10 mg/L. More than 99.99% of ethylene oxide in the sterilization exhaust gas may be treated and removed. According to some embodiments, at 0.8 MPa pressure and room temperature, the compressed gas-liquid equilibrium concentration of ethylene oxide may be about 27 Vol %. Therefore, the concentration of 27.77 Vol % of ethylene oxide-containing sterilization exhaust gas may be basically unchanged after being treated by the gas liquefaction recovery system 3. The sterilization gas may directly enter the PSA recovery system 4. The pressure swing adsorption recovery treatment can recover 48.01% of the ethylene oxide in the sterilization exhaust gas, and the concentration of the recovered ethylene oxide gas can reach 45.44 Vol %.

TABLE 3

Results of 15.66 Vol % of ethylene oxide treated by each treatment system

| Treatment system | Concentration of the ethylene oxide | |
|---|---|---|
| | Before treatment | After treatment |
| Gas liquefaction recovery system | — | — |
| PSA recovery system | 15.66 Vol % | 3.31 Vol % |
| Reaction system | 3.31 Vol % | 0.52 Vol % |
| TSA recovery system | 0.52 Vol % | <100 ppm |
| Hydration system (volatile chamber 200 ppm) | 300 ppm | <10 ppm |
| Anaerobic microbial degradation system | <160 mg/L | <50 mg/L |
| Aerobic microbial degradation system | <50 mg/L | <21 mg/L |
| Biological monitoring system | <21 mg/L | <10 mg/L |

As shown in Table 3, after the sterilization exhaust gas has been treated by the sterilization exhaust gas treatment system, the concentration of ethylene oxide in the exhaust gas gradually decreases. Finally, the concentration of ethylene oxide in the exhaust gas may be less than 10 ppm, and the concentration of ethylene oxide in the wastewater may be less than 10 mg/L. More than 99.99% of ethylene oxide in the sterilization exhaust gas may be treated and removed. According to some embodiments, 15.66 Vol % of ethylene oxide-containing sterilization exhaust gas may be treated by a PSA recovery system 4, 45.34% of the ethylene oxide in the sterilization exhaust gas can be recovered and reused, and the concentration of the recovered ethylene oxide gas can reach 30.08 Vol %.

TABLE 4

Results of 5.12 Vol % of ethylene oxide treated by each treatment system

| Treatment system | Concentration of the ethylene oxide | |
|---|---|---|
| | Before treatment | After treatment |
| Gas liquefaction recovery system | — | — |
| PSA recovery system | — | — |
| Reaction system | 5.12 Vol % | 1.13 Vol % |
| TSA recovery system | 1.13 Vol % | 100 ppm |
| Hydration system (volatile chamber 200 ppm) | 300 ppm | <10 ppm |
| Anaerobic microbial degradation system | <160 mg/L | <50 mg/L |
| Aerobic microbial degradation system | <50 mg/L | <21 mg/L |
| Biological monitoring system | <21 mg/L | <10 mg/L |

As shown in Table 4, after the sterilization exhaust gas has been treated by the sterilization exhaust gas treatment system, the concentration of ethylene oxide in the exhaust gas gradually decreases. Finally, the concentration of ethylene oxide in the exhaust gas may be less than 10 ppm, and the concentration of ethylene oxide in the wastewater may be less than 10 mg/L. More than 99.99% of ethylene oxide in the sterilization exhaust gas may be treated and removed.

TABLE 5

Results of 1.22 Vol % of ethylene oxide treated by each treatment system

| Treatment system | Concentration of the ethylene oxide | |
|---|---|---|
| | Before treatment | After treatment |
| Gas liquefaction recovery system | — | — |
| PSA recovery system | — | — |
| Reaction system | — | — |
| TSA recovery system | 1.22 Vol % | 100 ppm |
| Hydration system (volatile chamber 200 ppm) | 300 ppm | <10 ppm |
| Anaerobic microbial degradation system | <160 mg/L | <50 mg/L |
| Aerobic microbial degradation system | <50 mg/L | <21 mg/L |
| Biological monitoring system | <21 mg/L | <10 mg/L |

As shown in Table 5, after the sterilization exhaust gas has been treated by the sterilization exhaust gas treatment system, the concentration of ethylene oxide in the exhaust gas gradually decreases. Finally, the concentration of ethylene oxide in the exhaust gas may be less than 10 ppm, and the concentration of ethylene oxide in the wastewater may be less than 10 mg/L. More than 99.99% of ethylene oxide in the sterilization exhaust gas may be treated and removed.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A sterilization exhaust gas treatment system, comprising:
   a gas liquefaction recovery system;
   a pressure swing adsorption recovery system;
   a reaction system;
   a temperature swing adsorption recovery system;
   a hydration system;
   a recovery and storage system; and
   a wastewater treatment system;
   wherein the gas liquefaction recovery system, the pressure swing adsorption recovery system, the reaction system, the temperature swing adsorption recovery system, and the hydration system are fluidly connected in sequence through one or more first connecting pipes;
   wherein the gas liquefaction recovery system, the pressure swing adsorption recovery system, and the temperature swing adsorption recovery system are each fluidly connected to the recovery and storage system through one or more second connecting pipes; and
   wherein the hydration system is fluidly connected to the wastewater treatment system through one or more wastewater pipes.

2. The sterilization exhaust gas treatment system according to claim 1, having a feature selected from the group consisting of:
   a) wherein the wastewater treatment system comprises:
      an anaerobic microbial degradation system, an aerobic microbial degradation system, and a biological monitoring system; and
      wherein the hydration system, the anaerobic microbial degradation system, the aerobic microbial degradation system, and the biological monitoring system are fluidly connected in sequence through the one or more wastewater pipes;
   b) wherein the gas liquefaction recovery system comprises:
      a gas liquefaction separator;
      a gas intake pipe;
      a pressurizing device; and
      a gas extraction device;
      wherein a gas inlet of the gas liquefaction separator is fluidly connected to the gas intake pipe;
      wherein the pressurizing device and the gas extraction device are disposed on the gas intake pipe;
      wherein a gas outlet of the gas liquefaction separator is fluidly connected to the pressure swing adsorption recovery system; and
      wherein a liquid outlet of the gas liquefaction separator is fluidly connected to the recovery and storage system;
   c) wherein the pressure swing adsorption recovery system comprises:
      a first pressure swing adsorption column including a first accommodating chamber, a first gas vent, and a first gas outlet, the first gas vent and the first gas outlet being in fluid communication with the first accommodating chamber, wherein the first accommodating chamber is configured to accommodate an adsorbing material;
      a first thermostatic assembly, wherein the first pressure swing adsorption column is at least partially provided near the first thermostatic assembly;
      a first branch pipe; and
      a second branch pipe, the first branch pipe and the second branch pipe each being configured to fluidly communicate with the first gas vent;
      wherein the first branch pipe is configured to provide fluid communication between the first gas vent and the recovery and storage system;
      wherein the second branch pipe is configured to provide fluid communication between the first gas vent and a gas outlet of the gas liquefaction recovery system; and
      wherein the first gas outlet is in fluid communication with the reaction system;
   d) wherein the reaction system comprises a reaction column comprising:

a column body, with an inner cavity configured for containing a liquid substrate;

wherein the column body has a bottom portion that is provided with a gas inlet pipe and a liquid outlet pipe, wherein the gas inlet pipe is configured to inject ethylene oxide-containing sterilization exhaust gas into the inner cavity, and wherein the liquid outlet pipe is configured to discharge, from the inner cavity, the liquid substrate that has been used to catalyze ethylene oxide in ethylene oxide-containing sterilization exhaust gas;

wherein the column body has a top portion that is provided with a gas outlet pipe with a gas inlet that is disposed above a liquid level of the liquid substrate; and at least one gas distributor, which is provided in the inner cavity above a gas outlet of the gas inlet pipe, is configured to disperse the ethylene oxide-containing sterilization exhaust gas that is injected into the inner cavity via the gas inlet pipe;

e) wherein the temperature swing adsorption recovery system comprises:

an adsorption column comprising a column body, a sealing door, and a plurality of adsorbing structures;

a first pipe;

a second pipe; and a heat exchanging system that is configured to cool or to heat the adsorption column;

wherein a gas channel is formed in the column body, extending longitudinally in the column body, wherein a side wall of at least one side portion of the column body is provided with a plurality of mounting holes, wherein each of the plurality of mounting holes is sequentially provided in a longitudinal direction and fluidly communicates with the gas channel;

wherein one end of the first pipe is provided at a bottom portion of the column body and fluidly communicates with a bottom portion of the gas channel, wherein the other end of the first pipe is configured to fluidly communicate with each of the reaction system and the recovery and storage system;

wherein one end of the second pipe is provided at a top portion of the column body and fluidly communicates with a top portion of the gas channel, wherein the other end of the second pipe is configured to fluidly communicate with the hydration system;

wherein the plurality of adsorbing structures extends into the gas channel, and is respectively slidably mounted on the column body through respective mounting holes; and wherein the sealing door is mounted on the side wall of the at least one side portion of the column body, and is capable of being opened and closed, and wherein, when the sealing door is closed, the plurality of mounting holes and the plurality of adsorbing structures are housed in a sealed environment; and f) wherein the hydration system comprises:

a liquid reservoir;

a hydration column, the hydration column being provided on a top portion of the liquid reservoir; and a pump;

wherein one side portion of the liquid reservoir is fluidly connected to the pump via a first pipeline, and the pump is fluidly connected to the hydration column via a second pipeline;

wherein a bottom portion of the liquid reservoir is provided with a liquid outlet for fluidly connecting with the wastewater treatment system, wherein an air inlet is provided on a side portion of the liquid reservoir for fluidly connecting with the temperature swing adsorption recovery system, and wherein a gas diffuser is provided in an interior of the liquid reservoir, and is fluidly connected with the air inlet; and wherein the hydration column comprises a column body provided with a gas outlet on top thereof for discharging residual gas treated by the hydration column, wherein a spray device is arranged in an upper portion inside the column body and is fluidly connected to the pump via a pipeline, and wherein a gas distributor is provided below the spray device.

3. The sterilization exhaust gas treatment system according to claim 1, further comprising a part selected from the group consisting of:

a) a gas sterilization device;

wherein the gas liquefaction recovery system and the hydration system are each fluidly connected to the gas sterilization device through one or more gas sterilization pipes; and b) a fountain device;

wherein the hydration system and the wastewater treatment system are each fluidly connected to the fountain device through one or more fountain connection pipes.

4. The sterilization exhaust gas treatment system according to claim 1, wherein the gas liquefaction recovery system comprises:

a gas liquefaction separator;

a gas intake pipe;

a pressurizing device; and a gas extraction device;

a housing, wherein the housing comprises a gas outlet that is provided at a top portion of the housing, a gas inlet that is provided at an inner side wall of the housing, and a liquid outlet that is provided at a bottom portion of the housing;

a blocking plate, wherein the blocking plate extends downward from a top wall of an inner cavity of the housing, wherein the gas inlet is opposite to the blocking plate;

a gas baffle, wherein the gas baffle is located below the blocking plate; and a liquid collector, wherein the liquid collector is located below the gas baffle, wherein an outer edge of the liquid collector is connected to the inner side wall of the housing;

wherein a gas inlet of the gas liquefaction separator is fluidly connected to the gas intake pipe;

wherein the pressurizing device and the gas extraction device are disposed on the gas intake pipe;

wherein a gas outlet of the gas liquefaction separator is fluidly connected to the pressure swing adsorption recovery system; and wherein a liquid outlet of the gas liquefaction separator is fluidly connected to the recovery and storage system;

wherein the blocking plate, the gas baffle, and the liquid collector are located in the housing;

wherein the liquid collector comprises a first flow guide surface, wherein a bottom portion of the first flow guide surface is provided with a first hole; and wherein an upper surface of the gas baffle forms a second flow guide surface, wherein an outer edge of the gas baffle is provided with at least one protrusion, and wherein the gas baffle is connected to the first flow guide surface through the at least one protrusion, thereby forming a second hole between the outer edge of the gas baffle and the first flow guide surface.

5. The sterilization exhaust gas treatment system according to claim 4, having a feature selected from the group consisting of:
   a) wherein the inner cavity of the housing comprises:
      an upstream chamber;
      a downstream chamber; and
      a lower chamber, the upstream chamber and the downstream chamber being divided by the blocking plate, and the lower chamber being located below the blocking plate;
      wherein a bottom portion of the upstream chamber and a bottom portion of the downstream chamber are in fluid communication with each other through the lower chamber;
      wherein the gas inlet corresponds to the upstream chamber, wherein the gas outlet corresponds to the downstream chamber, and wherein the liquid outlet corresponds to the lower chamber; and
      wherein the gas baffle is located in the lower chamber, and wherein the liquid collector is located in the lower chamber; and
   b) wherein the second flow guide surface has a shape with a higher middle portion and lower edges; wherein the at least one protrusion comprises a plurality of protrusions; and wherein the plurality of protrusions is arranged such that they are spaced apart from each other along a circumference of the gas baffle.

6. The sterilization exhaust gas treatment system according to claim 1, wherein the pressure swing adsorption recovery system comprises:
   a first pressure swing adsorption column including a first accommodating chamber, a first gas vent, and a first gas outlet, the first gas vent and the first gas outlet being in fluid communication with the first accommodating chamber, wherein the first accommodating chamber is configured to accommodate an adsorbing material;
   a first thermostatic assembly, wherein the first pressure swing adsorption column is at least partially provided near the first thermostatic assembly;
   a first branch pipe; and
   a second branch pipe, the first branch pipe and the second branch pipe each being configured to fluidly communicate with the first gas vent;
   wherein the first branch pipe is configured to provide fluid communication between the first gas vent and the recovery and storage system;
   wherein the second branch pipe is configured to provide fluid communication between the first gas vent and a gas outlet of the gas liquefaction recovery system;
   wherein the first gas outlet is in fluid communication with the reaction system, and further comprising:
      a second pressure swing adsorption column, including a second accommodating chamber, a second gas vent, and a second gas outlet, the second gas vent and the second gas outlet being in fluid communication with the second accommodating chamber, wherein the second accommodating chamber is configured to accommodate the adsorbing material;
      a second thermostatic assembly, wherein the second pressure swing adsorption column is at least partially provided near the second thermostatic assembly;
      a third branch pipe; and
      a fourth branch pipe;
   wherein the third branch pipe is configured to provide fluid communication between the second gas vent and the recovery and storage system;
   wherein the fourth branch pipe is configured to provide fluid communication between the second gas vent and the gas outlet of the gas liquefaction recovery system;
   wherein the second gas outlet is in fluid communication with the reaction system;
   wherein the first pressure swing adsorption column comprises:
      a first column body;
      a first upper sealing cover; and
      a first lower sealing cover, the first upper sealing cover and the first lower sealing cover being connected to top and bottom ends of the first column body, respectively;
   wherein the first accommodating chamber is enclosed by the first column body, the first upper sealing cover, and the first lower sealing cover; and
   wherein a water-absorbing material and an oil-absorbing material are sequentially provided between the first lower sealing cover and the adsorbing material along a direction close to the adsorbing material.

7. The sterilization exhaust gas treatment system according to claim 6, wherein:
   a first-stage gas distributor is provided between the first lower sealing cover and the water-absorbing material, wherein the first-stage gas distributor is provided with a plurality of holes, and wherein a diameter of the holes is smaller than a particle size of the water-absorbing material; and
   a second-stage gas distributor is provided between the water-absorbing material and the oil-absorbing material, wherein a lower mesh plate is provided between the oil-absorbing material and the adsorbing material.

8. The sterilization exhaust gas treatment system according to claim 1, wherein the reaction system comprises a reaction column comprising:
   a column body, with an inner cavity configured for containing a liquid substrate;
   wherein the column body has a bottom portion that is provided with a gas inlet pipe and a liquid outlet pipe, wherein the gas inlet pipe is configured to inject ethylene oxide-containing sterilization exhaust gas into the inner cavity, and wherein the liquid outlet pipe is configured to discharge, from the inner cavity, the liquid substrate that has been used to catalyze ethylene oxide in ethylene oxide-containing sterilization exhaust gas;
   wherein the column body has a top portion that is provided with a gas outlet pipe with a gas inlet that is disposed above a liquid level of the liquid substrate;
   at least one gas distributor, which is provided in the inner cavity above a gas outlet of the gas inlet pipe, is configured to disperse the ethylene oxide-containing sterilization exhaust gas that is injected into the inner cavity via the gas inlet pipe; and
   wherein the at least one gas distributor comprises a first gas distributor, the first gas distributor being a curved plate with a center and an edge, the center being high and the edge being low relative to each other; wherein the edge of the curved plate is connected to a bottom wall of the inner cavity; wherein the curved plate is provided with a plurality of first air holes in an annular arrangement; wherein the gas inlet pipe fluidly communicates with the gas outlet pipe through the plurality of first air holes; and wherein the plurality of first air holes gradually increases in hole size in a direction from the center to the edge of the curved plate.

9. The sterilization exhaust gas treatment system according to claim 8, wherein the at least one gas distributor further comprises a second gas distributor, the second gas distributor being a flat plate with a center and an edge, and being located above the first gas distributor, the edge being connected to a side wall of the inner cavity; and wherein the flat plate is provided with a plurality of second air holes that are in an annular arrangement and that have gradually increasing hole pitches in a direction from the center to the edge of the flat plate.

10. The sterilization exhaust gas treatment system according to claim 9, wherein the reaction column further comprises at least one stirrer and a filter screen, each being disposed in the inner cavity, and wherein the at least one stirrer is located above the filter screen.

11. The sterilization exhaust gas treatment system according to claim 1, wherein the temperature swing adsorption recovery system comprises:
an adsorption column comprising a column body, a sealing door, and a plurality of adsorbing structures;
a first pipe;
a second pipe; and
a heat exchanging system that is configured to cool or to heat the adsorption column;
wherein a gas channel is formed in the column body, extending longitudinally in the column body, wherein a side wall of at least one side portion of the column body is provided with a plurality of mounting holes, wherein each of the plurality of mounting holes is sequentially provided in a longitudinal direction and fluidly communicates with the gas channel;
wherein one end of the first pipe is provided at a bottom portion of the column body and fluidly communicates with a bottom portion of the gas channel, wherein the other end of the first pipe is configured to fluidly communicate with each of the reaction system and the recovery and storage system;
wherein one end of the second pipe is provided at a top portion of the column body and fluidly communicates with a top portion of the gas channel, wherein the other end of the second pipe is configured to fluidly communicate with the hydration system;
wherein the plurality of adsorbing structures extends into the gas channel, and is respectively slidably mounted on the column body through respective mounting holes;
wherein the sealing door is mounted on the side wall of the at least one side portion of the column body, and is capable of being opened and closed, and wherein, when the sealing door is closed, the plurality of mounting holes and the plurality of adsorbing structures are housed in a sealed environment; wherein at least one of the plurality of adsorbing structures comprises:
a supporting frame having a drawer-type structure, being slidably connected to a side wall of the gas channel, and being configured to accommodate an adsorbing material; and
a holder that is connected to the supporting frame for holding the adsorbing material in the supporting frame;
wherein the supporting frame is provided with a plurality of first ventilating holes, the holder being provided with a plurality of second ventilating holes.

12. The sterilization exhaust gas treatment system according to claim 11, wherein the adsorption column further comprises a gas distributor provided in the gas channel and being located below the plurality of adsorbing structures, wherein the gas distributor comprises a plurality of third ventilating holes that fluidly communicates with the first pipe and the gas channel.

13. The sterilization exhaust gas treatment system according to claim 1, wherein the hydration system comprises:
a liquid reservoir;
a hydration column, the hydration column being provided on a top portion of the liquid reservoir; and
a pump;
wherein one side portion of the liquid reservoir is fluidly connected to the pump via a first pipeline, and the pump is fluidly connected to the hydration column via a second pipeline;
wherein a bottom portion of the liquid reservoir is provided with a liquid outlet for fluidly connecting with the wastewater treatment system, wherein an air inlet is provided on a side portion of the liquid reservoir for fluidly connecting with the temperature swing adsorption recovery system, and wherein a gas diffuser is provided in an interior of the liquid reservoir, and is fluidly connected with the air inlet;
wherein the hydration column comprises a column body provided with a gas outlet on top thereof for discharging residual gas treated by the hydration column, wherein a spray device is arranged in a upper portion inside the column body and is fluidly connected to the pump via a pipeline, and wherein a gas distributor is provided below the spray device;
wherein the hydration column further comprises a water baffle and a gas guide plate both disposed at a top portion of the column body, wherein the water baffle and the gas guide plate are both disposed above the spray device, and wherein the water baffle is disposed between the gas guide plate and the spray device.

14. A method for treating ethylene oxide-containing sterilization exhaust gas using the sterilization exhaust gas treatment system according to claim 1, comprising:
S1, passing the ethylene oxide-containing sterilization exhaust gas into the gas liquefaction recovery system; pressurizing the gas liquefaction recovery system, so that ethylene oxide in the ethylene oxide-containing sterilization exhaust gas is compressed and liquefied to obtain ethylene oxide liquid and treated exhaust gas; and then recovering the ethylene oxide liquid and directing the recovered ethylene oxide liquid to the recovery and storage system;
S2, passing the exhaust gas treated by the gas liquefaction recovery system into the pressure swing adsorption recovery system to perform pressurized adsorption and depressurized desorption; and recovering ethylene oxide gas that is obtained by the depressurized desorption and directing the recovered ethylene oxide gas to the recovery and storage system;
S3, passing the exhaust gas treated by the pressure swing adsorption recovery system into the reaction system to acidize the ethylene oxide in the exhaust gas;
S4, passing the exhaust gas treated by the reaction system into the temperature swing adsorption recovery system for low-temperature adsorption and high-temperature desorption; and recovering the desorbed ethylene oxide gas and directing the recovered desorbed ethylene oxide gas to the recovery and storage system;
S5, passing the exhaust gas treated by the temperature swing adsorption recovery system into the hydration system, so that the ethylene oxide in the exhaust gas is treated by water absorption to obtain wastewater containing ethylene oxide; and S6, inputting the wastewater containing the ethylene oxide that is obtained by the hydration system into the wastewater treatment system.

15. The method according to claim 14, wherein the Step S6 comprises steps of:

S61, inputting the wastewater containing the ethylene oxide into an anaerobic microbial degradation system, so that primary degradation of the ethylene oxide in the wastewater is performed by anaerobic microbial ethylene oxide degrading bacteria in the anaerobic microbial degradation system;

S62, inputting the wastewater degraded by the anaerobic microbial degradation system into the aerobic microbial degradation system, so that secondary degradation of the ethylene oxide in the wastewater is performed by aerobic microbial ethylene oxide degrading bacteria in the aerobic microbial degradation system;

S63, inputting the wastewater degraded by an aerobic microbial degradation system into a biological monitoring system, so that trace amounts of ethylene oxide remaining in the wastewater are further purified by the biological monitoring system, which monitors a state of microorganisms in the wastewater, thereby monitoring an effect of wastewater treatment.

16. The method according to claim 14, having a feature selected from the group consisting of:
a) wherein in the Step S1, pressure of the exhaust gas after being pressurized in the gas liquefaction recovery system is between 0.7 MPa and 0.9 MPa;
b) wherein in the Step S2, in the pressure swing adsorption recovery system, pressure of the exhaust gas after being pressurized is between 0.4 MPa and 0.6 MPa, and pressure of the exhaust gas after being depressurized is between 0 MPa and 0.2 MPa;
c) wherein the Step S3 comprises treating the ethylene oxide in the exhaust gas with ethylene oxide catalytic concentrate, and the amount of the ethylene oxide catalytic concentrate is calculated based on 0.1 g-0.2 g of ethylene oxide per 1 g of ethylene oxide catalytic concentrate;
d) wherein in the Step S4, a temperature of the low-temperature adsorption is between 20° C. and 30° C., and a temperature of the high-temperature desorption is between 70° C. and 90° C.; wherein an adsorbent in the Step S4 is an activated carbon, and the amount of the activated carbon is calculated based on 0.1 g-0.15 g of ethylene oxide per 1 g of activated carbon; and
e) wherein the ethylene oxide-containing sterilization exhaust gas is from a gas sterilization device, and the method further comprises:
passing the recovered ethylene oxide from the recovery and storage system into the gas sterilization device for a next cycle of sterilization.

17. A sterilization exhaust gas treatment system, comprising:
a gas liquefaction recovery system;
a pressure swing adsorption recovery system;
a reaction system;
a temperature swing adsorption recovery system;
a hydration system; and
a recovery and storage system;
wherein the gas liquefaction recovery system, the pressure swing adsorption recovery system, the reaction system, the temperature swing adsorption recovery system, and the hydration system are fluidly connected in sequence through one or more first connecting pipes; and
wherein the gas liquefaction recovery system, the pressure swing adsorption recovery system, and the temperature swing adsorption recovery system are each fluidly connected to the recovery and storage system through one or more second connecting pipes.

18. The sterilization exhaust gas treatment system according to claim 17, having a feature selected from the group consisting of:
a) wherein the sterilization exhaust gas treatment system further comprises a wastewater treatment system that is fluidly connected to the hydration system, wherein the wastewater treatment system comprises:
an anaerobic microbial degradation system, an aerobic microbial degradation system, and a biological monitoring system; and wherein the hydration system and the wastewater treatment system are each fluidly connected to a fountain device through one or more fountain connection pipes wherein the hydration system, the anaerobic microbial degradation system, the aerobic microbial degradation system, and the biological monitoring system are fluidly connected in sequence through one or more wastewater pipes;
b) wherein the gas liquefaction recovery system comprises:
a gas liquefaction separator;
a gas intake pipe;
a pressurizing device; and
a gas extraction device;
wherein a gas inlet of the gas liquefaction separator is fluidly connected to the gas intake pipe;
wherein the pressurizing device and the gas extraction device are disposed on the gas intake pipe;
wherein a gas outlet of the gas liquefaction separator is fluidly connected to the pressure swing adsorption recovery system; and
wherein a liquid outlet of the gas liquefaction separator is fluidly connected to the recovery and storage system;
c) wherein the pressure swing adsorption recovery system comprises:
a first pressure swing adsorption column including a first accommodating chamber, a first gas vent, and a first gas outlet, the first gas vent and the first gas outlet being in fluid communication with the first accommodating chamber, wherein the first accommodating chamber is configured to accommodate an adsorbing material;
a first thermostatic assembly, wherein the first pressure swing adsorption column is at least partially provided near the first thermostatic assembly;
a first branch pipe; and
a second branch pipe, the first branch pipe and the second branch pipe each being configured to fluidly communicate with the first gas vent;
wherein the first branch pipe is configured to provide fluid communication between the first gas vent and the recovery and storage system;
wherein the second branch pipe is configured to provide fluid communication between the first gas vent and a gas outlet of the gas liquefaction recovery system; and
wherein the first gas outlet is in fluid communication with the reaction system;

d) wherein the reaction system comprises a reaction column comprising:
   a column body, with an inner cavity configured for containing a liquid substrate;
   wherein the column body has a bottom portion that is provided with a gas inlet pipe and a liquid outlet pipe, wherein the gas inlet pipe is configured to inject ethylene oxide-containing sterilization exhaust gas into the inner cavity, and wherein the liquid outlet pipe is configured to discharge, from the inner cavity, the liquid substrate that has been used to catalyze ethylene oxide in ethylene oxide-containing sterilization exhaust gas;
   wherein the column body has a top portion that is provided with a gas outlet pipe with a gas inlet that is disposed above a liquid level of the liquid substrate; and
   at least one gas distributor, which is provided in the inner cavity above a gas outlet of the gas inlet pipe, is configured to disperse the ethylene oxide-containing sterilization exhaust gas that is injected into the inner cavity via the gas inlet pipe;
e) wherein the temperature swing adsorption recovery system comprises:
   an adsorption column comprising a column body, a sealing door, and a plurality of adsorbing structures;
   a first pipe;
   a second pipe; and
   a heat exchanging system that is configured to cool or to heat the adsorption column;
   wherein a gas channel is formed in the column body, extending longitudinally in the column body, wherein a side wall of at least one side portion of the column body is provided with a plurality of mounting holes, wherein each of the plurality of mounting holes is sequentially provided in a longitudinal direction and fluidly communicates with the gas channel;
   wherein one end of the first pipe is provided at a bottom portion of the column body and fluidly communicates with a bottom portion of the gas channel, wherein the other end of the first pipe is configured to fluidly communicate with each of the reaction system and the recovery and storage system;
   wherein one end of the second pipe is provided at a top portion of the column body and fluidly communicates with a top portion of the gas channel, wherein the other end of the second pipe is configured to fluidly communicate with the hydration system;
   wherein the plurality of adsorbing structures extends into the gas channel, and is respectively slidably mounted on the column body through respective mounting holes; and
   wherein the sealing door is mounted on the side wall of the at least one side portion of the column body, and is capable of being opened and closed, and wherein, when the sealing door is closed, the plurality of mounting holes and the plurality of adsorbing structures are housed in a sealed environment; and
f) wherein the hydration system comprises:
   a liquid reservoir;
   a hydration column, the hydration column being provided on a top portion of the liquid reservoir; and
   a pump;
   wherein one side portion of the liquid reservoir is fluidly connected to the pump via a first pipeline, and the pump is fluidly connected to the hydration column via a second pipeline;
   wherein a bottom portion of the liquid reservoir is provided with a liquid outlet for fluidly connecting with the wastewater treatment system, wherein an air inlet is provided on a side portion of the liquid reservoir for fluidly connecting with the temperature swing adsorption recovery system, and wherein a gas diffuser is provided in an interior of the liquid reservoir, and is fluidly connected with the air inlet;
   wherein the hydration column comprises a column body provided with a gas outlet on top thereof for discharging residual gas treated by the hydration column, wherein a spray device is arranged in a upper portion inside the column body and is fluidly connected to the pump via a pipeline, and wherein a gas distributor is provided below the spray device.

19. The sterilization exhaust gas treatment system of claim 17, further comprising:
   a) a gas sterilization device;
      wherein the gas liquefaction recovery system and the hydration system are each fluidly connected to the gas sterilization device through one or more gas sterilization pipes; and
   b) a fountain device;
      wherein the hydration system and a wastewater treatment system are each fluidly connected to the fountain device through one or more fountain connection pipes.

20. The sterilization exhaust gas treatment system of claim 17, wherein the gas liquefaction recovery system comprises:
   a gas liquefaction separator;
   a gas intake pipe;
   a pressurizing device; and
   a gas extraction device;
   wherein a gas inlet of the gas liquefaction separator is fluidly connected to the gas intake pipe;
   wherein the pressurizing device and the gas extraction device are disposed on the gas intake pipe;
   wherein a gas outlet of the gas liquefaction separator is fluidly connected to the pressure swing adsorption recovery system;
   wherein a liquid outlet of the gas liquefaction separator is fluidly connected to the recovery and storage system;
   wherein the gas liquefaction separator comprises:
      a housing, wherein the housing comprises a gas outlet that is provided at a top portion of the housing, a gas inlet that is provided at an inner side wall of the housing, and a liquid outlet that is provided at a bottom portion of the housing;
      a blocking plate, wherein the blocking plate extends downward from a top wall of an inner cavity of the housing, wherein the gas inlet is opposite to the blocking plate;
      a gas baffle, wherein the gas baffle is located below the blocking plate; and
      a liquid collector, wherein the liquid collector is located below the gas baffle, wherein an outer edge of the liquid collector is connected to the inner side wall of the housing;
      wherein the blocking plate, the gas baffle, and the liquid collector are located in the housing;
      wherein the liquid collector comprises a first flow guide surface, wherein a bottom portion of the first flow guide surface is provided with a first hole; and
      wherein an upper surface of the gas baffle forms a second flow guide surface, wherein an outer edge of the gas baffle is provided with at least one protrusion, and wherein the gas baffle is connected to the first flow guide surface through the at least one protrusion, thereby forming a second hole between the outer edge of the gas baffle and the first flow guide surface.

21. The sterilization exhaust gas treatment system according to claim 20, having a feature selected from the group consisting of:
  a) wherein the inner cavity of the housing comprises:
    an upstream chamber;
    a downstream chamber; and
    a lower chamber, the upstream chamber and the downstream chamber being divided by the blocking plate, and the lower chamber being located below the blocking plate;
    wherein a bottom portion of the upstream chamber and a bottom portion of the downstream chamber are in fluid communication with each other through the lower chamber;
    wherein the gas inlet corresponds to the upstream chamber, wherein the gas outlet corresponds to the downstream chamber, and wherein the liquid outlet corresponds to the lower chamber; and
    wherein the gas baffle is located in the lower chamber, and wherein the liquid collector is located in the lower chamber; and
  b) wherein the second flow guide surface has a shape with a higher middle portion and lower edges; wherein the at least one protrusion comprises a plurality of protrusions; and wherein the plurality of protrusions is arranged such that they are spaced apart from each other along a circumference of the gas baffle.

22. The sterilization exhaust gas treatment system according to claim 17, wherein the pressure swing adsorption recovery system comprises:
  a first pressure swing adsorption column including a first accommodating chamber, a first gas vent, and a first gas outlet, the first gas vent and the first gas outlet being in fluid communication with the first accommodating chamber, wherein the first accommodating chamber is configured to accommodate an adsorbing material;
  a first thermostatic assembly, wherein the first pressure swing adsorption column is at least partially provided near the first thermostatic assembly;
  a first branch pipe; and
  a second branch pipe, the first branch pipe and the second branch pipe each being configured to fluidly communicate with the first gas vent;
  wherein the first branch pipe is configured to provide fluid communication between the first gas vent and the recovery and storage system;
  wherein the second branch pipe is configured to provide fluid communication between the first gas vent and a gas outlet of the gas liquefaction recovery system; and
  wherein the first gas outlet is in fluid communication with the reaction system; and further comprising:
    a second pressure swing adsorption column, including a second accommodating chamber, a second gas vent, and a second gas outlet, the second gas vent and the second gas outlet being in fluid communication with the second accommodating chamber, wherein the second accommodating chamber is configured to accommodate the adsorbing material;
    a second thermostatic assembly, wherein the second pressure swing adsorption column is at least partially provided near the second thermostatic assembly;
    a third branch pipe; and
    a fourth branch pipe;
    wherein the third branch pipe is configured to provide fluid communication between the second gas vent and the recovery and storage system;
    wherein the fourth branch pipe is configured to provide fluid communication between the second gas vent and the gas outlet of the gas liquefaction recovery system;
    wherein the second gas outlet is in fluid communication with the reaction system.

23. The sterilization exhaust gas treatment system according to claim 22, wherein the first pressure swing adsorption column comprises:
  a first column body;
  a first upper sealing cover; and
  a first lower sealing cover, the first upper sealing cover and the first lower sealing cover being connected to top and bottom ends of the first column body, respectively;
  wherein the first accommodating chamber is enclosed by the first column body, the first upper sealing cover, and the first lower sealing cover; and
  wherein a water-absorbing material and an oil-absorbing material are sequentially provided between the first lower sealing cover and the adsorbing material along a direction close to the adsorbing material.

24. The sterilization exhaust gas treatment system according to claim 23, wherein:
  a first-stage gas distributor is provided between the first lower sealing cover and the water-absorbing material, wherein the first-stage gas distributor is provided with a plurality of holes, and wherein a diameter of the holes is smaller than a particle size of the water-absorbing material; and
  a second-stage gas distributor is provided between the water-absorbing material and the oil-absorbing material, wherein a lower mesh plate is provided between the oil-absorbing material and the adsorbing material.

25. The sterilization exhaust gas treatment system according to claim 17, wherein the reaction system comprises a reaction column comprising:
  a column body, with an inner cavity configured for containing a liquid substrate;
  wherein the column body has a bottom portion that is provided with a gas inlet pipe and a liquid outlet pipe, wherein the gas inlet pipe is configured to inject ethylene oxide-containing sterilization exhaust gas into the inner cavity, and wherein the liquid outlet pipe is configured to discharge, from the inner cavity, the liquid substrate that has been used to catalyze ethylene oxide in ethylene oxide-containing sterilization exhaust gas;
  wherein the column body has a top portion that is provided with a gas outlet pipe with a gas inlet that is disposed above a liquid level of the liquid substrate;
  at least one gas distributor, which is provided in the inner cavity above a gas outlet of the gas inlet pipe, is configured to disperse the ethylene oxide-containing sterilization exhaust gas that is injected into the inner cavity via the gas inlet pipe; and
  wherein the at least one gas distributor comprises a first gas distributor, the first gas distributor being a curved plate with a center and an edge, the center being high and the edge being low relative to each other; wherein the edge of the curved plate is connected to a bottom wall of the inner cavity; wherein the curved plate is provided with a plurality of first air holes in an annular arrangement; wherein the gas inlet pipe fluidly communicates with the gas outlet pipe through the plurality of first air holes; and wherein the plurality of first air holes gradually increases in hole size in a direction from the center to the edge of the curved plate.

26. The sterilization exhaust gas treatment system according to claim 25, wherein the at least one gas distributor further comprises a second gas distributor, the second gas distributor being a flat plate with a center and an edge, and being located above the first gas distributor, the edge being connected to a side wall of the inner cavity; and wherein the flat plate is provided with a plurality of second air holes that are in an annular arrangement and that have gradually increasing hole pitches in a direction from the center to the edge of the flat plate.

27. The sterilization exhaust gas treatment system according to claim 26, wherein the reaction system comprises a reaction column comprising:
a column body, with an inner cavity configured for containing a liquid substrate;
wherein the column body has a bottom portion that is provided with a gas inlet pipe and a liquid outlet pipe, wherein the gas inlet pipe is configured to inject ethylene oxide-containing sterilization exhaust gas into the inner cavity, and wherein the liquid outlet pipe is configured to discharge, from the inner cavity, the liquid substrate that has been used to catalyze ethylene oxide in ethylene oxide-containing sterilization exhaust gas;
wherein the column body has a top portion that is provided with a gas outlet pipe with a gas inlet that is disposed above a liquid level of the liquid substrate; and
at least one gas distributor, which is provided in the inner cavity above a gas outlet of the gas inlet pipe, is configured to disperse the ethylene oxide-containing sterilization exhaust gas that is injected into the inner cavity via the gas inlet pipe; and
wherein the reaction column further comprises at least one stirrer and a filter screen, each being disposed in the inner cavity, and wherein the at least one stirrer is located above the filter screen.

28. The sterilization exhaust gas treatment system according to claim 17, wherein the temperature swing adsorption recovery system comprises:
an adsorption column comprising a column body, a sealing door, and a plurality of adsorbing structures;
a first pipe;
a second pipe; and
a heat exchanging system that is configured to cool or to heat the adsorption column;
wherein a gas channel is formed in the column body, extending longitudinally in the column body, wherein a side wall of at least one side portion of the column body is provided with a plurality of mounting holes, wherein each of the plurality of mounting holes is sequentially provided in a longitudinal direction and fluidly communicates with the gas channel;
wherein one end of the first pipe is provided at a bottom portion of the column body and fluidly communicates with a bottom portion of the gas channel, wherein the other end of the first pipe is configured to fluidly communicate with each of the reaction system and the recovery and storage system;
wherein one end of the second pipe is provided at a top portion of the column body and fluidly communicates with a top portion of the gas channel, wherein the other end of the second pipe is configured to fluidly communicate with the hydration system;
wherein the plurality of adsorbing structures extends into the gas channel, and is respectively slidably mounted on the column body through respective mounting holes;
wherein the sealing door is mounted on the side wall of the at least one side portion of the column body, and is capable of being opened and closed, and wherein, when the sealing door is closed, the plurality of mounting holes and the plurality of adsorbing structures are housed in a sealed environment;
wherein at least one of the plurality of adsorbing structures comprises:
a supporting frame having a drawer-type structure, being slidably connected to a side wall of the gas channel, and being configured to accommodate an adsorbing material;
a holder that is connected to the supporting frame for holding the adsorbing material in the supporting frame;
wherein the supporting frame is provided with a plurality of first ventilating holes, the holder being provided with a plurality of second ventilating holes;
wherein the adsorption column further comprises a gas distributor provided in the gas channel and being located below the plurality of adsorbing structures, wherein the gas distributor comprises a plurality of third ventilating holes that fluidly communicates with the first pipe and the gas channel.

29. The sterilization exhaust gas treatment system according to claim 17, wherein the hydration system comprises:
a liquid reservoir;
a hydration column, the hydration column being provided on a top portion of the liquid reservoir; and
a pump;
wherein one side portion of the liquid reservoir is fluidly connected to the pump via a first pipeline, and the pump is fluidly connected to the hydration column via a second pipeline;
wherein a bottom portion of the liquid reservoir is provided with a liquid outlet for fluidly connecting with a wastewater treatment system, wherein an air inlet is provided on a side portion of the liquid reservoir for fluidly connecting with the temperature swing adsorption recovery system, and wherein a gas diffuser is provided in an interior of the liquid reservoir, and is fluidly connected with the air inlet;
wherein the hydration column comprises a column body provided with a gas outlet on top thereof for discharging residual gas treated by the hydration column, wherein a spray device is arranged in an upper portion inside the column body and is fluidly connected to the pump via a pipeline, and wherein a gas distributor is provided below the spray device; and
wherein the hydration column further comprises a water baffle and a gas guide plate both disposed at a top portion of the column body, wherein the water baffle and the gas guide plate are both disposed above the spray device, and wherein the water baffle is disposed between the gas guide plate and the spray device.

30. A method for treating ethylene oxide-containing sterilization exhaust gas, comprising:
treating ethylene oxide-containing sterilization exhaust gas using a sterilization exhaust gas treatment system, the sterilization exhaust gas treatment system comprising:

a gas liquefaction recovery system;
a pressure swing adsorption recovery system;
a reaction system;
a temperature swing adsorption recovery system;
a hydration system;
a recovery and storage system; and
a wastewater treatment system;
wherein the gas liquefaction recovery system, the pressure swing adsorption recovery system, the reaction system, the temperature swing adsorption recovery system, and the hydration system are fluidly connected in sequence through one or more first connecting pipes;
wherein the gas liquefaction recovery system, the pressure swing adsorption recovery system, and the temperature swing adsorption recovery system are each fluidly connected to the recovery and storage system through one or more second connecting pipes; and
wherein the hydration system is fluidly connected to the wastewater treatment system through one or more wastewater pipes;
wherein treating ethylene oxide-containing sterilization exhaust gas comprises the following steps:
S1, passing the ethylene oxide-containing sterilization exhaust gas into the gas liquefaction recovery system; pressurizing the gas liquefaction recovery system, so that ethylene oxide in the ethylene oxide-containing sterilization exhaust gas is compressed and liquefied to obtain ethylene oxide liquid and treated exhaust gas; and then recovering the ethylene oxide liquid and directing the recovered ethylene oxide liquid to the recovery and storage system;
S2, passing the exhaust gas treated by the gas liquefaction recovery system into the pressure swing adsorption recovery system to perform pressurized adsorption and depressurized desorption; and recovering ethylene oxide gas that is obtained by the depressurized desorption and directing the recovered ethylene oxide gas to the recovery and storage system;
S3, passing the exhaust gas treated by the pressure swing adsorption recovery system into the reaction system to acidize the ethylene oxide in the exhaust gas;
S4, passing the exhaust gas treated by the reaction system into the temperature swing adsorption recovery system for low-temperature adsorption and high-temperature desorption; and recovering the desorbed ethylene oxide gas and directing the recovered desorbed ethylene oxide gas to the recovery and storage system;
S5, passing the exhaust gas treated by the temperature swing adsorption recovery system into the hydration system, so that the ethylene oxide in the exhaust gas is treated by water absorption to obtain wastewater containing ethylene oxide; and S6, inputting the wastewater containing the ethylene oxide that is obtained by the hydration system into the wastewater treatment system; wherein the Step S6 optionally comprises steps of:
S61, inputting the wastewater containing the ethylene oxide into an anaerobic microbial degradation system, so that primary degradation of the ethylene oxide in the wastewater is performed by anaerobic microbial ethylene oxide degrading bacteria in the anaerobic microbial degradation system;
S62, inputting the wastewater degraded by the anaerobic microbial degradation system into an aerobic microbial degradation system, so that secondary degradation of the ethylene oxide in the wastewater is performed by aerobic microbial ethylene oxide degrading bacteria in the aerobic microbial degradation system;
S63, inputting the waste water degraded by the aerobic microbial degradation system into a biological monitoring system, so that trace amounts of ethylene oxide remaining in the wastewater are further purified by the biological monitoring system, which monitors a state of microorganisms in the wastewater, thereby monitoring an effect of wastewater treatment; and
wherein the method has a feature selected from the group consisting of:
a) wherein in the Step S1, pressure of the exhaust gas after being pressurized in the gas liquefaction recovery system is between 0.7 MPa and 0.9 MPa;
b) wherein in the Step S2, in the pressure swing adsorption recovery system, pressure of the exhaust gas after being pressurized is between 0.4 MPa and 0.6 MPa, and pressure of the exhaust gas after being depressurized is between 0 MPa and 0.2 MPa;
c) wherein the Step S3 comprises treating the ethylene oxide in the exhaust gas with ethylene oxide catalytic concentrate, and the amount of the ethylene oxide catalytic concentrate is calculated based on 0.1 g-0.2 g of ethylene oxide per 1 g of ethylene oxide catalytic concentrate;
d) wherein in the Step S4, a temperature of the low-temperature adsorption is between 20° C. and 30° C., and a temperature of the high-temperature desorption is between 70° C. and 90° C.; wherein an adsorbent in the Step S4 is an activated carbon, and the amount of the activated carbon is calculated based on 0.1 g-0.15 g of ethylene oxide per 1 g of activated carbon; and
e) wherein the ethylene oxide-containing sterilization exhaust gas is from a gas sterilization device, and the method further comprises:
passing the recovered ethylene oxide from the recovery and storage system into the gas sterilization device for a next cycle of sterilization.

* * * * *